US009708399B2

(12) United States Patent
Wang et al.

(10) Patent No.: US 9,708,399 B2
(45) Date of Patent: Jul. 18, 2017

(54) PROTEIN PURIFICATION USING DISPLACEMENT CHROMATOGRAPHY

(71) Applicant: AbbVie, Inc., North Chicago, IL (US)

(72) Inventors: Chen Wang, Shrewsbury, MA (US); Germano Coppola, Shrewsbury, MA (US); Chris Chumsae, North Andover, MA (US)

(73) Assignee: ABBVIE, INC., North Chicago, IL (US)

( * ) Notice: Subject to any disclaimer, the term of this patent is extended or adjusted under 35 U.S.C. 154(b) by 0 days.

(21) Appl. No.: 14/733,085

(22) Filed: Jun. 8, 2015

(65) Prior Publication Data

US 2015/0329588 A1    Nov. 19, 2015

Related U.S. Application Data

(63) Continuation of application No. 13/803,808, filed on Mar. 14, 2013, now Pat. No. 9,067,990.

(51) Int. Cl.
A61K 38/00    (2006.01)
A61K 39/00    (2006.01)
C07K 16/00    (2006.01)
C07K 16/24    (2006.01)
C07K 1/18     (2006.01)
(Continued)

(52) U.S. Cl.
CPC .............. C07K 16/241 (2013.01); C07K 1/18 (2013.01); C07K 1/20 (2013.01); C07K 1/22 (2013.01); C07K 2317/14 (2013.01); C07K 2317/21 (2013.01); C07K 2317/76 (2013.01); C07K 2317/90 (2013.01)

(58) Field of Classification Search
CPC .... C07K 16/241; C07K 1/165; C07K 14/525; C07K 1/18; C07K 16/00; C07K 2317/14; C07K 1/20; C07K 1/22; A61K 39/39591; C12P 21/00
See application file for complete search history.

(56) References Cited

U.S. PATENT DOCUMENTS

RE30,985 E    6/1982 Cartaya
4,399,216 A   8/1983 Axel et al.
(Continued)

FOREIGN PATENT DOCUMENTS

CN    1 563090 A     1/2005
CN    105777895 A    7/2016
(Continued)

OTHER PUBLICATIONS

"Genentech unveils production capacity hikes," in-Pharma Technologist.com Jun. 28, 2005, pp. 1-2.
(Continued)

Primary Examiner — Cherie M Stanfield
(74) Attorney, Agent, or Firm — McCarter & English, LLP; Maria Laccotripe Zacharakis; Marcie B. Clarke

(57) ABSTRACT

Disclosed herein are compositions and methods for the isolation and purification of proteins from a sample. In particular, the present invention relates to compositions and methods for isolating and purifying proteins incorporating a displacement chromatographic step. The present invention is also directed toward pharmaceutical compositions comprising one or more antibodies purified by a method described herein.

31 Claims, 18 Drawing Sheets

(51) Int. Cl.
*C07K 1/20* (2006.01)
*C07K 1/22* (2006.01)

(56) References Cited

U.S. PATENT DOCUMENTS

| | | |
|---|---|---|
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,925,796 A | 5/1990 | Bergh et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,047,335 A | 9/1991 | Paulson et al. |
| 5,096,816 A | 3/1992 | Maiorella |
| 5,110,913 A | 5/1992 | Coan et al. |
| 5,112,469 A | 5/1992 | Kempf et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,169,936 A | 12/1992 | Staples et al. |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,605,923 A | 2/1997 | Christensen, IV et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,730,975 A | 3/1998 | Hotamisligil et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,945,311 A | 8/1999 | Lindhofer et al. |
| 5,976,833 A | 11/1999 | Furukawa et al. |
| 5,989,830 A | 11/1999 | Davis et al. |
| 5,994,510 A | 11/1999 | Adair et al. |
| 6,005,082 A | 12/1999 | Smeds |
| 6,015,558 A | 1/2000 | Hotamisligil et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,093,324 A | 7/2000 | Bertolini et al. |
| 6,113,898 A | 9/2000 | Anderson et al. |
| 6,150,584 A | 11/2000 | Kucherlapati et al. |
| 6,171,586 B1 | 1/2001 | Lam et al. |
| 6,171,825 B1 | 1/2001 | Chan et al. |
| 6,235,281 B1 | 5/2001 | Stenzel et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,506,598 B1 | 1/2003 | Andersen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,656,466 B1 | 12/2003 | Etcheverry et al. |
| 6,673,575 B1 | 1/2004 | Franze et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,936,441 B2 | 8/2005 | Reiter et al. |
| 6,974,681 B1 | 12/2005 | McGrew |
| 7,029,872 B2 | 4/2006 | Gerngross |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,229,432 B2 | 6/2007 | Marshall et al. |
| 7,250,165 B2 | 7/2007 | Heavner et al. |
| 7,276,239 B2 | 10/2007 | Le et al. |
| 7,297,680 B2 | 11/2007 | Opstelten et al. |
| 7,323,553 B2 | 1/2008 | Fahrner et al. |
| 7,326,681 B2 | 2/2008 | Gerngross |
| 7,332,303 B2 | 2/2008 | Schilling et al. |
| 7,390,660 B2 | 6/2008 | Behrendt et al. |
| 7,427,659 B2 | 9/2008 | Shukla et al. |
| 7,429,491 B2 | 9/2008 | Luan et al. |
| 7,449,308 B2 | 11/2008 | Gerngross et al. |
| 7,473,680 B2 | 1/2009 | DeFrees et al. |
| 7,504,485 B2 | 3/2009 | Salfeld et al. |
| 7,517,670 B2 | 4/2009 | Umana et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,612,181 B2 | 11/2009 | Wu et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,906,329 B2 | 3/2011 | Umana et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,034,906 B2 | 10/2011 | Borhani et al. |
| 8,043,863 B2 | 10/2011 | Bosques et al. |
| 8,053,236 B2 | 11/2011 | Morris et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |

(56) References Cited

U.S. PATENT DOCUMENTS

| | | | |
|---|---|---|---|
| 8,216,583 B2 | 7/2012 | Kruase et al. | |
| 8,216,851 B2 | 7/2012 | Parsons et al. | |
| 8,231,876 B2 | 7/2012 | Wan et al. | |
| 8,304,250 B2 | 11/2012 | Parsons et al. | |
| 8,313,925 B2 | 11/2012 | Gregory et al. | |
| 8,338,088 B2 | 12/2012 | Collins et al. | |
| 8,361,705 B2 | 1/2013 | Parsons et al. | |
| 8,361,797 B2 | 1/2013 | Osborne et al. | |
| 8,372,400 B2 | 2/2013 | Salfeld et al. | |
| 8,372,401 B2 | 2/2013 | Salfeld et al. | |
| 8,388,965 B2 | 3/2013 | Rao et al. | |
| 8,399,627 B2 | 3/2013 | Votsmeier et al. | |
| 8,414,894 B2 | 4/2013 | Salfeld et al. | |
| 8,420,081 B2 | 4/2013 | Fraunhofer et al. | |
| 8,436,149 B2 | 5/2013 | Borhani et al. | |
| 8,470,318 B2 | 6/2013 | Ravetch et al. | |
| 8,470,552 B2 | 6/2013 | Croughan et al. | |
| 8,512,983 B2 | 8/2013 | Gawlitzek et al. | |
| 8,530,192 B2 | 9/2013 | Knudsen | |
| 8,586,356 B2 | 11/2013 | Bosques et al. | |
| 8,623,644 B2 | 1/2014 | Umana et al. | |
| 8,629,248 B2 | 1/2014 | Umana et al. | |
| 8,632,773 B2 | 1/2014 | Kasermann et al. | |
| 8,652,487 B2 | 2/2014 | Maldonado | |
| 8,663,945 B2 | 3/2014 | Pla et al. | |
| 8,663,999 B2 | 3/2014 | Parsons et al. | |
| 8,703,498 B2 | 4/2014 | Parsons et al. | |
| 8,729,241 B2 | 5/2014 | Liu et al. | |
| 8,753,633 B2 | 6/2014 | Salfeld et al. | |
| 8,821,865 B2 | 9/2014 | Neu et al. | |
| 8,852,889 B2 | 10/2014 | Prentice | |
| 8,883,146 B2 | 11/2014 | Fraunhofer et al. | |
| 8,883,156 B2 | 11/2014 | Wan et al. | |
| 8,895,009 B2 | 11/2014 | Wan et al. | |
| 8,895,709 B2 | 11/2014 | Hickman et al. | |
| 8,906,372 B2 | 12/2014 | Wan et al. | |
| 8,906,646 B2 | 12/2014 | Pla et al. | |
| 8,911,964 B2 | 12/2014 | Pla et al. | |
| 8,916,153 B2 | 12/2014 | Wan et al. | |
| 8,921,526 B2 | 12/2014 | Chumsae et al. | |
| 8,946,395 B1 | 2/2015 | Herigstad et al. | |
| 8,969,024 B2 | 3/2015 | Kaymkcalan et al. | |
| 9,017,687 B1* | 4/2015 | Wang | C07K 16/241 424/142.1 |
| 9,018,361 B2 | 4/2015 | Hickman et al. | |
| 9,023,992 B2 | 5/2015 | Rasmussen et al. | |
| 9,035,027 B2 | 5/2015 | Ghayur et al. | |
| 9,062,106 B2 | 6/2015 | Bengea et al. | |
| 9,067,990 B2* | 6/2015 | Wang | C07K 16/241 |
| 9,073,988 B2 | 7/2015 | Pla et al. | |
| 9,085,618 B2 | 7/2015 | Ramasubramanyan et al. | |
| 9,085,619 B2 | 7/2015 | Fraunhofer et al. | |
| 9,090,688 B2 | 7/2015 | Bengea et al. | |
| 9,090,867 B2 | 7/2015 | Pla et al. | |
| 9,096,666 B2 | 8/2015 | Wan et al. | |
| 9,096,879 B2 | 8/2015 | Khetan et al. | |
| 9,102,723 B2 | 8/2015 | Wan et al. | |
| 9,103,821 B2 | 8/2015 | Bosques et al. | |
| 9,109,010 B2 | 8/2015 | Hickman et al. | |
| 9,144,755 B2 | 9/2015 | Brown et al. | |
| 9,150,645 B2 | 10/2015 | Subramanian et al. | |
| 9,181,337 B2 | 11/2015 | Subramanian et al. | |
| 9,181,572 B2 | 11/2015 | Subramanian et al. | |
| 9,182,467 B2 | 11/2015 | Parsons et al. | |
| 9,200,069 B2 | 12/2015 | Ramasubramanyan et al. | |
| 9,200,070 B2 | 12/2015 | Ramasubramanyan et al. | |
| 9,206,390 B2 | 12/2015 | Rives et al. | |
| 9,234,032 B2 | 1/2016 | Pla et al. | |
| 9,234,033 B2 | 1/2016 | Rives et al. | |
| 9,249,182 B2 | 2/2016 | Herigstad et al. | |
| 9,255,143 B2 | 2/2016 | Bengea et al. | |
| 9,265,815 B2 | 2/2016 | Fraser et al. | |
| 9,266,949 B2 | 2/2016 | Ramasubramanyan et al. | |
| 9,273,132 B2 | 3/2016 | Wan et al. | |
| 9,284,371 B2 | 3/2016 | Pla et al. | |
| 9,290,568 B2 | 3/2016 | Rives et al. | |
| 9,315,574 B2* | 4/2016 | Ramasubramanyan | |
| 9,328,165 B2 | 5/2016 | Wan et al. | |
| 9,334,319 B2 | 5/2016 | Ramasubramanyan et al. | |
| 9,346,879 B2* | 5/2016 | Ramasubramanyan | C07K 1/165 |
| 9,359,434 B2 | 6/2016 | Subramanian et al. | |
| 9,365,645 B1 | 6/2016 | Bengea et al. | |
| 2001/0021525 A1 | 9/2001 | Hirai et al. | |
| 2002/0045207 A1 | 4/2002 | Krummen et al. | |
| 2002/0119530 A1 | 8/2002 | Maiorella et al. | |
| 2002/0132299 A1 | 9/2002 | Field | |
| 2002/0137673 A1 | 9/2002 | Pingel et al. | |
| 2002/0187526 A1 | 12/2002 | Ruben et al. | |
| 2003/0012786 A1 | 1/2003 | Teoh et al. | |
| 2003/0049725 A1 | 3/2003 | Heavner et al. | |
| 2003/0096414 A1 | 5/2003 | Ciccarone et al. | |
| 2003/0125247 A1 | 7/2003 | Rosen et al. | |
| 2003/0153735 A1 | 8/2003 | Breece et al. | |
| 2003/0157108 A1 | 8/2003 | Presta | |
| 2003/0161828 A1 | 8/2003 | Abdelghany et al. | |
| 2003/0166869 A1 | 9/2003 | Vedantham et al. | |
| 2003/0170813 A1 | 9/2003 | Suga et al. | |
| 2003/0175884 A1 | 9/2003 | Umana et al. | |
| 2003/0178368 A1 | 9/2003 | van Reis | |
| 2003/0203448 A1 | 10/2003 | Reiter et al. | |
| 2003/0206898 A1 | 11/2003 | Fischkoff et al. | |
| 2003/0211573 A1 | 11/2003 | Ryll | |
| 2003/0219438 A1 | 11/2003 | Salfeld et al. | |
| 2003/0229212 A1 | 12/2003 | Fahrner et al. | |
| 2003/0235585 A1 | 12/2003 | Fischkoff et al. | |
| 2004/0009172 A1 | 1/2004 | Fischkoff et al. | |
| 2004/0029229 A1 | 2/2004 | Reeves et al. | |
| 2004/0033228 A1 | 2/2004 | Krause et al. | |
| 2004/0033535 A1 | 2/2004 | Boyle et al. | |
| 2004/0038878 A1 | 2/2004 | Tanikawa et al. | |
| 2004/0043446 A1 | 3/2004 | DeFrees et al. | |
| 2004/0101939 A1 | 5/2004 | Santora et al. | |
| 2004/0120952 A1 | 6/2004 | Knight et al. | |
| 2004/0126372 A1 | 7/2004 | Banerjee et al. | |
| 2004/0126373 A1 | 7/2004 | Banerjee et al. | |
| 2004/0131614 A1 | 7/2004 | Banerjee et al. | |
| 2004/0132140 A1 | 7/2004 | Satoh et al. | |
| 2004/0136986 A1 | 7/2004 | Raju | |
| 2004/0136989 A1 | 7/2004 | Banerjee et al. | |
| 2004/0136990 A1 | 7/2004 | Banerjee et al. | |
| 2004/0136991 A1 | 7/2004 | Banerjee et al. | |
| 2004/0151722 A1 | 8/2004 | Banerjee et al. | |
| 2004/0162414 A1 | 8/2004 | Santora et al. | |
| 2004/0166111 A1 | 8/2004 | Kaymakcalan et al. | |
| 2004/0171152 A1 | 9/2004 | Price et al. | |
| 2004/0191243 A1 | 9/2004 | Chen et al. | |
| 2004/0191256 A1 | 9/2004 | Raju | |
| 2004/0214289 A1 | 10/2004 | deVries et al. | |
| 2004/0219142 A1 | 11/2004 | Banerjee et al. | |
| 2005/0004354 A1 | 1/2005 | Salfeld et al. | |
| 2005/0084969 A1 | 4/2005 | Schorgendorfer et al. | |
| 2005/0100965 A1 | 5/2005 | Ghayur et al. | |
| 2005/0123541 A1 | 6/2005 | Heavner et al. | |
| 2005/0175611 A1 | 8/2005 | Mahler et al. | |
| 2005/0249735 A1 | 11/2005 | Le et al. | |
| 2005/0271654 A1 | 12/2005 | Rinderknecht et al. | |
| 2005/0272124 A1 | 12/2005 | Chen et al. | |
| 2006/0009385 A1 | 1/2006 | Hoffman et al. | |
| 2006/0018907 A1 | 1/2006 | Le et al. | |
| 2006/0024293 A1 | 2/2006 | Salfeld et al. | |
| 2006/0057638 A1 | 3/2006 | Bosques et al. | |
| 2006/0083741 A1 | 4/2006 | Hoffman et al. | |
| 2006/0127950 A1 | 6/2006 | Bosques et al. | |
| 2006/0149042 A1 | 7/2006 | Konstantinov et al. | |
| 2006/0223147 A1 | 10/2006 | Nishiya et al. | |
| 2006/0246073 A1 | 11/2006 | Knight et al. | |
| 2006/0252672 A1 | 11/2006 | Betenbaugh et al. | |
| 2006/0269479 A1 | 11/2006 | Colton et al. | |
| 2006/0275867 A1 | 12/2006 | Chotteau et al. | |
| 2006/0287432 A1 | 12/2006 | Christensen et al. | |
| 2007/0003548 A1 | 1/2007 | Heavner et al. | |
| 2007/0004009 A1 | 1/2007 | Dixit et al. | |
| 2007/0015239 A1 | 1/2007 | Bihoreau et al. | |

(56) References Cited

U.S. PATENT DOCUMENTS

| | | |
|---|---|---|
| 2007/0020260 A1 | 1/2007 | Presta |
| 2007/0041905 A1 | 2/2007 | Hoffman et al. |
| 2007/0054390 A1 | 3/2007 | Kelley et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0134256 A1 | 6/2007 | Lai et al. |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0212770 A1 | 9/2007 | Grillberger et al. |
| 2007/0248600 A1 | 10/2007 | Hansen et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0009040 A1 | 1/2008 | Grillberger et al. |
| 2008/0025976 A1 | 1/2008 | Le et al. |
| 2008/0058507 A1 | 3/2008 | Liu et al. |
| 2008/0095762 A1 | 4/2008 | Presta |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0206246 A1 | 8/2008 | Ravetch et al. |
| 2008/0219952 A1 | 9/2008 | Fischer et al. |
| 2008/0226635 A1 | 9/2008 | Koll et al. |
| 2008/0227136 A1 | 9/2008 | Pla et al. |
| 2008/0254514 A1 | 10/2008 | Knudsen |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0069232 A1 | 3/2009 | Callewaert et al. |
| 2009/0110679 A1 | 4/2009 | Li et al. |
| 2009/0123378 A1 | 5/2009 | Wong et al. |
| 2009/0136525 A1 | 5/2009 | Gerngross et al. |
| 2009/0142828 A1 | 6/2009 | Bucciarelli et al. |
| 2009/0148513 A1 | 6/2009 | Fraunhofer et al. |
| 2009/0151023 A1 | 6/2009 | Kuvshinov et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0253174 A1 | 10/2009 | Serber et al. |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0004907 A1 | 1/2010 | Kidal et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0069617 A1 | 3/2010 | Gagnon |
| 2010/0113294 A1 | 5/2010 | Venkataraman et al. |
| 2010/0120094 A1 | 5/2010 | Johnsen et al. |
| 2010/0135987 A1 | 6/2010 | Hickman et al. |
| 2010/0136025 A1 | 6/2010 | Hickman et al. |
| 2010/0145029 A1 | 6/2010 | Gagnon |
| 2010/0151499 A1 | 6/2010 | Collins et al. |
| 2010/0160894 A1 | 6/2010 | Julian et al. |
| 2010/0167313 A1 | 7/2010 | Essig et al. |
| 2010/0172911 A1 | 7/2010 | Naso et al. |
| 2010/0189717 A1 | 7/2010 | Kim et al. |
| 2010/0221823 A1 | 9/2010 | McCoy et al. |
| 2010/0255013 A1 | 10/2010 | Presta |
| 2010/0256336 A1 | 10/2010 | Yuk et al. |
| 2010/0278808 A1 | 11/2010 | Ravetch et al. |
| 2010/0278822 A1 | 11/2010 | Fraunhofer et al. |
| 2010/0279306 A1 | 11/2010 | Bosques et al. |
| 2010/0291624 A1 | 11/2010 | Zhang et al. |
| 2010/0292443 A1 | 11/2010 | Sabbadini et al. |
| 2010/0297609 A1 | 11/2010 | Wells et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0039300 A1 | 2/2011 | Bayer et al. |
| 2011/0039729 A1 | 2/2011 | Delisa et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086050 A1 | 4/2011 | Presta |
| 2011/0086798 A1 | 4/2011 | Sethuraman et al. |
| 2011/0097336 A1 | 4/2011 | Wu et al. |
| 2011/0117601 A1 | 5/2011 | Haberger et al. |
| 2011/0123544 A1 | 5/2011 | Salfeld et al. |
| 2011/0124024 A1 | 5/2011 | Raju et al. |
| 2011/0129468 A1 | 6/2011 | Mccue et al. |
| 2011/0130544 A1 | 6/2011 | Ram et al. |
| 2011/0136682 A1 | 6/2011 | Bosques et al. |
| 2011/0171227 A1 | 7/2011 | Okun et al. |
| 2011/0207676 A1 | 8/2011 | Callewaert et al. |
| 2011/0213137 A1 | 9/2011 | Bosques et al. |
| 2011/0263828 A1 | 10/2011 | Wong et al. |
| 2011/0300151 A1 | 12/2011 | Okun et al. |
| 2011/0318340 A1 | 12/2011 | Collin et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0093810 A1 | 4/2012 | Takada et al. |
| 2012/0107783 A1 | 5/2012 | Julian et al. |
| 2012/0107874 A1 | 5/2012 | Liu et al. |
| 2012/0122076 A1 | 5/2012 | Lau et al. |
| 2012/0122759 A1 | 5/2012 | Brown et al. |
| 2012/0123688 A1 | 5/2012 | Ramasubramanyan et al. |
| 2012/0129185 A1 | 5/2012 | Maksymowych et al. |
| 2012/0134988 A1 | 5/2012 | Ravetch et al. |
| 2012/0171123 A1 | 7/2012 | Medich et al. |
| 2012/0177596 A1 | 7/2012 | Fischkoff et al. |
| 2012/0177640 A1 | 7/2012 | Burg et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0195885 A1 | 8/2012 | Correia et al. |
| 2012/0201831 A1 | 8/2012 | Salfeld et al. |
| 2012/0202974 A1 | 8/2012 | Eon-Duval et al. |
| 2012/0213792 A1 | 8/2012 | Salfeld et al. |
| 2012/0219564 A1 | 8/2012 | Salfeld et al. |
| 2012/0230913 A1 | 9/2012 | Johnston et al. |
| 2012/0238730 A1 | 9/2012 | Dong et al. |
| 2012/0244168 A1 | 9/2012 | Salfeld et al. |
| 2012/0251541 A1 | 10/2012 | Baurin et al. |
| 2012/0251550 A1 | 10/2012 | Borhani et al. |

(56) References Cited

U.S. PATENT DOCUMENTS

| | | |
|---|---|---|
| 2012/0258114 A1 | 10/2012 | Salfeld et al. |
| 2012/0258496 A1 | 10/2012 | Ellwanger et al. |
| 2012/0263731 A1 | 10/2012 | Fraunhofer et al. |
| 2012/0264920 A1 | 10/2012 | Wang et al. |
| 2012/0264927 A1 | 10/2012 | Parsons et al. |
| 2012/0271041 A1 | 10/2012 | Ficko Trcek |
| 2012/0276109 A1 | 11/2012 | Fraser et al. |
| 2012/0276134 A1 | 11/2012 | Fraser et al. |
| 2012/0276155 A1 | 11/2012 | Kishimoto et al. |
| 2012/0276157 A1 | 11/2012 | Fraser et al. |
| 2012/0276158 A1 | 11/2012 | Fraser et al. |
| 2012/0276160 A1 | 11/2012 | Maldonado |
| 2012/0276631 A1 | 11/2012 | Bengea et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2012/0308514 A1 | 12/2012 | Salfeld et al. |
| 2012/0309056 A1 | 12/2012 | Leon et al. |
| 2012/0329709 A1 | 12/2012 | Collins et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0149300 A1 | 6/2013 | Hiatt et al. |
| 2013/0156760 A1 | 6/2013 | Fraunhofer et al. |
| 2013/0189737 A1 | 7/2013 | Kang et al. |
| 2013/0195888 A1 | 8/2013 | Wang et al. |
| 2013/0205604 A1 | 8/2013 | Esenwein et al. |
| 2013/0231255 A1 | 9/2013 | Collins et al. |
| 2013/0243786 A1 | 9/2013 | Banerjee et al. |
| 2013/0244280 A1 | 9/2013 | Parikh et al. |
| 2013/0245139 A1 | 9/2013 | Kozlov et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0045212 A1 | 2/2014 | Bosques et al. |
| 2014/0046032 A1 | 2/2014 | Blanche et al. |
| 2014/0065710 A1 | 3/2014 | Rives et al. |
| 2014/0072585 A1 | 3/2014 | Herigstad et al. |
| 2014/0087423 A1 | 3/2014 | Koncilja et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0199340 A1 | 7/2014 | Maldonado |
| 2014/0199729 A1 | 7/2014 | Srivastava et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271622 A1 | 9/2014 | Prentice |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0273057 A1 | 9/2014 | Prentice et al. |
| 2014/0274911 A1 | 9/2014 | Collins et al. |
| 2014/0274912 A1 | 9/2014 | Prentice |
| 2014/0275494 A1 | 9/2014 | Wang et al. |
| 2014/0288272 A1 | 9/2014 | Allison et al. |
| 2014/0288278 A1 | 9/2014 | Nti-Gyabaah et al. |
| 2014/0296490 A1 | 10/2014 | Faid et al. |
| 2014/0301977 A1 | 10/2014 | Nadarajah et al. |
| 2014/0314745 A1 | 10/2014 | Rives et al. |
| 2014/0363845 A1 | 12/2014 | Sinacore et al. |
| 2014/0377275 A1 | 12/2014 | Neu et al. |
| 2015/0023977 A1 | 1/2015 | Fraunhofer et al. |
| 2015/0079102 A1 | 3/2015 | Wan et al. |
| 2015/0110775 A1 | 4/2015 | Subramanian et al. |
| 2015/0110799 A1 | 4/2015 | Ramasubramanyan et al. |
| 2015/0125905 A1 | 5/2015 | Pla et al. |
| 2015/0132320 A1 | 5/2015 | Chumsae et al. |
| 2015/0132801 A1 | 5/2015 | Ramasubramanyan et al. |
| 2015/0133639 A1 | 5/2015 | Wentz et al. |
| 2015/0139988 A1 | 5/2015 | Labkovsky et al. |
| 2015/0140006 A1 | 5/2015 | Ramasubramanyan et al. |
| 2015/0141632 A1 | 5/2015 | Markosyan |
| 2015/0158944 A1 | 6/2015 | Bengea et al. |
| 2015/0166653 A1* | 6/2015 | Wang .................. C07K 16/241 424/158.1 |
| 2015/0183865 A1 | 7/2015 | Rives et al. |
| 2015/0183866 A1 | 7/2015 | Rives et al. |
| 2015/0197579 A1 | 7/2015 | Stefan et al. |
| 2015/0210735 A1 | 7/2015 | Hickman et al. |
| 2015/0259410 A1 | 9/2015 | Ramasubramanyan et al. |
| 2015/0299249 A1 | 10/2015 | Herigstad et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328333 A1 | 11/2015 | Fraser et al. |
| 2015/0335762 A1 | 11/2015 | Fraser et al. |
| 2015/0344564 A1 | 12/2015 | Hickman et al. |
| 2015/0361169 A1 | 12/2015 | Wan et al. |
| 2015/0361170 A1 | 12/2015 | Fraunhofer et al. |
| 2016/0017030 A1 | 1/2016 | Neu et al. |
| 2016/0017281 A1 | 1/2016 | Sunstrom |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0039924 A1 | 2/2016 | Zeng |
| 2016/0039925 A1 | 2/2016 | Subramanian et al. |
| 2016/0046708 A1 | 2/2016 | Subramanian et al. |
| 2016/0068881 A1 | 3/2016 | Prentice |
| 2016/0083452 A1 | 3/2016 | Hickman et al. |
| 2016/0115193 A1 | 4/2016 | Herigstad et al. |
| 2016/0115195 A1 | 4/2016 | Mendiratta et al. |
| 2016/0122384 A1 | 5/2016 | Kim et al. |
| 2016/0138064 A1 | 5/2016 | Rives et al. |
| 2016/0145331 A1 | 5/2016 | Subramanian et al. |
| 2016/0159897 A1 | 6/2016 | Zeng |
| 2016/0185848 A1 | 6/2016 | Hossler et al. |
| 2016/0186130 A1 | 6/2016 | Pla et al. |
| 2016/0194390 A1 | 7/2016 | Ramasubramanyan et al. |
| 2016/0207922 A1 | 7/2016 | Tang et al. |
| 2016/0207992 A1 | 7/2016 | Bengea et al. |
| 2016/0215319 A1 | 7/2016 | Mendiratta et al. |
| 2016/0222101 A1 | 8/2016 | Fraunhofer et al. |
| 2016/0227381 A1 | 8/2016 | Bargetzi et al. |
| 2016/0237149 A1 | 8/2016 | Flikweert et al. |
| 2016/0237150 A1 | 8/2016 | Subramanian et al. |

FOREIGN PATENT DOCUMENTS

| | | |
|---|---|---|
| CN | 105777896 A | 7/2016 |
| CN | 105777904 A | 7/2016 |
| DE | 3631229 A1 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 230584 A1 | 8/1987 |
| EP | 0351789 A2 | 1/1990 |
| EP | 0366043 A1 | 5/1990 |
| EP | 374510 A1 | 6/1990 |

(56) References Cited

FOREIGN PATENT DOCUMENTS

| | | |
|---|---|---|
| EP | 453898 A2 | 10/1991 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 585705 A1 | 3/1994 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1176195 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1849862 A2 | 10/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2305712 A1 | 4/2011 |
| EP | 2357250 A2 | 8/2011 |
| EP | 2495307 A1 | 9/2012 |
| EP | 2500414 A1 | 9/2012 |
| EP | 2528002 A2 | 11/2012 |
| EP | 2574677 A1 | 4/2013 |
| EP | 3036254 A1 | 6/2016 |
| EP | 3036320 A1 | 6/2016 |
| GB | 2160530 A | 12/1985 |
| GB | 2279077 A | 12/1994 |
| IN | 2285/MUM/2013 A1 | 1/2015 |
| JP | 6-292592 | 10/1994 |
| JP | 7289288 A | 11/1995 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/04054 A1 | 4/1991 |
| WO | WO-91/09967 A1 | 7/1991 |
| WO | WO-92/01047 A1 | 1/1992 |
| WO | WO-92/11383 A1 | 7/1992 |
| WO | WO-92/16221 A1 | 10/1992 |
| WO | WO-92/16553 A1 | 10/1992 |
| WO | WO-92/17583 A1 | 10/1992 |
| WO | WO-93/06213 A1 | 4/1993 |
| WO | WO-93/11793 A1 | 6/1993 |
| WO | WO-94/02602 A1 | 2/1994 |
| WO | WO-94/08619 A1 | 4/1994 |
| WO | WO-94/20139 A1 | 9/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-97/04801 A1 | 2/1997 |
| WO | WO-97/13852 A1 | 4/1997 |
| WO | WO-97/29131 A1 | 8/1997 |
| WO | WO-98/08934 A1 | 3/1998 |
| WO | WO-98/23645 A1 | 6/1998 |
| WO | WO-98/24883 A2 | 6/1998 |
| WO | WO-98/24884 A1 | 6/1998 |
| WO | WO-98/24893 A2 | 6/1998 |
| WO | WO-98/50433 A2 | 11/1998 |
| WO | WO-98/56418 A1 | 12/1998 |
| WO | WO-98/58964 A1 | 12/1998 |
| WO | WO-99/22764 A1 | 5/1999 |
| WO | WO-99/32605 A1 | 7/1999 |
| WO | WO-99/54342 A1 | 10/1999 |
| WO | WO-99/57134 A1 | 11/1999 |
| WO | WO-99/57246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-02/076578 A1 | 10/2002 |
| WO | WO-02/094192 A2 | 11/2002 |
| WO | WO-02/101019 A2 | 12/2002 |
| WO | WO-03/046162 A2 | 6/2003 |
| WO | WO-03045995 A2 | 6/2003 |
| WO | WO-03/059935 A2 | 7/2003 |
| WO | WO-03/066662 A2 | 8/2003 |
| WO | WO-03/102132 A2 | 12/2003 |
| WO | WO-2004008100 A2 | 1/2004 |
| WO | WO-2004009776 A2 | 1/2004 |
| WO | WO-2004/026891 A2 | 4/2004 |
| WO | WO-2004/058944 A2 | 7/2004 |
| WO | WO-2004058800 A2 | 7/2004 |
| WO | WO-2004/076485 A1 | 9/2004 |
| WO | WO-2004/097006 A1 | 11/2004 |
| WO | WO-2005042569 A2 | 5/2005 |
| WO | WO-2005-062967 A2 | 7/2005 |
| WO | WO-2005/063813 A2 | 7/2005 |
| WO | WO-2005/082483 A1 | 9/2005 |
| WO | WO-2005100584 A2 | 10/2005 |
| WO | WO-2006/014683 A2 | 2/2006 |
| WO | WO-2006/026445 A1 | 3/2006 |
| WO | WO-2006/043895 A1 | 4/2006 |
| WO | WO-2006045438 A1 | 5/2006 |
| WO | WO-2006/099308 A2 | 9/2006 |
| WO | WO-2006/110277 A1 | 10/2006 |
| WO | WO-2007-005786 A2 | 1/2007 |
| WO | WO-2007/024743 A2 | 3/2007 |
| WO | WO-2007/055916 A2 | 5/2007 |
| WO | WO-2007/070315 A2 | 6/2007 |
| WO | WO-2007-077217 A2 | 7/2007 |
| WO | WO-2007/087384 A2 | 8/2007 |
| WO | WO-2007/117490 A2 | 10/2007 |
| WO | WO-2007/117505 A2 | 10/2007 |
| WO | WO-2008/008360 A1 | 1/2008 |
| WO | WO-2008/028686 A2 | 3/2008 |
| WO | WO-2008/033517 A2 | 3/2008 |
| WO | WO-2008-057240 A2 | 5/2008 |
| WO | WO-2008/057634 A2 | 5/2008 |
| WO | WO-2008068879 A1 | 6/2008 |
| WO | WO-2008/077545 A1 | 7/2008 |
| WO | WO-2008087184 A2 | 7/2008 |
| WO | WO-2008/128230 A1 | 10/2008 |
| WO | WO-2008121616 A2 | 10/2008 |
| WO | WO-2008135498 A2 | 11/2008 |
| WO | WO-2009/027041 A1 | 1/2009 |
| WO | WO-2009/017491 A1 | 2/2009 |
| WO | WO-2009023562 A2 | 2/2009 |
| WO | WO-2009058769 A1 | 5/2009 |
| WO | WO-2009/073569 A2 | 6/2009 |
| WO | WO-2009/079382 A1 | 6/2009 |
| WO | WO-2009135656 A1 | 11/2009 |
| WO | WO-2010-048183 A1 | 4/2010 |
| WO | WO-2010036443 A1 | 4/2010 |
| WO | WO-2010043703 A1 | 4/2010 |
| WO | WO-2010/080062 A1 | 7/2010 |
| WO | WO-2010/102114 A1 | 9/2010 |
| WO | WO-2010/111633 A2 | 9/2010 |
| WO | WO-2010122460 A1 | 10/2010 |
| WO | WO-2010/129469 A1 | 11/2010 |
| WO | WO-2010127069 A1 | 11/2010 |
| WO | WO-2010/136209 A1 | 12/2010 |
| WO | WO-2010/138502 A2 | 12/2010 |
| WO | WO-2010/141039 A1 | 12/2010 |
| WO | WO-2011005773 A2 | 1/2011 |

(56) References Cited

FOREIGN PATENT DOCUMENTS

| | | |
|---|---|---|
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |
| WO | WO-2011098526 A1 | 8/2011 |
| WO | WO-2011110598 A1 | 9/2011 |
| WO | WO-2011/133886 A2 | 10/2011 |
| WO | WO-2011127322 A1 | 10/2011 |
| WO | WO-2011133902 A2 | 10/2011 |
| WO | WO-2011134919 A2 | 11/2011 |
| WO | WO-2011134920 A1 | 11/2011 |
| WO | WO-2012/014183 A1 | 2/2012 |
| WO | WO-2012019160 A1 | 2/2012 |
| WO | WO-2012030512 A1 | 3/2012 |
| WO | WO-2012/046255 A2 | 4/2012 |
| WO | WO-2012050175 A1 | 4/2012 |
| WO | WO-2012051147 A1 | 4/2012 |
| WO | WO-2012/065072 A2 | 5/2012 |
| WO | WO-2012/068134 A1 | 5/2012 |
| WO | WO-2012062810 A2 | 5/2012 |
| WO | WO-2012/078376 A1 | 6/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013-011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013/021279 A2 | 2/2013 |
| WO | WO-2013-066707 A1 | 5/2013 |
| WO | WO-2013/067301 A1 | 5/2013 |
| WO | WO-2013/095966 A1 | 6/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-164837 A1 | 11/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |
| WO | WO-2013-186230 A1 | 12/2013 |
| WO | WO-2014/018747 A2 | 1/2014 |
| WO | WO-2014/039903 A2 | 3/2014 |
| WO | WO-2014/052360 A2 | 4/2014 |
| WO | WO-2014/096672 A1 | 6/2014 |
| WO | WO-2014/099636 A1 | 6/2014 |
| WO | WO-2014/125374 A2 | 8/2014 |
| WO | WO-2014-149935 A1 | 9/2014 |
| WO | WO-2014/150655 A1 | 9/2014 |
| WO | WO-2014/151878 A2 | 9/2014 |
| WO | WO-2014/158231 A1 | 10/2014 |
| WO | WO-2014/159488 A1 | 10/2014 |
| WO | WO-2014/159494 A1 | 10/2014 |
| WO | WO-2014/159499 A1 | 10/2014 |
| WO | WO-2014/179601 A2 | 11/2014 |
| WO | WO-2014-196780 A1 | 12/2014 |
| WO | WO-2014/207763 A1 | 12/2014 |
| WO | WO-2015/004679 A1 | 1/2015 |
| WO | WO-2015/007912 A1 | 1/2015 |
| WO | WO-2015/051293 A2 | 4/2015 |
| WO | WO-2015/073884 A2 | 5/2015 |
| WO | WO-2016/007764 A1 | 1/2016 |
| WO | WO-2016/102383 A1 | 6/2016 |

OTHER PUBLICATIONS

"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS, 28 pages.

"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS, 22 pages.

"Memorandum in Support of Centocor's Motion for Summary Judgment No. 4 that Claims Encompassing Non-recombinant Human Antibodies are Invalid for Failing to Meet the Requirements of 35 U.S.C. §112", dated Aug. 1, 2013 and submitted by defendant in Civil Action No. 09-40089-FDS, 21 pages.

"Memorandum in Support of Centocor's Motion No. 3 for Summary Judgment that the 394 and 031 Patents are Invalid for Under 35 U.S.C. § 102(f) for Failing to Name the Proper Inventors", dated Aug. 1, 2013 and submitted by defendant in Civil Action No. 09-40089-FDS, 13 pages.

"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS, 16 pages.

"Plaintiffs' Memorandum in Support of Their Motion for Partial Summary Judgment", dated Aug. 1, 2013 and submitted by plaintiff in Civil Action No. 09-40089-FDS, 49 pages.

"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS, 13 pages.

Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.

Abraham, E., et al., "Efficacy and Safety of Monoclonal Antibody to Human Tumor Necrosis Factor α in Patients with Sepsis Syndrome," *JAMA*, vol. 273(12):934-941 (1995).

Adams. et al., "Aggressive cutaneous T-cell lymphomas after TNFα blockade," J. Am. Acad. Dermatol 2004;51 :660-2.

Ahmed, M. U.et al.; N-(Carboxyethyl)lysine, a product of the chemical modification of proteins by methylglyoxal, increases with age in human lens proteins; Biochem. J. 1997, 324, 565-570.

Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.

Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.

Ahmed, N.; Thornalley, P. J.; Advanced glycation endproducts: what is their relevance to diabetic complications?; Diabetes, Obes. Metab. 2007, 9, 233-245.

Alfaro, J. F.; Chemo-Enzymatic Detection of Protein Isoaspartate Using Protein Isoaspartate Methyltransferase and Hydrazine Trapping; Anal. Chem. 2008, 80, 3882-3889.

Alfaro, J. F.; Synthesis of LuxS Inhibitors Targeting Bacterial Cell-Cell Communication; Org. Lett. 2004, 6, 3043-3046.

Altamirano, C., et al., "Strategies for fed batch cultivation of t-PA producing CHO cells: substitution of glucose and glutamine and rational design of culture medium", *J. Biotechn.* 110:171-179, 2004.

Andersen DC, The effect of cell-culture conditions on the oligosaccharide structures of secreted glycoproteins. Curr Opin Biotechnol. Oct. 1994;5(5):546-9.

Anonymous, "SACHEM Displacement Chromatography," Aug. 29, 2012, Retrieved from the internet: ://www.displacementchromatography.com>, retrieved on Jul. 30, 2014.

Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.

(56) References Cited

OTHER PUBLICATIONS

Averginos, Gab '04 Abstracts—GE Healthcare Life Sciences, "HUMIRA manufacturing: challenges and the path taken", France, Oct. 3-5, 2004, published 2005, pp. 14-16.
Avgerinos et al. (GAb '04 Abstracts—GE Healthcare Life Sciences, France Oct. 3-5, 2004, pp. 15-16 published 2005).
Awdeh, Z.L., A.R. Williamson, and B.A. Askonas, One cell-one immunoglobulin. Origin of limited heterogeneity of myeloma proteins. Biochem J, 1970. 116(2): p. 241-8.
Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.
Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.
Barbuto, J. et al. "Production of Neutralizing Antibodies to Tumor Necrosis Factor by Human Tumor-Infiltrating B Lymphocytes" *Proc. Am. Assoc. Cancer Res,*. 34:487, Abstr. 2904 (1993).
Barnes et al., "Stability of Protein Production from Recombinant Mammalian Cells," Biotechnology and Bioengineering, 81:6, Mar. 20, 2003, pp. 631-639.
BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf www.bdbiosciences.com/external_files/Doc_Recon_2.0/ab/others/Phytone_Soytone.pdf>), (last accessed Jan. 8, 2015), 4 pages.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Biblia, T.A. et al., "In Pursuit of the Optimal Fed-Batch Process for Monoclonal Antibody Production", Biotechnol. Prog 11(1):1-13, Jan.-Feb. 1995.
Birch, Jr. et al., "Antibody production", Adv. Drug Delivery Reviews 58:671-685, 2006.
Blaker, GJ, et al., "The Glucose, Insulin and Glutamine Requirements of Suspension Cultures of HeLa Cells in a Defined Culture Medium", J. Cell Sci. 9:529-537, 1971.
Biastoff, S.; et al.; Colorimetric Activity Measurement of a Recombinant Putrescine N-Methyltransferase from *Datura stramonium*; Planta Med. 2006, 72, 1136.
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.
Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.
Boswell et al. "Effects of Charge on Antibody Tissue Distribution and Pharmacokinetics" Bioconjugate Chem.(21) 2153-2163 (2010).
Boyle, P. et al. "A Novel Monoclonal Human IgM Autoantibody which Binds Recombinant Human and Mouse Tumor Necrosis Factor-α" *Cell. Immunol.*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brekke, O. et al., "Therapeutic Antibodies for Human Diseases at the Dawn of the Twenty-first Century," *Nature*, vol. 2:52-62 (2002).
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).

Bruggemann et al., "Production of human antibody repertoires in transgenic mice" Cur. Op. Biotechnol. ;455-458 (1997).
Bruggemann, M., Neuberger, M.S., "Strategies for expressing human antibody repertoires in transgenic mice," *Immunol. Today* 17:391-397 (1996).
Burteau et al. (In Vitro Cell Dev Biol—Animal, Jul. / Aug. 2003. 39-291-296).
Byun, et al. Archives of Biochemistry and Biophysics, "Transport of anti-IL-6 binding fragments into cartilage and the effects of injury," 532 (2013), pp. 15-22.
Cai B, et al. "C-Terminal Lysine Processing of Human Immunoglobulin G2 Heavy Chain In Vivo" Biotechnol. Bioeng. 2011;108: 404-412.
Cambridge Antibody Technology, advertisement of phage display services, Science vol. 253, No. 5018 (1991).
Carter et al., "Humanization of an anti-p185HER2 antibody for human cancer therapy," *Proc. Nat. Acad. Sci*89:4285-4289 (1992).
Chang KH, et al., "N-Acetylcysteine Increases the Biosynthesis of Recombinant EPO in Apoptotic Chinese Hamster Ovary Cells", Free Radic Res. 30(2):85-91, 1999.
Chang, T. & Wu, L., Methylglyoxal, oxidative street, and hypertension, Can. J. Physiol. Pharmacol. 84: 1229-1238 (2006).
Chaplen, F.W.R., et al., Effect of endogenous methylgiyoxal on Chinese hamster ovary celis grown in culture Cytotechnology 1996, vol. 22, Issue 1-3, Abstract and references, 6 pages.
Chaplen, F.W.R., Incidence and potential implications of the toxic metabolite methylglyoxal in cell culture: A review, Cytotechnology 26: 173-183, 1998.
Chaplen, FWR; A dissertation entitled Analysis of Methylglyoxal Metabolism in Mammalian Cell Culture; Univ. of Wisconsin-Madison 1996, 218 pages.
Charter, Edward A., "A New Process for the Separation and Purification of Egg Yolk; Antibodies," BASc., The University of British Columbia; A Thesis; Apr. 1993, 163 pages.
Chelius, D. et al.; Identification and Characterization of Deamidation Sites in the Conserved Regions of Human Immunoglobulin Gamma Antibodies, Anal. Chem. 2005, 77,6004-6011.
Choo et al. "High-level production of a monoclonal antibody in murine myeloma cells by perfusion culture using a gravity settler" Biotechnology Progress, vol. 23, No. 1, Jan. 1, 2007, 225-231.
Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).
Chua, FKF et al., "Hyper-stimulation of monoclonal antibody production by high osmolarity stress in eRDF medium", J. Biotechnology 37(3):265-275, Nov. 15, 1994.
Chumsae, C., et al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009. 81(15): p. 6449-57.
Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013(Dec. 3, 2013), pp. 11401-11409.
Chung et al., "Utilization of Lysozyme Charge Ladders to Examine the Effects of Protein Surface; Charqe Distribution on Bindinq Affinity in Ion Exchanqe Systems," Lanqmuir 26(2): 759-768 (2010).
Chung et al. "Cetuximab-induced anaphylaxis and IgE specific for galactose-a-1,3-galactose" NEJM 358:11, 1109-1117 (2008).
Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).
Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.

(56) References Cited

OTHER PUBLICATIONS

Cohen, J., et al., "Intersept: An international, multicenter, placebo-controlled trial of monoclonal anitbody to human tumor necrosis factor-α in patients with sepsis," *Crit Care Med*, vol. 24(9):1431-1440 (1996).
Cordoba, A.J., et al., Non-enzymatic hinge region fragmentation of antibodies in solution. Journal of Chromatography B, 2005. 818(2): p. 115-121.
Cox, J. et al. "A directory of human germ-line Vκ segments reveals a strong bias in their usage" *Eur. J. Immunol.*, 24(2):827-36 (1994).
Cromwell (GAB'04 Abstracts—GE Healthcare Life Sciences, Franc Oct. 3-5, 2004, pp. 17-18 published 2005).
Crowell, C.K., et al., Amino acid and manganese supplementation modulates the glycosylation state of erythropoietin in a CHO culture system. Biotechnology and bioengineering, Feb. 15, 2007; 96(3):538-549.
Dai, S.; An Integrated Proteomic Analysis of Major Isoaspartyl-Containing Proteins in the Urine of Wild Type and Protein LIsoaspartate O-Methyltransferase-Deficient Mice; Anal. Chem. 2013, 85, 2423-2430.
Daugherty, et al. Formulation and Delivery Issues for Monoclonal Antibody Therapeutics. Advanced Drug Delivery Reviews, 2006. vol. 58, pp. 686-706.
Davies et al., "Antibody VH domains as small recognition units." *Biotechnology*, 13:475-479 (1995).
Department of Surgery, University of Toronto, Annual Report (1998-1999)(348 pages).
DePhillips et al., "Determinants of protein retention characteristics on cation-exchange adsorbents,"; Journal of Chromatograph A, 933:57-72 (2001).
DeZongotita et al., "Phosphate feeding improves high-cell-concentration NS0 myeloma cell culture performance for monoclonal antibody production" Biotechnology and Bioengineering. 2000, 69: 566-576.
Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.
DIONEX Application Note 125 (Monitoring Protein Deamidation by Cation-Exchange Chromatography. 2009; pp. 1-7).
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).
Doring, E., "Identification and Characterization of a TNFa Antagonist Derived from a Monoclonal Antibody" (1994) *Mol. Immunol* .31(14): 1059-1067.
Du et al., "Chromatographic analysis of the acidic and basic species of recombinant monoclonal antibodies" *MAbs*, Sep.-Oct. 2012; 4(5):578-85.
Elliot et al., "Repeated therapy with monoclonal antibody to tumour necrosis factor α (cA2) in patients with rheumatoid arthritis" (1994) *Lancet*, 344:1125-1127.
Elliot, "Treatment of rheumatoid arthritis with chimeric monoclonal antibodies to tumor necrosis factor α" (1993) *Arthritis & Rheumatism*, 36(12):1681-1690.
Ellison, Jay W. et al., "The Nucleotide Sequence of a Human Immunoglobulin Cγ1 Gene," Nucleic Acids Research, vol. 10, No. 13 (1982), 9 pages.
Emery, P. "Adalimumab therapy: Clinical findings and implications for integration into clinical guidelines for rheumatoid arthritis." *Drugs of Today*, 41(3): p. 155-163. (2005).
Erbitux (cetuximab) label, Revised Aug. 2013, 8 pages.
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.
Ewert et al., "Biophysical Properties of Human Antibody Variable Domains," J. Mol. Biol. 324: 531-; 553 (2003).
Exhibit dated Aug. 1, 2013 and cited by defendant in Civil Action No. 09-40089-FDS providing the Jun. 23, 2009 trial transcript of the PM session in the matter of *Centocor, et al.* v. *Abbott Laboratories*, 50 pages.
Exhibit dated Aug. 1, 2013 and cited by defendant in Civil Action No. 09-40089-FDS providing the trial transcript in the matter of *Abbott Laboratories, et al.* v. *The Mathilda and Terrance Kennedy Institute*, S.D.N.Y., 90 pages.
Exhibit dated Aug. 1, 2013 and cited by plaintiff in Civil Action No. 09-40089-FDS providing excerpts from the File History of U.S. Appl. No. 12/578,487, 5 pages.
Exhibit dated Aug. 1, 2013 and cited by defendant in Civil Action No. 09-40089-FDS providing the Jun. 24, 2009 trial transcript of the AM session in the matter of *Centocor, et al.* v. *Abbott Laboratories*, E.D. TX., 42 pages.
Exhibit dated Aug. 1, 2013 and cited by defendant in Civil Action No. 09-40089-FDS providing the Sep. 20, 2012 Day 8 trial transcript in the matter of *Abbott* v. *Centocor Ortho Biotech Inc.*, D. MA., 71 pages.
Exhibit dated Aug. 1, 2013 and cited by plaintiff in Civil Action No. 09-40089-FDS providing Declaration by Jochen Salfeld, dated Jan. 17, 2013, 40 pages.
Fahrner et al., "Industrial purification of pharmaceutical antibodies: development, operation, and validation of chromatography processes" Biotechnology and Genetic Engineering Reviews, 18, 2001, pp. 301-327.
FDA Package insert for Adalimumab, Sep. 26, 2003, pp. 1-16.
Feldmann, "Anti-TNF-alpha Therapy of Rheumatoid Arthritis: What Have We Learned?" (2001) *Annu. Rev. Immunol.*, 19:163-196.
Figini, "In Vitro assembly of Repertoires of Antibody Chains on the Surface of Phage by Renaturation" (1994) *J. Mol. Biol.*, 239:68-78.
Fishwild et al., "High-avidity human IgG kappa monoclonal antibodies from a novel strain of minilocus transgenic mice" (1996) *Nature Biotechnology*, 14:845-851.
Fleisher B., Mechanism of glycosylation in the Golgi apparatus. J Histochem Cytochem, Aug. 1983; 31(8):1033-1040.
Folk et al., "Carboxypeptidase B, Purification and Characterization of the Porcine Enzyme," J. Biological Chem, 1960, 235:2272-2277.
Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.
Foote, J., "Antibody framework residues affecting the conformation of the hypervariable loops" (1992) *J. Mol .Biol.*, 224(2):487-499.
Freitag et al., "Displacement chromatography in biotechnological downstream processing," J. Chromatography, (1995) 691(1):101-112.
Gagnon et al., "A Systematic Approach to the Purification of Monoclonal Antibodies," *LC-GC* 11 (1):26-34 (1993).
Gagnon, P., "Polishing methods for monoclonal IgG purification" Chapter 17, Taylor & Francis Group, LLC, pp. 491-505, 2007.
Gatto, B. "Biologics targeted at TNF: design, production and challenges", Reumatismo 58(2):94-103, 2006.
Gauthier, M. A.& Klok, H.-A. Arginine-Specific Modification of Proteins with Polyethylene Glycol Biomacromolecules; 2011, 12, 482-493.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Genbank Entry for CHO Cathepsin L., EGW13555, Aug. 25, 2011, pp. 1-2.
Ghaderi, et al., "Implications of the Presence of N-glycolylneuraminic acid in Recombinant Therapeutic Glycoproteins", *Nature Biotechnology*, 28(8):863-868 (2010).

(56) References Cited

OTHER PUBLICATIONS

Ghaderi, et al., "Production platforms for biotherapeutic glycoproteins. Occurrence, impact, and challenges of non-human sialylation", *Biotechnology and Genetic Engineering Reviews*, 28:147-176 (2012).

Gonzalez et al. "Purification of Lactic Acid from Fermentation Broths by Ion-Exchange Resins" Ind. Eng. Chem. Res. 45:3243 (2006).

Goochee CF The Oligosaccharides of Glycoproteins: Bioprocess Factors Affecting Oligosaccharide Structure and their Effect on Glycoprotein Properties. Nature Biotechnology Dec. 1991 1346-1355.

Goswami et al., "Developments and Challenges for mAb-Based Therapeutics," *Antibodies*, 2:452-500, 2013.

Graf et al., "Ion exchange resins for the purification of monoclonal antibodies from animal cell culture" Bioseparation 4 (1) :7-20 (Feb. 1994). ;4 (1) :7-20 (Feb. 1994).

Gram et al., "In vitro selection and affinity maturation of antibodies from a naive combinatorial immunoglobulin library" (1992) *PNAS*, 89:3576-3580.

Gramer et al., "Glycosidase Activities of the 293 and NS0 Cell Lines, and of an Antibody-Producing Hybridoma Cell Line", *Biotechnology and Bioengineering*, 43:423-428 (1994).

Gramer M Jet Al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.

Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.

Green et al., "Antigen-specific human monoclonal antibodies from mice engineered with human IG heavy and light chain YACs" (1994) *Nature Genetics*, 7:13-21.

Griffiths et al., "Isolation of high affinity human antibodies directly from large synthetic repertoires" (1994) *EMBO J.*, 13:3245-3260.

Griffiths, "Human anti-self antibodies with high specificity from phage display libraries" (1993) *The EMBO J.* 12(2):725-34.

Grunberg, J. et al., "High-Yield Production of Recombinant Antibody Fragments in HEK-293 Cells Using Sodium Butyrate", BioTechniques 34(5):968-972, May 2003.

Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, 20 Jun. 1998, pp. 642-648.

Harding et al., "Class switching in human immunoglobulin transgenic mice" (1995) *Ann. NY Acad. Sci.*, 764:536-547.

Harlow and Lane, Antibodies A Laboratory Manual, Purification of Antibodies by using a; Deae-matrix (Batch), Storing and Purifying Antibodies; Chapter 8: 302-303 (1988).

Harlow et al., Eds ("Antibodies: A Laboratory Manual" 1988. Cold Spring Harbor Laboratory Press, Chapter 7, pp. 245, 247,and 253).

Harris, "Processing of C-terminal lysine and arginine residues of proteins isolated from mammalian cell culture" Journal of Chromatography, (1995) 705; 129-134.

Harris, R.J., et al., Identification of multiple sources of charge heterogeneity in a recombinant antibody. Journal of Chromatography B: Biomedical Sciences and Applications, 2001. 752(2): p. 233-245.

Harris, Reed J. et al., "Structural Characterization of a Recombinant CD4-IgG Hybrid Molecule," Eur. J. Biochem. 194:611-620 (1990).

Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).

Hawkins, "Selection of Phage Antibodies by Binding Affinity Mimicking Affinity Maturation" (1992) *J. Mol. Biol.*, 226:889-896.

Heidemann, R. et al., "The use of peptones as medium additives for the production of a recombinant therapeutic protein in high density perfusion cultures of mammalian cells", Cytotechnology 32:157-167, 2000.

Helms et al., "Destabilizing loop swaps in the CDRs of an immunoglobulin VL domain," Protein; Science 4:2073-2081 (1995).

Hiatt et al., "Characterization and Applications of Antibodies Produced in Plants", *Intern. Rev. Immunol.*, 10:139-152 (1993).

Hiatt et al., "Production of Antibodies in Transgenic Plants", *Nature*, 342:76-78 (1989).

Hillgren, A. et al., "Protection mechanism of Tween 80 during freeze-thawing of a model protein LDH," *International Journal of Pharmaceutics*, vol. 237:57-69 (2002).

Hills, A.E. et al., Metabolic control of recombinant monoclonal antibody N-glycosylation in GS-NS0 cells, Biotechnology and Bioengineering, Oct. 20, 2001; 75(2):239-251.

Hipkiss, A.; Can the beneficial effects of methionine restriction in rats be explained in part by decreased methylglyoxal generation resulting from suppressed carbohydrate metabolism?; Biogerontology 2012, 13, 633-636.

Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).

Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.

Holt, L. et al., "Domain antibodies: proteins for therapy," Trends in Biotechnology, vol. 21(11):484-490 (2003).

Hoogenboom et al., "By-passing immunisation : Human antibodies from synthetic repertoires of germline VH gene segments rearranged in vitro" (1992) *J. Mol. Biol.*, 227:381-388.

Hoogenboom, "Converting rodent into human antibodies by guided selection" (1996) *Antibody Engineering*, Oxford University Press, pp. 169-185.

Horvath et al: "Characterization of a Monoclonal Antibody Cell Culture Production Process Using a Quality by; Design Approach", Molecular Biotechnology, vol. 45, No. 3, Jul. 1, 2010, pp. 203-206.

Hossler et al., "Optimal and consistent protein glycosylation in mammalian cell culture", Glycobiology; (2009), 19(9):936-949.

Hossler et al.; "Improvement of mammalian cell culture performance through surfactant enabled concentrated feed media"; Biotechnology Progress; 29(4):1023-1033 (2013).

http://www.cygnustechnologies.com/product_detail/host-cell-protein-antibodies/anti-cho-h . . . CYGNUS Technologies, Anti-CHO HCP (Apr. 18, 2012), 1 page.

Huang et al. "Effects of anti-TNF monoclonal antibody infusion in patients with hairy cell leukaemia" (1992) *Br. J. Haematol.*, 81(2):231-234.

Huang, L., et al., In Vivo Deamidation Characterization of Monoclonal Antibody by LC/MS/MS. Analytical Chemistry, 2005. 77(5): p. 1432-1439.

HUMIRA (adalimumab) label, Revised Sep. 2013, 87 pages.

HUMIRA (adalimumab) prescribing information, Dec. 20, 2002, pp. 1-16.

Huse, "Generation of a large combinatorial library of the immunoglobulin repertoire in phage lambda" (1989) *Science*, 246:1275-81.

HyClone™ CDM4CHO Catalog listing (last accessed Nov. 17, 2014).

ICH Topic Q6B "Specifications:Test Procedures and Acceptance Criteria for Biotechnological/Biological Products," Sep. 1999, pp. 1-17.

International Preliminary Report on Patentability for Application No. PCT/US07/08359, dated Dec. 12, 2011, 5 pages.

International Preliminary Report on Patentability for Application No. PCT/US2011/060388, dated May 30, 2012, 9 pages.

International Preliminary Report on Patentability for Application No. PCT/US2013/031352 dated Nov. 25, 2014, pp. 1-10.

International Preliminary Report on Patentability for Application No. PCT/US2013/031365, dated Mar. 3, 2015, 9 pages.

(56) References Cited

OTHER PUBLICATIONS

International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041954, dated Nov. 25, 2014, pp. 1-14.
International Preliminary Report on Patentability for Application No. PCT/US2013/041958, dated Dec. 4, 2014, pp. 1-2.
International Search Report and Written Opinion for Application No. PCT/US2008/085066, dated May 12, 2009, 5 pages.
International Search Report and Written Opinion for Application No. PCT/US2010/033387, dated Aug. 7, 2012, 10 pages.
International Search Report and Written Opinion for Application No. PCT/US2013/031380, dated Feb. 5, 2014, 162 pages.
International Search Report and Written Opinion for Application No. PCT/US2013/041954, dated Dec. 17, 2013, 21 pages.
International Search Report and Written Opinion for Application No. PCT/US2013/041958, dated Dec. 17, 2013, 21 pages.
International Search Report and Written Opinion for Application No. PCT/US2013/065720, dated Dec. 16, 2013, 14 pages.
International Search Report and Written Opinion for Application No. PCT/US2013/065797, dated Nov. 26, 2013, 14 pages.
International Search Report and Written Opinion for PCT/US2012/035266, dated Feb. 7, 2013 (corresponds to U.S. Appl. No. 13/547,020), 4 pages.
International Search Report and Written Opinion from PCT/US2013/065749 dated Mar. 18, 2014, 18 pages.
International Search Report and Written Opinion from PCT/US2014/024151 dated Aug. 7, 2014, pp. 1-16.
International Search Report for Application No. PCT/IB03/04502, dated May 26, 2004, 6 pages.
International Search Report for Application No. PCT/US2011/060388 dated May 30, 2012, 6 pages.
International Search Report for Application No. PCT/US2013/031352, Dated Apr. 25, 2013, 6 pages.
International Search Report for Application No. PCT/US2013/031389, Dated Jun. 3, 2013, 4 pages.
International Search Report for Application No. PCT/US2013/031485, Dated Jun. 25, 2013, 4 pages.
International Search Report for Application No. PCT/US2013/031681, Dated Jun. 14, 2013, 6 pages.
International Search Report for Application No. PCT/US2014/026606, Dated Dec. 8, 2014, 8 pages.
International Search Report for Application No. PCT/US2014/026636, Dated Jul. 29, 2014, 5 pages.
International Search Report from PCT/US2014/024256 dated Jul. 30, 2014, pp. 1-15.
Invitation to Pay Additional Fees for International Application No. PCT/US2013/031380, Dated Nov. 28, 2013, 5 pages.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Jack, M.; Wright, D.; The Role of Advanced Glycation Endproducts and Glyoxalase I in Diabetic Peripheral Sensory Neuropathy; Transl. Res. 2012, 159, 355-365.
Jakobovits, A., "Production of fully human antibodies by transgenic mice" (1995) *Curr. Op. Biotechnol.*, 6:561-566.
Jakubowski, H., Protein N-homocysteinylation: implications for atherosclerosis. Biomedicine; Pharmacotherapy, 2001. 55(8): p. 443-447.
Jayapal, Karthik P., et al., "Recombinant Protein Therapeutics from CHO Cells—20 Years and Counting," CHO Consortium, SBE Special Section, 40-47 (2007).
Jayme et al.; "Media formulation options and manufacturing process controls to safeguard against introduction of animal origin contaminants in animal cell culture"; Cytotechnology; 33:27-36 (2000).
Jefferis, R., Glycosylation of Recombinant Antibody Therapeutics. Biotechnology Progress, 2005.21(1): p. 11-16.
Jespers, "Guiding the Selection of Human Antibodies from Phage Display Repertoires to a Single Epitope of an Antigen" (1994) *Bio/Technology*, 12:899-903.
Johnson et al., "Characterization of cathepsin L secreted by Sf21 insect cells", Archives of Biochemistry and Biophysics (2005), 444:7-14.
Johnson, K.A., et al., Cation exchange HPLC and mass spectrometry reveal C-terminal amidation of an IqG1 heavy chain. Analytical Biochemistry, 2007. 360(1): p. 75-83.
Kalyanpur, M., "Downstream Processing in the Biotechnology Industry" Molecular Biotechnology, vol. 22:87-98 (2002).
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Karampetsou et al., "TNF-αantagonists beyond approved indications: stories of success and prospects for the future", Q J Med (2010) 103:917-928.
Kaschak et al: "Characterization of the basic charge variants of a human IgGI: Effect of copper concentration in cell culture media", MABS, vol. 3, No. 6, Nov. 1, 2011, pp. 577-583.
Kazuaki F et al "Enhancment of productivity of recombinant a-amidating enzyme by low temperature culture" Cytotechnology 31:85-94, 1999.
Kempeni, "Update on D2E7: a fully human anti-tumour necrosis factor-alpha monoclonal antibody" (2000) *Ann. Rheum. Dis.*, 59(Suppl. I)144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624.
Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009 (Mar. 6, 2009), pp. 639-648.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Kingkeohoi, S., Analysis of methylglyoxal metabolism in CHO celis grown in culture, Cytotechnology (2005) 48:1-13.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatography, 266:3-21 (1983).
Kwon et al., "Production of lactic acid by *Lactobacillus rhamnosus* with vitamin-suppremented soybean hydrolysate", Enzyme Microb Technol. (2000), 26:209-215.
Lerner, "Antibodies without immunization" (1992) *Science*, 258:1313-1314.
Leusch, "Failure to demonstrate TNFα-specific autoantibodies in human sera by ELISA and Western blot" (1991) *J. Immunol. Methods*, 139:145-47.
Lewis, "Use of alanine scanning mutagenesis to improve the affinity of an anti gp120 (HIV) antibody" (1994) *J. Cell. Biochem.*, 18D:215.
Li, F. et al., "Current Therapeutic Antibody Production and Process Optimization" BioProcessing Journal, vol. 4(5):23-30 (2005).

(56) References Cited

OTHER PUBLICATIONS

Li, Feng, et al., "Cell Culture Processes for Monoclonal Antibody Production," mAbs 2:5, 466-479 (Sep.-Oct. 2010).
Lifely et al., "Glycosylation and Biological Activity of CAMPATH-1H Expressed in Different Cell Lines and Grown Under Different Culture Conditions", *Glycobiology*, 5(8):813-822 (1995).
Liu et al. "Recovery and purificaiton process development for monoclonal antibody production" MABS, 2(5), pp. 480-499 (2010).
Liu, H., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.
Liu, H., et al., Heterogeneity of monoclonal antibodies. Journal of Pharmaceutical Sciences, 2008. 97(7): p. 2426-2447.
Liu, M, et al.; Discovery of Undefined Protein Cross-Linking Chemistry: A Comprehensive Methodology Utilizing 18O-Labeling and Mass Spectrometry; Anal. Chem. 2013, 5900-5908.
Liu, M.et al.; Protein Isoaspartate Methyltransferase-Mediated 18O-Labeling of Isoaspartic Acid for Mass Spectrometry Analysis; Anal. Chem. 2011, 84, 1056-1062.
Lo, T.W. et al., Binding and modification of proteins by methylglyoxal under physiological conditions. A kinetic and mechanistic study with n. alpha-acetylarginine, N alpha-acetyilysine, and N alpha-acetyllysine, and bovine serum albumin, Dec. 23, 1994, The Journal of Biological Chemistry, 269, 32299-32305.
Logan, John S. "Transgenic Animals: Beyond 'Funny Milk'", *Current Opinion in Biotechnology*, 4:591-595 (1993).
Lonberg et al., "Antigen-specific human antibodies from mice comprising four distinct genetic modifications" (1994) *Nature*, 368:856-859.
Lonberg et al., "Human Antibodies from Transgenic Mice" (1995) *Int. Rev. Immunol.*, 13:65-93.
Low et al., "Mimicking Somatic Hypermutation: Affinity Maturation of Antibodies Displayed on Bacteriophage Using a Bacterial Mutator Strain" (1996) *J. Mol. Biol.*, 260:359-368.
Low, Nigel: thesis extract (1996) *Cambridge University*.
Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007 (Aug. 18, 2007), pp. 15-29.
Luo et al., "Understanding of C-terminal lysine variants in antibody production using mammalian cells" Abstract of papers, ACS, Anaheim, CA, US, Mar. 2011, 1 page.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012 (Jul. 2012), pp. 1061-1068.
Ma, et al., "Generation and Assembly of Secretory Antibodies in Plants", *Science*, 268:716-719 (1995).
Maeda, et al., "Analysis of Nonhuman N-Glycans as the Minor Constituents in Recombinant Monoclonal Antibody Pharmaceuticals", *Anal. Chem.*, 84:2373-2379 (2012).
Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".
Manning, M., et al., *Stability of Protein Pharmaceuticals: An Update*. Pharmaceutical Research, 2010.27(4): p. 544-575.
Marks et al., "Human antibody fragments specific for human blood group antigens from a phage display library" (1993) *Bio/Technology*, 11:1145-1150.
Marks et al., "Molecular evolution of proteins on filamentous phage. Mimicking the strategy of the immune system" (1992) *J. Biol. Chem.* 267:16007-16010.
Marks, "By-passing immunization: Human antibodies from V-gene libraries displayed on phage" (1991) *J. Mol. Biol.*, 222:581-597.
Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.
Marks, JD., "By-Passing Immunization: Building High Affinity Human Antibodies by Chain Shuffling" (1992) *Biotechnology*, 10:779-783.
Martin, A.C.R. "Accessing the Kabat antibody sequence database by computer" (1996)*PROTEINS: Structure, Function and Genetics*, 25:130-133.
Martinelle, K. et al., "Effect of different cell culture medium surfactants on cell growth and viability", Cells and Culture, Proceedings of the 20th ESACT Meeting v4 819-822, Jun. 17-20, 2007.
Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.
McAtee et al., "Isolation of monoclonal antibody charge variants by displacement chromatography," Current Protocols in Protein Science, 8.10-8.10.13, 2012.
Medynski, "Phage Display: All Dressed Up and Ready to Role" (1994) *Bio/Technology*, 12:1134-1136.
Mendez et al., "Functional transplant of megabase human immunoglobulin loci recapitulates human antibody response in mice" (1997) *Nature Genetics*, 15:146-156.
Meuwly, F. et al., "Conversion of a CHO cell culture process from perfusion to fed-batch technology without altering product quality", J.Biotechn. 123:106-116, 2006.
Miller et al., "Characterization of site-specific glycation during process development of a human therapeutic monoclonal antibody" Journal of Pharmaceutical Sciences, vol. 100, No. 7, Jul. 2011, 2543-2550.
Millipore, "Pellicon 2 Filters and Holders," 2003, pp. 1-8.
Mizuochi, T., et al., Structural and numerical variations of the carbohydrate moiety of immunoglobulin G. J Immunol, 1982. 129(5): p. 2016-20.
Moore, A., et al., "Effects of temperature shift on cell cycle, apoptosis and nucleotide pools in CHO cell batch cultures", Cytotechnology, 23:47-54, 1997.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.
Muller-Spath, et al., "Chromatographic Separation of Three Monoclonal Antibody Variants Using Multicolumn Countercurrent Solvent Gradient Purification (MCSGP)" Biotechnology and Bioengineering, vol. 100. No. 6 (2008), pp. 1166-1177.
Möller, Monoclonal antibodies to human tumor necrosis factor α: in vitro and vivo application (1990) *Cytokine*, 2(3):162-69.
Neuberger M. et al., "Mice perform a human repertoire" (1997) *Nature*, 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Ni, W.; Analysis of Isoaspartic Acid by Selective Proteolysis with Asp-N and Electron Transfer Dissociation Mass Spectrometry; Anal. Chem. 2010, 82,7485-7491.
Nilsson, "Antibody engineering" (1995) *Current Opinion in Structural Biology*, 5:450-456.
Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", *Nephron*, 72:599-603 (1996).
Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).

(56) References Cited

OTHER PUBLICATIONS

Oh, D-K. et al., "Increased erythritol production in fed-batch cultures of Torula sp. By controlling glucose concentration", J. Industrial Microb. & Biotechn. 26(4): 248-252, 2001.
Oh, et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.
Oh, SKW, et al., "Substantial Overproduction of Antibodies by Applying Osmotic Pressure and Sodium Butyrate", Biotechn. Bioengin. 42(5):601-610, 1993.
Osbourn, "From rodent reagents to human therapeutics using antibody guided selection" (2005) *Methods*, 36(1):61-68.
Ouellette, D.; Studies in serum support rapid formation of disulfide bond between unpaired cysteine residues in the VH domain of an immunoglobulin G1 molecule; Anal. Biochem. 2010, 397, 37.
Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.
Pacis, et al.: "Effects of cell culture conditions on antibody N-linked glycosylation—what affect high mannose 5 glycoform", Biotechnology and Bioengineering vol. 108, No. 10 Oct. 2011, pp. 2348-2358.
Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh RB N-glycosylation and the production of recombinant glycoproteins vol. 7, Issue 5, p. 117-122, May 1989 Trends in Biotechnology.
Parekh, R.B., et al., Association of rheumatoid arthritis and primary osteoarthritis with changes in the glycosylation pattern of total serum IgG. Nature, 1985. 316(6027): p. 452-7.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992 (Jan. 1, 1992), pp. 839-845.
PCT/US2013/069702 International Search Report & Written Opinion mailed Jan. 31, 2014, 13 pages.
Perchiacca et al., "Aggregation-resistance domain antibodies engineered with charged mutations; near the edges of the complementarity-determining regions," Protein Engineering Design & Selection, 25: 10 (591-601) 2012.
Perkins, M.; et. Al. Determination of the Origin of Charge Heterogeneity in a Murine Monoclonal Antibody; M. Pharm. Res. 2000, 17, 1110-1117.
Pietersz et al., "In vitro and in vivo Antitumor Activity of a Chimeric anti-CD19 Antibody", *Cancer Immunol. Immunother.*, 41:53-60 (1995).
Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996 (Oct. 1, 1996), pp. 189-200.
Potter et al., "Antibody Production in the Baculovirus Expression System", *Intern. Rev. Immunol.*, 10:103-112 (1993).
Poul et al., "Design of Cassette Baculovirus Vectors for the Production of Therapeutic Antibodies in Insect Cells", *Immunotechnology*, 1:189-196 (1995).
Quan, C., et al., A study in glycation of a therapeutic recombinant humanized monoclonal antibody: Where it is, how it got there, and how it affects charge-based behavior. Analytical Biochemistry, 2008.373(2): p. 179-191.
Queen, C., "A humanized antibody that binds to the interleukin 2 receptor" (1989) *Proc. Natl. Acad. Sci. USA*, 86(24):10029-10033.
Rabbani, N.; Thornalley, P. J.; Glyoxalase in diabetes, obesity and related disorders; Semin. Cell Dev. Biol. 2011, 22, 309-317.
Rader et al. "A phage display approach to rapid antibody humanization: Designed combinatorial V gene libraries" (1998) *Proc Natl Acad Sci USA*, 95:8910-8915.

Raju, TS. "Glycosylation Variations with Expression Systems and Their Impact on Biological Activity of Therapeutic Immunoglobulins", *BioProcess International.*, 44-53 (2003).
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011 (Jan. 25, 2011), pp. 317-323.
Reichert JM., et al., "Monoclonal antibody successes in the clinic", Nature Biotech. 23(9):1073-1078, 2005.
Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Rheinwald JG, et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in Yeast *Pichia pastoris*", Biotechnology, 13:255-260 (1995).
Riechmann, "Phage display and selection of a site-directed randomized single-chain antibody Fv fragment for its affinity improvement" (1993) *Biochemistry*, 32(34):8848-8855.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997 (Jan. 1, 1997), pp. 201-207.
Roy, B.M., et al., Toxic concentrations of exogenously supplied methy!glyoxal in hybridoma cell culture, Cytotechnology (2004) 46:97-107.
Rube et al., "Ewing's sarcoma and peripheral primitive neuroectodermal tumor cells produce large quantities of bioactive tumor necrosis factor-α (TNF-α) after radiation exposure", Int. J. Radiation Oncology Biol. Phys., (2003), vol. 56, No. 5, pp. 1414-1425.
Rudikoff et al., "Single amino acid substitution altering antigen-binding specificity" (1982) *Proc. Natl. Acad. Sci. USA*, 70:1979-1983.
Sakai et al.; "Use of nonionic surfactants for effective supply of phosphatidic acid in serum-free culture of Chinese hamster ovary cells"; Journal of Bioscience and Bioengineering; 92(3):256-261 (2001).
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) *Critical Reviews in Biotechnology*, 12:437-462.
Santora et al., "Characterization of recombinant human monoclonal tissue necrosis factor-alpha antibody using cation exchange HPLC and capillary isoelectric focusing," Analytical Biochemistry, (1999) 275:98-108.
Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.
Sargent (pp. 1-3, Internet Archive captured Aug. 28, 2013, http://cellculturedish.com/2012/01 /cho-cells-the-top-expressionsystem-of-best-selling-biologic-drugs/).
Sato et al, "Stimulation of monoclonal antibody production by human-human hybridoma cells with an elevated concentration of potassium or sodium phosphate in serum-free medium," Cytotechnology 2:63-67, 1989.

(56) References Cited

OTHER PUBLICATIONS

Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006 (Nov. 1, 2006), pp. 1161-1173.
Saxena, R. K. et al.; Microbial production and applications of 1 ,2-propanediol; Indian J. Microbiol. 2010,50,2-11.
Schiestl et al. "Acceptable changes in quality attributes of glycosylated biopharmaceuticals" Nature Biotechnology, 29(4), 310-312 (2011).
Schwieterman, "Immunosuppression in Combination with Monoclonal Antibodies" in Biologic Agents in Autoimmune Disease (Mar. 2-4, 1995), 9 pages.
Senczuk et al. "Hydrophobic interaction chromatography in dual salt system increases protein binding capacity" Biotechnology and Bioengineering, 103(5), 930-935 (2009).
Seresht et al., "The impact of phosphate scarcity on pharmaceutical protein production in *S. cerevisiae*: linking transcriptomic insights to phenotypic responses" Microbial Cell Factories. 2011, 10: 104.
Sheeley et al., "Characterization of Monoclonal Antibody Glycosylation: Comparison of Expression Systems and Identification of Terminal α-Linked Galactose", *Anal. Biochem.*, 247(1):102-110 (1997).
Sheikh et al., "Studies of the digestion of bradykinin, lysyl bradykinin, and kinin-degradation products by carboxypeptidases A, B, and N;". Biochemical Pharmacology. 1986, 35: 1957-1963.
Shen, Amy Y. et al., "Recombinant DNA Technology and Cell Line Development," from "Cell Culture Technology for Pharmaceutical and Cell-Based Therapies," CRC Press, 1995, 15-40.
Shih, "Effects of Anions on the Deamidation of Soy Protein". Journal of Food Science. 1991, 56: 452-454.
Shubert et al. "Comparison of ceramic hydroxy- and fluoroapatite versus Protein A/G-based resins in the isiolation of a recombinant human antibody from cell culture supernatant" J. Chromatography A, 114 (2007) 106-113.
Shukla et al., "Host cell protein clearance during protein a chromatography: development of an improved column wash step," Biotechnology Progress, (2008) 24(5):1115-1121.
Shukla et al., "Recent advances in large-scale production of monoclonal antibodies and related proteins," Trends in Biotechnology, (2010) 28(5):253-261.
Sigma Catalog "RPMI1640" (last accessed Jan. 22, 2015), 3 pages.
Sigma MSDS for RMPI1640 (last accessed Jan. 22, 2015), 6 pages.
Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.
Sundaram et al., "An innovative approach for the characterization of the isoforms of a monoclonal antibody product," Mabs, 3(6):505-512, 2011.
Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.
Takagi, M. et al., "The effect of osmolarity on metabolism and morphology in adhesion and suspension chinese hamster ovary cells producing tissue plasminogen activator", Cytochnology 32:171-179, 2000.
Tamura et al., "Structural correlates of an anticarcinoma antibody: identification of specificity-determining residues (SDRs) and development of a minimally immunogenic antibody variant by retention of SDFs only," *J. Immun*. (2000) 164:1432-1441.
Tan et al., "Expression and purification of a secreted functional mouse/human chimaeric antibody against bacterial endotoxin in baculovirus-infected insect cells", Biotechnol. Appl. Biochem. (1999), 30:59-64.
Taylor et al.,"Human immunoglobulin transgenes undergo rearrangement, somatic mutation and class switching in mice that lack endogenous IgM" (1994) *Int. Immunol.*, 6:579-591.

Teichmann, S. Declaration dated Dec. 17, 2010 from opposition proceedings in EP 0929578, 6 pages.
Tess database "HYCLONE" Trademark #76244963. Filing date Apr. 23, 2001. Live mark. Last accessed Jan. 21, 2015.
Tess database "HYCLONE" Trademark #85769283. Filing date Sep. 30, 2012. Live mark. Last accessed Jan. 21, 2015.
Tharmalingam et al.; "Pluronic Enhances the Robustness and Reduces the Cell Attachment of Mammalian Cells"; Molecular Biotechnology; 39(2):167-177 (2008).
The Kennedy Institute of Rheumatology, 1995 Annual Scientific Report, "Anti-TNF trials and studies of mechanisms of action".
The MW Calculator available at the Sequence Manipulation Suite (see /bioinformatics.org/sms2/index.html), downloaded Feb. 25, 2014, 2 pages.
The pI Calculator available at the Sequence Manipulation Suite (see //bioinformatics.org/sms2/index.html>) downloaded Feb. 25, 2014, p. 1).
The Statement on a Nonproprietary Name Adopted by the USAN Council for Adalimumab, p. 1, downloaded on May 19, 2011 from http://www.ama-assn.org/resources/doc/usan/adalimumab.doc. 1 page.
Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.
Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.
Tomiya et al., "Comparing N-glycan processing in mammalian cell lines to native and engineered; lepidopteran insect cell lines," Glycoconjuqate Journal 21 :343-360 (2004).
Tomlinson, "The repertoire of human germline VH sequences reveals about fifty groups of VH segments with different hypervariable loops" (1992) *J. Mol. Biol.*, 227:776-98.
Tomlinson, "The structural repertoire of the human Vk domain" (1995) *The EMBO J.*, 14(18):4628-38.
Tracey, "Tumor necrosis factor: A pleiotropic cytokine and therapeutic target" (1994) *Annu. Rev. Med.*, 45:491-503.
Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.
United States Food and Drug Administration (FDA) Biological Licensing Application File No. 125057 (Adalimumab) (Dec. 31, 2002) (Last Accessed Mar. 4, 2015 at www.fda.gov/Drugs/DevelopmentApprovalProcess/HowDrugsareDevelopedandApproved/ApprovalApplications/TherapeuticBiologicApplications/ucm080610.htm>), 1 page.
Vallee B et al. "The role of zinc in carboxypeptidase" The Journal of Biological Chemistry, (1960) 235, 1; 64-69.
Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).
Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.
Van Lent PL, et al. "The impact of protein size and charge on its retention in articular cartilage" J Rheumatol. Aug. 1987;14(4):798-805.
Varasteh et al. Optimization of Anti-Rh D Immunoglobulin Stability in the Lyphiliization Process. Iranian Journal of Basic Medical Sciences, Spring 2008, vol. 11, No. 1. pp. 55-61.
Vasilli, P. et al., The Pathophysiology of Tumor Necrosis Factors, Annu. Rev. Immunol. 10:411-452 (1992).

(56) References Cited

OTHER PUBLICATIONS

Vaughan, "Human antibodies by design" (1998) *Nature Biotechnology*, 16:535-539.
Vlasak, J. & Ionescu, R., *Heterogeneity of Monoclonal Antibodies Revealed by Charge-Sensitive Methods*. Current Pharmaceutical Biotechnology, 2008. 9(6): p. 468-481.
Wagner et al., "Antibodies generated from human immunoglobulin miniloci in transgenic mice" (1994) *Nucl. Acids Res*. 22:1389-1393.
Wagner et al., "The diversity of antigen-specific monoclonal antibodies from transgenic mice bearing human immunoglobulin gene miniloci" (1994) *Eur. J. Immunol*., 24:2672-2681.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.
Ward, "Binding activities of a repertoire of single immunoglobulin variable domains secreted from *Escherichia coli*" (1989) *Nature*, 341:544-546.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Wedemayer et al., "Structural insights into the evolution of an antibody combining site" (1997) *Science*, 276:1665-1669.
Wiendl et al., "Therapeutic Approaches in Multiple Sclerosis. Lessons from failed and interrupted treatment trials", BioDrugs. (2002), 16(3):183-200.
Williams et al., "Kinetic analysis by stopped-flow radiationless energy transfer studies: effect of anions on the activity of carboxypeptidase A". Biochemistry. 1986, 25, 94-100.
Williams, A. et al., Ion-Exchange Chromatography, Oct. 1998, Supplement 44, pp. 10-10-1-10-10-30.
Winter, "Humanized antibodies" (1993) *Immunol. Today*, 14(6):243-246.
Winter, "Making antibodies by phage display technology" (1994) *Annu. Rev. Immunol*., 12:433-455.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2,Oct. 1, 2010, pp. 321-336.
Worthington Biochemical Corporation, porcine pancreas carboxypeptidase B, one page, Feb. 25, 2012.
Wurm, FM, "Production of recombinant protein therapeutics in cultivated mammalian cells", Nature Biotechnology 22(11):1393-1398, 2004.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yigzaw et al., "Exploitation of the adsorptive properties of depth filters for host cell protein removal during monoclonal antibody purification," Biotechnology Progress, (2006) 22(1):288-296.
Yuk, I.H. et al., Controlling Glycation of Recombinant Antibody in Fed Batch Cell Cultures, Nov. 2011 , Biotechnology and Bioengineering, vol. 108, No. 11 pp. 2600-2610.
Yumioka et al., "Screening of effective column rinse solvent for Protein-A chromatography," Protein Expression and Purification, (2010) 70(2): 218-223.
Zang, T.; et al.; Chemical Methods for the Detection of Protein N-Homocysteinylation via Selective Reactions with Aldehydes; Anal. Chem. 2009, 81, 9065-9071.
Zatarain-Rios E and Mannik M, "Charge-charge interactions between articular cartilage and cationic antibodies, antigens, and immune complexes," Arthritis Rheum. Nov. 1987;30(1 1):1265-73.
Zhang et al., "Isolation and characterization of charge variants using cation exchange displacement chromatography," 1218(31): 5079-5086, 2011.

Zhang, B., et al., Unveiling a Glycation Hot Spot in a Recombinant Humanized Monoclonal Antibody. Analytical Chemistry, 2008. 80(7): p. 2379-2390.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.
Zou et al., "Dominant expression of a 1.3 Mb human Ig kappa locus replacing mouse light chain production" (1996) *FASEB J*., 10:1227-1232.
Gao et al. "Site-selective modifications of arginine residues in human hemoglobin induced by methylglyoxal." Biochemistry, 2006; pp. 15654-15660.
Mehta, et al. "Purifying therapeutic monoclonal antibodies," Chemical Engineering Progress; May 2008, 104, 5; pp. S14-S20.
Roe, S. "Separation Based on Structure" Chapter 4, § 5.2, In, Protein Purification Methods; A Practical Approach, Harries, et al. Sep. 1989, p. 203.
"Preliminary Data From Two Clinical Trials Demonstrate Abbott Laboratories' HUMIRA Improved Symptoms of Psoriatic Arthritis and Ankylosing Spondylitis" *PR Newswire* (2004).
*Abbott Laboratories Announces Positive Results of Phase II HUMIRA (R) (adalimumab) Study in Psoriasis*, P.R. Newswire. (2004).
Alessandri, L. et al., "Increased serum clearance of oligomannose species present on a human IgG1 molecule." *mAbs*, (2012), 4(4); 509-520.
Amersham Biosciences, *Antibody Purification Handbook* (2002).
An, Zhigiang editor, "Therapeutic Monoclonal Antibodies: From Bench to Clinic," 2009 edition, John Wiley & Sons, Hoboken, NJ, US, pp. 73-76, section 3.4.3.
Andersen et al., *Protein Glycosylation: Analysis, Characterization, and Engineering*, Encyclopedia of Industrial Biotechnology (2011).
Anumula et al., "Quantitative glycan profiling of normal human plasma derived immunoglobulin and its fragments Fab and FcO" (2012) J. Immunol. Methods, 382:167-176.
Arakawa et al., *Biotechnology applications of amino acids in protein purification and formulations*, Amino Acids, vol. 33, pp. 587-605 (2007).
Arend et al., "Inhibition of the production and effects of interleukins-1 and tumor necrosis factor α in rheumatoid arthritis" (1995) Arth. Rheum., 38(2):151-160.
Ashkenazi et al., "Immunoadhesins: An alternative to human monoclonal antibodies" (1995) Methods, 8(2): 104-115.
Avgerinos, *HUMIRA manufacturing: challenges and the path taken*, Extended Reports from the 3rd International Symposium on Downstream Processing of Genetically Engineered Antibodies and Related Molecules (Oct. 3-5, 2004).
Babcock et al., *Partial Replacement of Chemically Defined CHO Media with Plant-Derived Protein Hydrolysates*, in Proceedings of the 21st Annual Meeting of the European Society for Animal Cell Technology (ESACT), Dublin, Ireland, Jun. 7-10, 2009, pp. 295-298 (Springer Netherlands).
Babcock, James et al., "Partial Replacement of Chemically Defined Media with Plant-Derived Protein Hydrolysates," *BioPharm International*, vol. 23: 6. Jun. 2010, 6 pages.
Bandyopadhyay S., et al. Physicochemical and functional characterization of a biosimilar adalimumab ZRC-3197, Biosimilars, 2015;5, pp. 1-18.
Barb et al., "Branch-specific sialylation of IgG-Fc glycans by ST6Gal-I" Biochemistry, (2009) 48:9705-9707.

(56) References Cited

OTHER PUBLICATIONS

Bartelds et al., "Development of antidrug antibodies against adalimumab and association with disease activity and treatment failure during long-term follow-up" (2011) JAMA, 305(14):1460-1468.
Baynes et al., *Role of Arginine in the Stabilization of Proteins against Aggregation*, Biochemistry, vol. 44, pp. 4919-4925 (2005).
Bertolini et al., Stimulation of bone resorption and inhibition of bone formation in vitro by human tumour necrosis factors, (1986) Nature 319:516-518.
Bibila & Robinson, *In Pursuit of the Optimal Fed-Batch Process for Monoclonal Antibody Production*, Biotechnol. Prog., 11:1-13 (1995).
Bird et al. "Single-chain antigen-binding proteins." Science. (1988) 242:423-426.
Borys et al., *Ammonia Affects the Glycosylation Patterns of Recombinant Mouse Placental Lactogen-I by Chinese Hamster Ovary Cells in a pH-Dependent Manner*, Biotechnology and Bioengineering, 43:505-514 (1994).
Braun (2002), Anti-tumor necrosis factor a therapy for ankylosing spondylitis: international experience, Ann. Rheum. Dis. 61(Suppl. III):iii51-iii60.
Brock, Jonathan et al., "Detection and identification of arginine modifications on methylglyoxal-modified ribonuclease by mass spectrometric analysis," Journal of Mass Spectrometry, 2007; 42: 89-100.
Butler, *Animal cell cultures: recent achievements and perspectives in the production of biopharmaceuticals*, Appl. Microbiol. Biotechnol., 68: 283-291 (2005).
Butler, *Optimisation of the Cellular Metabolism of Glycosylation for Recombinant Proteins Produced by Mammalian Cell Systems*, Cytotechnology, 50:57-76 (2006).
Carpenter et al., Rational Design of Stable Protein Formulations: Theory and Practice, 101 pages, (2002).
Champion et al., *Defining Your Product Profile and Maintaining Control Over It, Part 2*, BioProcess Technical, vol. 3, pp. 52-57 (Sep. 2005).
Chen et al., *Effects of Elevated Ammonium on Glycosylation Gene Expression in CHO Cells*, Metabolic Engineering, 8:123-132 (2006).
Chun et al., *Usability of size-excluded fractions of soy protein hydrolysates for growth and viability of Chinese hamster ovary cells in protein-free suspension culture*, Bioresource Technology, 98:1000-1005 (2007).
Clincke et al. "Effect of iron sources on the glycosylation macroheterogeneity of human recombinant IFN-y produced by CHO cells during batch processes," BMC Proceedings (Nov. 22, 2011) 5(Suppl 8):P114, pp. 1-2.
Clincke et al. "Characterization of metalloprotease and serine protease activities in batch CHO cell cultures: control of human recombinant IFN-γ proteolysis by addition of iron citrate," BMC Proceedings (Nov. 22, 2011) 5(Suppl 8):P115, pp. 1-3.
Clinical trial No. NCT00085644 "Human Anti-tumor Necrosis Factor (TNF) Monoclonal Antibody Adalimumab in Subjects With Active Ankylosing Spondylitis (ATLAS)" (2004).
Clinical trial No. NCT00235105 "Adalimumab in Early Axial Spondyloarthritis (Without Radiological Sacroiliitis): Placebo Controlled Phase Over 3 Months Followed by a 9 Months Open Extension Phase" (2005).
Coffman et al., *High-Throughput Screening of Chromatographic Separations: 1. Method Development and Column Modeling*, Biotechnology & Bioengineering, 100:605-618 (2008).
Commercially Available HUMIRA product, approved by the FDA in Dec. 2002 and available in Jan. 2003.
CPMP Policy Statement on DNA and Host Cell Proteins (HCP) Impurities, Routine Testing versus Validation Studies, EMEA, Jun. 10, 1997.

Cromwell, *Avastin: highlights from development*, Extended Reports from the 3rd International Symposium on Downstream Processing of Genetically Engineered Antibodies and Related Molecules (Oct. 3-5, 2004).
Cruz et al., *Process development of a recombinant antibody/interleukin-2 fusion protein expressed in protein-free medium by BHK cells*, Journal of Biotechnology, 96:169-183 (2002).
Cumming, *Glycosylation of recombinant protein therapeutics: control and functional implications*, Glycobiology, 1(2):115-130 (1991).
Das et al., "Delivery of rapamycin-loaded nanoparticle down regulates ICAM-1 expression and maintains an immunosuppressive profile in human CD34+ progenitor-derived dendritic cells" (2008) J Biomed Mater Res A., 85(4):983-92.
Davis et al., Recombinant Human Tumor Necrosis Factor Receptor (Etanercept) for Treating Ankylosing Spondylitis, Arthritis & Rheumatism 48:3230-3236 (2003).
Del Val et al., *Towards the Implementation of Quality by Design to the Production of Therapeutic Monoclonal Antibodies with Desired Glycosylation Patterns*, American Institute of Chemical Engineers, Biotechnol. Prog., 26(6):1505-1527 (2010).
Drew, Berry et al., "The Effects of Media Formulations on the Biochemical Profile of IgG Expressed in Sp2/0 Cells as Measured by Cation Exchange HPLC," European Society of Animal Cell Technology Meeting Jan. 2007, Poster #1115, 1 page.
Eason et al., "Inhibition of the effects of Tnf in renal allograft recipients using recombinant human dimeric tumor necrosis factor receptors" (1995) Transplantation, 59(2):300-305.
Ebersbach et al., "Affilin-novel binding molecules based on human gamma-B-crystallin, an all beta-sheet protein" (2007) J. Mol. Biol., 372 (1): 172-85.
Elliot et al., "Randomised double-blind comparison of chimeric monoclonal antibody to tumour necrosis factor alpha (cA2) versus placebo in rheumatoid arthritis" (1994) Lancet, 344(8930):1105-1110.
Emea, *Avastin Scientific Discussion* (2005).
Endres, *Soy Protein Products Characteristics, Nutritional Aspects, and Utilization*, 2001 (AOCS Press, Champaign, Illinois).
Ertani et al., *Biostimulant activity of two protein hydrolyzates in the growth and nitrogen metabolism of maize seedlings*, J. Plant Nutr. Soil Sci., 000:1-8 (2009).
Espinosa-Gonzalez, *Hydrothermal treatment of oleaginous yeast for the recovery of free fatty acids for use in advanced biofuel production*, Journal of Biotechnology, 187:10-15 (2014).
Exposure Factors Handbook, U.S. Environmental Protection Agency (1997).
Extended European Search Report for Application No. 13877986.3. Dated Aug. 4, 2014, 11 pages.
Falconer et al., *Stabilization of a monoclonal antibody during purification and formulation by addition of basic amino acid excipients*, vol. 86, pp. 942-948 (2011).
Farnan et al., Multiproduct High-Resolution Monoclonal Antibody Charge Variant Separations by pH Gradient Ion-Exchange Chromatography, Analytical Chem., vol. 81, No. 21, pp. 8846-8857 (2009).
Fauchère et al., *Amino acid side chain parameters for correlation studies in biology and pharmacology*, Int. J. Peptide Res., vol. 32, pp. 269-278 (1988).
Fava et al., "Critical role of peripheral blood phagocytes and the involvement of complement in tumour necrosis factor enhancement of passive collagen-arthritis" (1993) Clin. Exp. Immunol., 94(2):261-266.
Felver et al., "Plasma tumor necrosis factor a predicts decreased long-term survival in severe alcoholic hepatitis" (1990) Alcohol. Clin. Exp. Res. 14(2):255-259.
Fernandes, "Demonstrating Comparability of Antibody Glycosylation during Biomanufacturing," European Biopharmaceutical Review. (2005) pp. 106-110.
Fietze et al., "Cytomegalovirus infection in transplant recipients the role of tumor necrosis factor" (1994) Transplantation, 58(6):675-680.

(56) References Cited

OTHER PUBLICATIONS

Follmam et al., Factorial screening of antibody purification processes using three chromatography steps without protein A, J. Chromatography A, vol. 1024, pp. 79-85 (2004).
Foong et al., *Anti-tumor necrosis factor-alpha-loaded microspheres as a prospective novel treatment for Crohn's disease fistulae*, Tissue Engineering, Part C: Methods, 16(5):855-64 (2010).
Franek et al., Plant Protein Hydrolysates: Preparation of Defined Peptide Fractions Promoting Growth and Production in Animal Cells Cultures, Biotech. Progress, 16:688-692 (2000).
FrieslandCampina Domo. *Product Data Sheet: Proyield Pea PCE808*. Paramus, NJ: Aug. 2011.
FrieslandCampina Domo. *Product Data Sheet: Proyield Soy SE70M-UF*. Paramus, NJ: Apr. 2011.
FrieslandCampina Domo. *Product Data Sheet: Proyield Wheat Wgesom-UF*. Paramus, NJ: Apr. 2011.
FrieslandCampina Domo. *Product Information Sheet: CNE50M-UF*. Zwolfe, NL: Jun. 2010.
Gagnon et al., Technology trends in antibody purification, J. Chromatography A., vol. 1221, pp. 57-70 (available online Oct. 2011).
Gawlitzek et al., *Ammonium Alters N-Glycan Structures of Recombinant TNFR-IgG: Degradative Versus Biosynthetic Mechanisms*, Biotechnology and Bioengineering, 68(6):637-646 (2000).
Gawlitzek et al., *Identification of Cell Culture Conditions to Control N-Glycosylation Site-Occupancy of Recombinant Glycoproteins Expressed in CHO cells*, 103:1164-1175 (2009).
Gibbs, *Production and Characterization of Bioactive Peptides from Soy Fermented Foods and Their Hydrolysates*, Dissertation, McGill University, Montreal Quebec (1999).
Gilar et al., "Characterization of glycoprotein digests with hydrophilic interaction chromatography and mass spectrometry" (2011) Analytical Biochem., 417:80-88.
Giroir et al., "Inhibition of tumor necrosis factor prevents myocardial dysfunction during burn shock" (1994) Am. J. Physiol., 267(1 Pt 2):H118-24.
Goetze, A. et al., "High-mannose glycans on the Fc region of therapeutic IgG antibodies increase serum clearance in humans." *Glycobiology* (2011), 21(7); 949-959.
Gong et al., *Fed-Batch Culture Optimization of a Growth-Associated Hybridoma Cell Line in Chemically Defined Protein-Free Media*, Cytotechnology, 52:25-38 (2006).
Goochee et al., *Environmental Effects on Protein Glycosylation*, Biotechnology, 8:421-427 (1990).
Goochee, C.F. "Bioprocess Factors Affecting Glycoprotein Oligosaccharide Structure." *Develop. Biol. Standard*, vol. 76 (1992). 95-104.
Gorfien et al., *Optimized Nutrient Additives for Fed-Batch Cultures*, BioPharm International, 16:34-40 (2003).
Grabulovski et al., "A Novel, Non-immunogenic Fyn SH3-derived Binding Protein with Tumor Vascular Targeting Properties" (2007) J Biol Chem 282, (5): 3196-3204.
Gramer et al. "Modulation of antibody galactosylation through feeding of uridine, manganese chloride, and galactose," Biotechnology and Bioengineering. (Jul. 1, 2011) 108(7):1591-1602.
Gross et al. "Involvement of various organs in the initial plasma clearance of differently glycosylated rat liver secretory proteins," Eur. J. Biochem. (1988) 173(3):653-659.
Grosvenor, Sally, "A New Era in Cell Culture Media Development," *BioPharm International*, Jul. 2012 vol. 25: 7, pp. 1-7.
Gu et al., *Influence of Primatone RL Supplementation on Sialylation of Recombinant Human Interferon-γ Produced by Chinese Hamster Ovary Cell Culture Using Serum-Free Media*, Biotechnology and Bioengineering, 56(4):353-360 (1997).
Guidance for Industry—Q6B Specifications: Test Procedures and Acceptance Criteria for Biotechnological / Biological Products, Aug. 1999.
Guile et al., "A rapid high-resolution high-performance liquid chromatographic method for separating glycan mixtures and analyzing oligosaccharide profiles" (1996) Anal Biochem., 240(2):210-26.

Guse et al., *Purification and analytical characterization of an anti-CD4 monoclonal antibody for human therapy*, J. of Chromatography A, 661:13-23 (1994).
Haddadi et al., "Delivery of rapamycin by PLGA nanoparticles enhances its suppressive activity on dendritic cells" (2008) J Biomed Mater Res A., 84A(4):885-98.
Haibel (2005) *Arthritis and Rheumatism* 64(Suppl. III):316.
Haibel et al. (2004) *Arthritis and Rheumatism* 50(9):S217-18.
Hansen et al., "The role of tumor necrosis factor-alpha in acute endotoxin-induced hepatotoxicity in ethanol-fed rats" (1994) Hepatology, 20(2):461-474.
Hansen et al., *Extra- and intracellular amino acid concentrations in continuous Chinese hamster ovary cell culture*, Appl. Microbiol. Biotechnol., 41:560-564 (1994).
Harris et al., *Current Trends in Monoclonal Antibody Development and Manufacturing*, Chapter 12, pp. 193-205 (2010).
Hayter et al, *Chinese hamster ovary cell growth and interferon production kinetics in stirred batch culture*, Applied Microbiol. Biotech., 34:559-564 (1991).
Heeneman et al., *The concentrations of glutamine and ammonia in commercially available cell culture media*, J. Immunological Methods, 166:85-91(1993).
Hober, et al. "Protein A chromatography for antibody purification", J. Chromatography B, vol. 848 (2007) pp. 40-47.
Hong et al., *Substitution of glutamine by glutamate enhances production and galactosylation of recombinant IgG in Chinese hamster ovary cells*, Applied Microbiol. Biotech., 88:869-876 (2010).
Hossler, Patrick et al., "Targeted Shifting of Protein Glycosylation Profiles in Mammalian Cell Culture through Media Supplementation of Cobalt." *J. Glycobiol* vol. 3; 1.(2014). 9 pages.
Huang et al., *Nitrogen metabolism of asparagine and glutamate in Vero cells studied by 1H/15N NMR spectroscopy*, Applied Microbiol. Biotech., 77:427-436 (2007).
Hussain et al., "Hepatic expression of tumour necrosis factor-alpha in chronic hepatitis B virus infection" (1994) J. Clin. Pathol., 47:1112-1115.
Huston et al. "Protein engineering of antibody binding sites: recovery of specific activity in an anti-digoxin single-chain Fv analogue produced in *Escherichia coli*," Proc. Natl. Acad. Sci. USA(1988) 85:5879-5883.
Indian Patent Office—IPAIRS application status for 2285/MUM/2013—Application not yet published. Document found on internet at ipindiaonline.gov/in/patentsearch/search/index.aspx. Last accessed Apr. 13, 2015.
International Conference on Harmonisation of Technical Requirements for Registration of Pharmaceuticals for Human Use, *Specifications: Test Procedures and Acceptance Criteria for Biotechnological / Biological Products Q6B*, Mar. 10, 1999.
International Preliminary Report on Patentability for Application No. PCT/US2013/031380, dated Sep. 15, 2015, 13 pages.
International Preliminary Report on Patentability for Application No. PCT/US2013/065720, dated Sep. 24, 2015, 8 pages.
International Preliminary Report on Patentability for Application No. PCT/US2013/065749 dated Sep. 15, 2015, 10 pages.
International Preliminary Report on Patentability for Application No. PCT/US2013/065797, dated Sep. 24, 2015, 8 pages.
International Preliminary Report on Patentability for Application No. PCT/US2013/069702, dated Sep. 15, 2015, 8 pages.
International Preliminary Report on Patentability for Application No. PCT/US2014/024151, dated Sep. 15, 2015, 9 pages.
International Preliminary Report on Patentability for Application No. PCT/US2014/024256, dated Sep. 15, 2015, pp. 1-9.
International Preliminary Report on Patentability for Application No. PCT/US2014/026606, dated Sep. 15, 2015, 13 pages.
International Preliminary Report on Patentability for Application No. PCT/US2014/026636, dated Sep. 15, 2015, 9 pages.
International Preliminary Report on Patentability for Application No. PCT/US2014/059127, dated Apr. 14, 2016, 15 pages.
International Preliminary Report on Patentability for Application No. PCT/US2014/065793, dated May 17, 2016, 13 pages.
International Search Report and Written Opinion for Application No. PCT/US2014/058991, completed Dec. 18, 2014, 15 pages.

(56) References Cited

OTHER PUBLICATIONS

International Search Report and Written Opinion for Application No. PCT/US2014/065793, dated Jul. 27, 2015, 20 pages.
International Search Report and Written Opinion from PCT/US2015/039773 dated Sep. 25, 2015, pp. 1-14.
International Search Report and Written Opinion from PCT/US2015/042846 dated Feb. 2, 2016, pp. 1-22.
International Search Report for Application No. PCT/US2015/038819 Dated Sep. 2, 2015, 12 pages.
International Search Report with Written Opinion corresponding to International Patent Application No. PCT/US2014/059127, mailed May 7, 2015, 21 pages.
Invitation to Pay Additional Fees for International Application No. PCT/US2014/058991, mailed Jan. 15, 2015, 6 pages.
Invitation to Pay Additional Fees for International Application No. PCT/US2014/059127, dated Jan. 15, 2015, 6 pages.
Invitation to Pay Additional Fees for International Application No. PCT/US2014/065793, dated May 4, 2015, 15 pages.
Jacob et al., Scale-up of Antibody Purification, Antibodies, vol. 1: Production & Purification, (2004).
Karnoup et al., *O-Linked glycosylation in maize-expressed human IgA1*, Glycobiology, 15(10):965-981 (2005).
Kaufman et al., "Amplification and expression of sequences cotransfected with a modular dihydrofolate reductase complementary dna gene" (1982) Mol. Biol., 159(4):601-621.
Kaufman et al., *Depletion of manganese within the secretory pathway inhibits O-linked glycosylation in mammalian cells*, Biochemistry, 33(33):9813-9 (1994).
Kelley et al., *Downstream Processing of Monoclonal Antibodies: Current Practices and Future Opportunities*, Process Scale Purification of Antibodies (2009).
Kim et al., *Glycosylation pattern of humanized IgG-like bispecific antibody produced by recombinant CHO cells*, Applied Microbiol. Biotech., 85:535-542 (2010).
Kipriyanov et al. "Recombinant single-chain Fv fragments carrying C-terminal cysteine residues: production of bivalent and biotinylated miniantibodies," Molecular Immunology, (1994) 31(14):1047-1058 F.
Kipriyanov et al., "Single-chain antibody streptavidin fusions: tetrameric bifunctional scFv-complexes with biotin binding activity and enhanced affinity to antigen," Human Antibodies and Hybridomas.(1995) 6(3):93-101.
Kobak, Osteonecrosis and monoarticular rheumatoid arthritis treated with intra-articular adalimumab, *S. Mod Rheumatol*, 18, 290-292, Feb. 20, 2008.
Koide et al., "Monobodies: antibody mimics based on the scaffold of the fibronectin type III domain" (2007), Methods Mol. Biol., 352: 95-109.
Konig et al., "Tumor necrosis factor α and interleukin-1 stimulate bone resorption in vivo as measured by urinary [3H] tetracycline excretion from prelabeled mice" (1988) J. Bone Miner. Res., 3(6):621-627.
Kramarczyk et al., *High-Throughput Screening of Chromatographic Separations: II. Hydrophobic Interaction*, 100: 708-720 (2008).
Krehenbrink et al., "Artificial Binding Proteins (Affitins) as Probes for Conformational Changes in Secretin PuID" (2008) J. Mol. Biol., 383 (5): 1058-68.
Kunkel et al., "Comparisons of the Glycosylation of a Monoclonal Antibody Produced under Nominally Identical Cell Culture Conditions in Two Different Bioreactors" (2000) Biotechnol. Prog., 16(3): 462-470.
Kunkel, Jeremy P., et al., "Dissolved oxygen concentration in serum-free continuous culture affects N-linked glycosylation of a monoclonal antibody," *Journal of Biotechnology*, 62 (1998), 55-71.
Kurano et al., *Growth behavior of Chinese hamster ovary cells in a compact loop bioreactor. 2. Effects of medium components and waste products*, J. Biotechnol., 15(1-2):113-128 (1990).
Lain et al., *Development of a High-Capacity MAb Capture Step Based on Cation-Exchange Chromatography*, BioProcess Int'l, vol. 7, pp. 26-34 (May 2009).

Lazar et al., *Matrix-assisted laser desorption/ionization mass spectrometry for the evaluation of the C-terminal lysine distributor of a recombinant monoclonal antibody*, Rapid Communications in Mass Spectrometry, vol. 18, pp. 239-244 (2004).
Leader et al., *Agalactosyl IgG in Aggregates from the Rheumatoid Joint*, Br. J. Rheumatol., 35:335-341 (1996).
Leavitt et al. "Impaired Intracellular Migration and Altered Solubility of Nonglycosylated Glycoproteins of Vesicular Stomatitis Virus and Sindbis Virus," J. Biol. Chem. (1977) 252 (24) :9018-9023.
Lerner et al., "Tumor necrosis factors α and β can stimulate bone resorption in cultured mouse calvariae by a Prostaglandin-independent mechanism" (1993) J. Bone Miner. Res., 8(2):147-155.
Lienqueo et al., *Mathematical correlations for predicating protein retention times in hydrophobic interaction chromatography*, 978:71-79 (2002).
Ling et al., *Analysis of Monoclonal Antibody Charge Heterogeneity Using Ion-Exchange Chromatography on a Fully Biocompatible HPLC System*, Dionex (2009).
Liu et al., "The significance of changes in serum tumour necrosis factor (TNF) activity in severely burned patients" (1994) Burns, 20(1):40-44.
Lobo-Alfonso et al., *Benefits and Limitations of Protein Hydrolysates as Components of Serum-Free Media for Animal Cell Culture Applications, Protein Hydrolysates in Serum Free Media*, GIBCO Cell Culture, Invitrogen Corporation, Grand Island, New York, Chapter 4:55-78 (2010).
Lowe et al. "A Genetic Approach to Mammalian Glycan Function," Annu. Rev. Biochem. (2003) 72:643-691.
Lu et al., *Recent Advancement in Application of Hydrophobic Interaction Chromatography for Aggregate Removal in Industrial Purification Process*, 10:427-433 (2009).
Lubinieki et al., *Comparability assessments of process and product changes made during development of two different monoclonal antibodies*, Biologicals, vol. 39, pp. 9-22 (2011).
Luksa et al., *Purification of human tumor necrosis factor by membrane chromatography*, J. Chromatography A, 661:161-168 (1994).
Lund et al., *Control of IgG/Fc Glycosylation: A Comparison of Oligosaccharides from Chimeric Human/Mouse and Mouse Subclass Immunoglobulin Gs*, Molecular Immunology, 30(8):741-748 (1993).
MacDonald et al., "Tumour necrosis factor-alpha and interferon-gamma production measured at the single cell level in normal and inflamed human intestine" (1990) Clin. Exp. Immunol, 81 (2):301-305.
Matsumoto et al., *Autoantibody Activity of IgG Rheumatoid Factor Increases with Decreasing Levels of Galactosylation and Sialylation*, J. Biochemistry, 128:621-628 (2000).
McCauley et al., "Altered cytokine production in black patients with keloids" (1992) J. Clin. Immunol., 12(4):300-308.
McClain et al., "Increased tumor necrosis factor production by monocytes in alcoholic hepatitis" (1989) Hepatology, 9(3):349-351.
McCue et al., *Effect of phenyl sepharose ligand density on protein monomer/aggregate purification and separation using hydrophobic interaction chromatography*, J. of Chromatography A, 1216:209-909 (2009).
McLeod, "Adalimumab, etanercept and infliximab for the treatment of ankylosing spondylitis: a systematic review and economic evaluation," *Health Technol. Assess*. 11(28):1-158 (2006).
Meert et al., *Characterization of Antibody Charge Heterogeneity Resolved by Preparative Immobilized pH Gradients*, Analytical Chem., vol. 82, pp. 3510-3518 (2010).
Melter et al., *Adsorption of monoclonal antibody variants on analytical cation-exchange resin*, J. Chromatography A, vol. 1154, pp. 121-131 (2007).
Millward et al. "Effect of constant and variable domain glycosylation on pharmacokinetics of therapeutic antibodies in mice," Biologicals.(2008) 36(1):41-47.
Mizrahi, *Primatone RL in mammalian cell culture media*, Biotechnol. Bioeng., 19:1557-1561 (1977).

(56) References Cited

OTHER PUBLICATIONS

Moller et al., "Monoclonal antibodies to human tumor necrosis factor α: In vitro and in vivo application" (1990) Cytokine 2(3):162-169.

Moloney and Haltiwanger, *The O-linked fucose glycosylation pathway: indentification and characterization of a uridien diphosphoglucose: fucose-β1,3-glucosyltransferase activity from Chinese hamster ovary cells*, Glycobiology, 9:679-87 (1999).

Morgan et al. "Designing Biobetter Monoclonal Antibody Therapeutics by Glycoengineering," International Pharmaceutical Industry. (2011) pp. 38-44.

Nixon et al., "Engineered protein inhibitors of proteases" (2006) Curr Opin Drug Discov Devel, 9(2): 261-8.

Nyberg et al., *Metabolic Effects on Recombinant Interferon-γ Glycosylation in Continuous Culture of Chinese Hamster Ovary Cells*, Biotech. Bioeng., 62(3):336-347 (1999).

Nygren et al., "Alternative binding proteins: affibody binding proteins developed from a small three-helix bundle scaffold" (2008) FEBS J., 275 (11): 2668-76.

Onda et al., *Reduction of the Nonspecific Animal Toxicity of Anti-Tac (Fv)-PE38 by Mutations in the Framework Regions of the Fv Which Lower the Isoelectric Point*, J. Immunology, vol. 163, pp. 6072-6077 (1999).

Pacesetter, Beckman Coulter Newsletter, vol. 3, Issue 1 (Apr. 1999).

Packer et al., "A general approach to desalting oligosaccharides released from glycoproteins" (1998) Glycoconj J., 15(8):737-47.

Proteus, "Protein A Antibody Purification Handbook," Pro-Chem Inc., 2005, pp. 1-52.

Raju et al. "Galactosylation variations in marketed therapeutic antibodies," MABS. (May 1, 2012) 4(3):385-391.

Raju et al., "Glycoengineering of Therapeutic Glycoproteins: In Vitro Galactosylation and Sialylation of Glycoproteins with Terminal N-Acetylglucosamine and Galactose Residues" (2001) Biochemistry, 40(30):8868-8876.

Raju, *Terminal sugars of Fc glycans influence antibody effector functions of IgGs*, Current Opinion in Immunology, 20:471-478 (2008).

Rankin et al., "The therapeutic effects of an engineered human anti-tumour necrosis factor alpha antibody(CDP571) in rheumatoid arthritis" (1995) Br. J. Rheumatol., 34:334-342.

Rao et al., *mAb Heterogeneity Characterization: MabPac Strong Cation-Exchanger Columns Designed to Extend Capabilities of mAb Analysis*, Tutorials (Mar. 15, 2011).

Rao et al., *Separation of Monoclonal Antibodies by Weak Cation-Exchange Chromatography Using ProPac and ProSwift Columns*, Dionex (available online 2010).

Rau "Adalimumab (a fully human anti-tumour necrosis factor alpha monoclonal antibody) in the treatment of active rheumatoid arthritis: the initial results of five trials" Ann Rheum Dis 2002,61 (Suppl II): ii70-ii73.

Remy et al., " Zinc-finger nucleases: A powerful tool for genetic engineering of animals" (2010) Transgenic Res., 19(3): 363-71.

Restelli, Veronica, et al., "The Effect of Dissolved Oxygen on the Production and the Glycosylation Profile of Recombinant Human Erythropoietin Produced From CHO Cells," Biotechnology and Bioengineering, vol. 94, No. 3, (2006) 481-494.

Rivinoja et al, *Elevated Golgi pH Impairs Terminal NL Glycosylation by Inducing Mislocalization of Golgi Glycosyltransferases*, J. Cell. Physiol., 220:144-154 (2009).

Robinson et al., *Characterization of a Recombinant Antibody Produced in the Course of a High Yield Fed-Batch Process*, Biotech. Bioeng., 44:727-735 (1994).

Rodriguez et al., *Enhanced Production of Monomeric Interferon-â by CHO Cells through the Control of Culture Conditions*, Biotechnol. Prog., 21:22-30 (2005).

Rosolem et al., *Manganese uptake and redistribution in soybean as affected by glyphosate*, Rev. Bras. Ciênc. Solo, 34:1915-1922 (2010).

Rouiller et al. "Effiect of hydrocortisone on the production and glycosylation of an Fc-Fusion protein in CHO cell cultures," Biotechnology Progress.(May 2012) 28(3):803-813.

Roy, Samar N. et al., "Secretion of Biologically Active Recombinant Fibrinogen by Yeast." *The Journal of Biological Chemistry*, vol. 270; 40 (1995). 23761-23767.

Rudd et al. "Glycosylation and the Immune System," Science. (2001) 291(5512):2370-2376.

Rudwaleit et al., Adalimumab is effective and well tolerated in treating patients with ankylosing spondylitis who have advanced spinal fusion, Rhematology; 48; 551-557 (2009).

Russell et al., "Targets for sepsis therapies: Tumor necrosis factor versus interleukin-1" (1993) Curr. Opin. Biotech., 4:714-721.

Santiago et al., "Targeted gene knockout in mammalian cells by using engineered zinc-finger nucleases" (2008) Proc. Natl. Acad. Sci. USA., 105(15):5809-14.

Santora et al., *Determination of Recombinant Monoclonal Antibodies and Noncovalent Antigen TNFα Trimer Using Q-TOF Mass Spectrometry*, Spectroscopy, 17(5):50-57 (2002).

Scales et al., "Hepatic ischemia/reperfusion injury: importance of oxidant/tumor necrosis factor interactions" (1994) Am. J. Physiol., 267 (6 Pt 1):G1122-1127.

Schenerman et al., *CMC Strategy Forum Report*, BioProcess Technical (2004).

Schlaeger E.-J., *The protein hydrolysate, Primatone RL, is a cost-effective multiple growth promoter of mammalian cell culture in serum-containing and serum-free media and displays anti-apoptosis properties*, J. Immunol. Meth., 194:191-199 (1996).

Scientific Discussion. Retrieved from the Internet: ema.europa.eu/dics/en_GB/document_library/EPAR_Sceintific_Discussion/human/00481/WC500050867.pdf, EMEA, 2004. Last accessed on Jun. 29, 2015, 25 pages.

Seo, Jin Seok, et al., "Effect of culture pH on recombinant antibody production by a new human cell line, F2N78, grown in suspension at 33.0° C. and 37.0° C.," *Appl. Microbiol Biotechnol.*, vol. 97 (2013). 5283-5291.

Serrick et al., "The early release of interleukin-2, tumor necrosis factor-alpha and interferon-gamma after ischemia reperfusion injury in the lung allograft" (1994) Transplantation, 58(11):1158-1162.

Shankar et al., "Evaluation of the role of second messenger systems in tumor necrosis factor-stimulated resorption of fetal rat limb bones" (1993) Bone, 14(6):871-876.

Sheffield Bioscience, Bio-Science Technical Manual: Supplements for cell culture, fermentation, and diagnostic media, 43 pages (2011).

Shen et al., *Characterization of yeastolate fractions that promote insect cell growth and recombinant protein production*, Cytotechnology, 54:25-34 (2007).

Sheron et al., "Increased production of tumour necrosis factor alpha in chronic hepatitis B virus infection" (1991) J. Hepatol., 12(2):241-245.

Shi et al., *Real Time Quantitative PCR as a Method to Evaluate Xenotropic Murine Leukemia Virus Removal During Pharmaceutical Protein Purification*, Biotechnology & Bioengineering, vol. 87, No. 7, pp. 884-896 (Sep. 2004).

Shibuya et al., "The elderberry (*Sambucus nigra* L.) bark lectin recognizes the Neu5Ac(alpha 2-6)Gal/GalNAc sequence"(1987) J. Biol. Chem., 262(4): 1596-1601.

Shields et al. "Lack of Fucose on Human IgGl N-Linked Oligosaccharide Improves Binding to Human FcγRIII and Antibody-dependent Cellular Toxicity," J. Biol. Chem. (2002) 277(30) :26733-26740.

Shim, H., "One target, different effects: a comparison of distinct therapeutic antibodies against the same targets." Experimental and Molecular Medicine, vol. 43, p. 539-549, Oct. 2011.

Shirato, Ken et al., "Hypoxic regulation of glycosylation via the N-acetylglucosamine cycle." J. Clin. Biochem. Nutr. vol. 48; 1 (2011). 20-25.

Shukla et al., *Downstream processing of monoclonal antibodies—Application of platfrom approaches*, J. of Chromatography B, 848:28-39 (2007).

(56) References Cited

OTHER PUBLICATIONS

Shukla et al., eds., *Process Scale Bioseparations for the Biopharmaceutical Industry*, (Taylor & Francis Group, Boca Raton FL) (2006).
Shukla et al., *Recent advances in large-scale production of monoclonal antibodies and related proteins*, Trends in Biotechnology, 28(5):253-261 (2010).
Shukla et al., *Strategies to Address Aggregation During Protein a Chromatography*, BioProcess International, 3:36-44 (2005).
Siemensma et al., Towards an Understanding of How Protein Hydrolysates Stimulate More Efficient Biosynthesis in Cultured Cells: *Protein Hydrolysates in Biotechnology,Bio-Science*, 36 pages (2010).
Silverman et al., "Multivalent avimer proteins evolved by exon shuffling of a family of human receptor domains" (2005) Nat. Biotechnol., 23 (12): 1556-61.
Skerra et al., "Alternative binding proteins: Anticalins—harnessing the structural plasticity of the lipocalin ligand pocket to engineer novel binding activities kerra" (2008) FEBS J., 275 (11): 2677-83.
Stumpp et al., "DARPins: A new generation of protein therapeutics" (2008) Drug Discov. Today, 13 (15-16): 695-701.
Sun et al., "Bowel necrosis induced by tumor necrosis factor in rats is mediated by platelet-activating factor" (1988) J. Clin. Invest., 81(5):1328-1331.
Suthanthiran et al., "Renal transplantation" (1994) New Engl. J. Med., 331(6):365-376.
Takashima et al., "Characterization of Mouse Sialyltransferase Genes: Their Evolution and Diversity" (2008) Biosci. Biotechnol. Biochem., 72(5):1155-1167.
Tang et al., *Conformational characterization of the charge variants of a human IgG1 monoclonal antibody using H/D exchange mass spectrometry*, mAbs, vol. 5, pp. 114-125 (2013).
Taylor et al. "A transgenic mouse that expresses a diversity of human sequence heavy and light chain immunoglobulins," Nucleic Acids Research,(1992) 20(23):6287-6295.
Tebbey, Paul W., et al., "Consistency of quality for the glycosylated monoclonal antibody Humira (adalimumab)," MAbs, Sep. 3, 2015;7(5); 805-11.
The Difference-Between, "Poly vs. Polyalcohol—What's the difference?" pp. 1-2, downloaded from http://the-difference-between.com/polyalcohol/polyol on Apr. 16, 2016.
Thiansilakul et al., *Compositions, functional properties and antioxidative activity of protein hydrolysates prepared from round scad (Decapterus maruadsi)*, Food Chemistry, 103:1385-1394 (2007).
Tian et al., *Spectroscopic evaluation of the stabilization of humanized monoclonal antibodies in amino acid formulations*, Int'l J. of Pharmaceutics, vol. 335, pp. 20-31 (2007).
To , et al., Hydrophobic interaction chromatography of proteins: I. The effects of protein and adsorbent properties on retention and recovery, J. of Chromatography A, 1141:191-205 (2007).
Tracey et al., "Shock and tissue injury induced by recombinant human cachectin" (1986) Science, 234(4775):470-474.
Tritsch et al., Spontaneous decomposition of glutamine in cell culture media, Experimental Cell Research, 28:360-364 (1962).
Tsubaki et al., *C-terminal modification of monoclonal antibody drugs: Amidated species as a general product0related substance*, Int'l J. Biological Macromolecules, vol. 52, pp. 139-147 (2013).
Tugcu et al., *Maximizing Productivity of Chromatography Steps for Purification of Monoclonal Antibodies*, vol. 99, No. 3, pp. 599-613 (available online Aug. 2007).
Urech, D.M. et al., Anti-inflammatory and cartilage-protecting effects of an intra-articularly injected anti-TNFa single-chain Fv antibody (ESBA105) designed for local therapeutic use, Ann Rheum Dis, 69, 443-449, Mar. 16, 2009.
Urlaub et al., "Isolation of Chinese hamster cell mutants deficient in dihydrofolate reductase activity" (1980) Proc. Natl. Acad. Sci. USA, 77:4216-4220.

Van der Heijde et al., Adalimumab effectively reduces the signs and symptoms of active ankylosing spondylitis in patients with total spinal ankylosis, Arthritis & Rheumatism 67:1218-1221 (2008).
Van der Heijde et al., Efficacy and Safety of Adalimumab in Patients with Ankylosing Spondylitis, Arthritis & Rheumatism 54:2136-46 (2006).
Van der Heijde et al., Efficacy and Safety of Infliximab in Patients with Ankylosing Spondylitis, Arthritis & Rheumatism 52:582-591 (2005).
Van Der Poll et al., "Activation of coagulation after administration of tumor necrosis factor to normal subjects" (1990) N. Engl. J. Med., 322(23):1622-1627.
Van Der Poll et al., "Comparison of the early dynamics of coagulation activation after injection of endotoxin and tumor necrosis factor in healthy humans" (1991) Prog. Clin. Biol. Res., 367:55-60.
Van Dulleman et al., "Treatment of Crohn's disease with anti-tumor necrosis factor chimeric monoclonal antibody (cA2)" (1995) Gastroenterology, 109(1):129-135.
Varki et al. Essentials of Glycobiology, 2nd edition, (1999) CSHL, Retrieved from the internet: ncbi.nlm.nih.gov/books/NBK1908/, 4 pages.
Wallick et al. "Glycosylation of a VH residue of a monoclonal antibody against alpha (1-6) dextran increases its affinity for antigen," J. Exp. Med.(1988) 168(3):1099-1109.
Walsh et al. "Effect of the carbohydrate moiety on the secondary structure of ?2-glycoprotein. I. Implications for the biosynthesis and folding of glycoproteins," Biochemistry. (1990) 29(26):6250-6257.
Wang et al., "The immobilized leukoagglutinin from the seeds of Maackia amurensis binds with high affinity to complex-type Asn-linked oligosaccharides containing terminal sialic acid-linked alpha-2,3 to penultimate galactose residues" (1988) J Biol. Chem., 263(10): 4576-4585.
Wang et al., *Antibody Structure, Instability and Formulation*, J. Pharm. Sci., vol. 96, No. 1, pp. 1-26 (2007).
Wang, Tina et al., "Exploring Post-translational Arginine Modification Using Chemically Synthesized Methylglyoxal Hydroimidazolones," *J. Am. Chem. Soc.*, 2012, 134, pp. 8958-8967.
Warnock et al., "In vitro galactosylation of human IgG at 1 kg scale using recombinant galactosyltransferase" (2005) Biotechnol. Bioeng., 92(7):831-842.
Wei et al., *Glyco-engineering of human IgG1-Fc through combined yeast expression and in vitro chemoenzymatic glycosylation*, National Institute of Health Public Access Author Manuscript, Biochemistry, 47(39):10294-10304 (2008).
Weikert et al., "Engineering Chinese hamster ovary cells to maximize sialic acid content of recombinant glycoproteins" (1999) Nature Biotechnology, 17(11): 1116-1121.
Weinstein et al., "Primary structure of beta-galactoside alpha 2,6-sialyltransferase. Conversion of membrane-bound enzyme to soluble forms by cleavage of the NH2-terminal signal anchor" (1987) J. Biol. Chem. 262(36):17735-17743.
Weitzhandler et al., *Protein variant separations by cation-exchange chromatography on tentacle-type polymeric stationary phases*, Proteomics, vol. 1, pp. 179-185 (2001).
Wong et al., *Impact of Dynamic Online Fed-Batch Strategies on Metabolism, Productivity and N-Glycosylation Quality in CHO Cell Cultures*, Biotechnol. Bioeng., 89(2):164-177 (2005).
Wyss, et al. "The structural role of sugars in glycoproteins," Curr. Opin. Biotechnol. (1996), 7(4); 409-416.
Xie et al., *High Cell Density and High Monoclonal Antibody Production Through Medium Design and Rational Control in a Bioreactor*, Biotechnol. Bioeng., 51:725-729 (1996).
Yang et al., *Effect of Ammonia on the Glycosylation of Human Recombinant Erythropoietin in Culture*, Biotech. Progress, 16:751-759 (2000).
Yao et al., "The potential etiologic role of tumor necrosis factor in mediating multiple organ dysfunction in rats following intestinal ischemia-reperfusion injury" (1995) Resuscitation, 29(2):157-168.
Zhang et al. "A novel function for selenium in biological system: Selenite as a highly effective iron carrier for Chinese hamster ovearly cell growth and monoclonal antibody production," Biotechnology and Bioengineering. (2006) 95(6):1188-1197.

(56) References Cited

OTHER PUBLICATIONS

Zhang et al., "CHO glycosylation mutants as potential host cells to produce therapeutic proteins with enhanced efficacy" (2013) Advances in Biochemical Engineering/Biotechnology, 131:63-87.
Zhang et al., *Mass Spectrometry for Structural Characterization of Therapeutic Antibodies*, Mass Spectrometry Reviews, 28:147- 176 (2009).
Zhang, F. et al., "The Effect of Dissolved Oxygen (DO) Concentration on the Glycosylation of Recombinant Protein Produced by the Insect Cell-Baculovirus Expression System." *Biotechnology and Bioengineering*, (2002), 77(2); 219-224.
Zhang, Y. et al., "Specificity and Mechanism of Metal Ion Activation in UDP-galactose: β-Galactoside-α-1,3-galactosyltransferase." *J. Biological Chemistry* vol. 276; 15 (2001). 11567-11574.
Zhang, Y. et al., *Effects of peptone on hybridoma growth and monoclonal antibody formation*, Cytotechnology, 16:147-150 (1994).
Zhou, *Implementation of Advanced Technologies in Commercial MonoclonalAntibody Production, Biotech. J.*, 3:1185-1200 (2008).
Zhu, *Mammalian cell protein expression for biopharmaceutical production*, Biotech.Adv., 30:1158-1170 (2012).
U.S. Appl. No. 14/195,588.
U.S. Appl. No. 15/187,425.
U.S. Appl. No. 15/175,752.
U.S. Appl. No. 62/020,764.
U.S. Appl. No. 15/198,696.

\* cited by examiner

PROTEIN PURIFICATION USING DISPLACEMENT CHROMATOGRAPHY

This application is a continuation application of U.S. application Ser. No. 13/803,808, filed Mar. 14, 2013. The entire contents of the foregoing application are expressly incorporated herein by reference.

1. BACKGROUND OF THE INVENTION

The large-scale, economic purification of proteins continues to present challenges for the biopharmaceutical industry. Therapeutic proteins are typically produced using engineered prokaryotic or eukaryotic cell lines to express proteins of interest from a recombinant plasmid containing the gene encoding the protein. The cell culture processes used for producing those therapeutic proteins are known to produce proteins with varying degree of heterogeneity with respect to process-related impurities and product-related substances. Product-related substances typically include charge variants, aggregates, fragments, or other protein product species derived from alternative post-translational modifications. Process-related impurities include, for example, host cell proteins (HCPs), DNA, endotoxin, virus and cell culture media components. Control over such process-related impurities and product-related substances can impact numerous product characteristics, including, but not limited to, product stability, product safety and product efficacy.

Although various techniques are available for large-scale protein purification, the separation of product-related substances, including charge variant species, remains challenging. For example, the charge variants in monoclonal antibody preparations typically include acidic, main and basic species, which can be detected by WCX-10 HPLC (a weak cation exchange chromatography) or IEF (isoelectric focusing). The very similar physio-chemical characteristics between the main protein species and the acidic and basic variant species require the use of highly selective separation systems and methods in order to achieve efficient separation.

Displacement chromatography is a chromatographic separation technology that involves the use of a displacer molecule to aid in the separation of a mixture, e.g., an antibody-containing solution derived from cell culture harvest. The displacer molecule is conventionally selected to have a higher affinity for the stationary phase (i.e., the chromatographic support) as compared to the components present in the material to be separated. Due to its higher affinity, the displacer molecule competes with protein mixture components for the binding sites on the stationary phase. Under appropriate conditions, the displacer induces the components of the mixture to develop into consecutive zones of concentrated and purified species in the order of decreasing binding affinity ahead of the displacer front. This ordered displacement of the components of the mixture results in the formation of a so-called "displacement train." In contrast to traditional elution mode chromatography, the displacement process takes advantage of the nonlinearity of the adsorption isotherm, allowing for higher column loading levels without compromising the purity and recovery of the component of interest. Finally, washing of the displacement train with the displacing buffer from the column allows for the component of interest to be isolated by collecting (and pooling if necessary) the proper fraction(s) of the displaced eluate. Displacement chromatography in described, in general, in Brgles et al., Journal of Chromatography A, 1218 (2011) 2389-2395; Gajdosik et al., Journal of Chromatography A, 1239 (2012) 1-9; Gerstner et al., Biotechnol. Prog., (1992), 8, 540-545; Kundu et al., Analytical Biochemistry, 248, 111-116, (1997); and Vogt et al., Journal of Chromatography A, 760 (1997) 125-137.

2. SUMMARY OF THE INVENTION

The present invention is directed to compositions and methods that control (modulate or reduce) process-related impurity and product-related substance heterogeneity in a population of proteins.

In certain embodiments, the instant invention is directed to methods and compositions for producing a sample comprising a protein of interest wherein the process-related impurity and product-related substance heterogeneity is modulated or reduced. In certain embodiments the product-related substances include, but are not limited to charge variants. Such charge variants can be acidic species (also referred to herein as "acidic regions" and "AR") or basic species. In certain embodiments, the basic species are antibody species having C-terminal Lysines on both heavy chain sequences ("Lys 2") or antibody species having a C-terminal Lysine on one heavy chain sequence ("Lys 1"), and such basic species can be contrasted with antibody species having no C-terminal Lysines ("Lys 0"). In certain embodiments, such methods comprise: (a) contacting a sample comprising the protein of interest and at least one process-related impurity and/or product-related substance to a chromatography media under conditions wherein the protein of interest binds to the chromatography media; (b) displacing the protein of interest bound to the chromatography media with at least one displacer molecule; and (c) collecting a chromatography sample, wherein the chromatography sample comprises a reduced heterogeneity of the distribution of process-related impurities and product-related substances. In certain embodiments, the chromatography media is selected from the group consisting of an ion exchange adsorbent material, e.g., a cation exchange (CEX) adsorbent material or an anion exchange (AEX) adsorbent material, and a multimodal adsorbent material, or a combination thereof. In certain embodiments of the present invention, the CEX resin is the Poros XS resin. In certain embodiments of the present invention, the mixed mode resin is the Capto MMC resin.

In certain embodiments of the present invention, the pH of the displacing wash buffer is lower than the isoelectric point of the protein of interest. In certain embodiments of the present invention, the pH of the displacing wash buffer is in the range of about 5.0 to about 9.0 or about 6.0 to about 8.0. In certain embodiments of the present invention, the conductivity of the wash buffer is between about 1 to about 86 mS/cm. In certain embodiments of the present invention, the conductivity of the wash buffer is in the range of about 2 to about 20 mS/cm. In certain embodiments of the present invention, the column length is in the range of about 10 to about 30 cm. In certain embodiments of the present invention, the flow residence time is in the range of about 5 minutes to about 20 minutes.

In certain embodiments of the present invention, the displacer in the wash buffer carries positive charge. In certain embodiments of the present invention, the cationic displacer in the wash buffer is a quaternary ammonium salt. In certain embodiments of the present invention, the quaternary ammonium salt is Expell SP1™. In certain embodiments of the present invention, the cationic displacer in the wash buffer is protamine sulfate. In certain embodiments of the present invention, the concentration of the displacer in the wash buffer is greater than about 0.1 mM. In certain embodiments of the present invention, the concentration of the Expell SP1™ in the wash buffer is in the range of about 0.1 to about 10 mM. In certain embodiments of the present invention, the concentration of the protamine sulfate in the wash buffer is in the range of about 0.1 to about 5 mM.

In certain embodiments of the present invention, one displacer buffer is used. In certain embodiments of the present invention, two or more displacing buffers consisting of different displacer concentrations are used. In certain embodiments of the present invention, the first displacing buffer containing about 0.5 mM Expell SP1™. In certain embodiments of the present invention, the first displacing buffer containing about 0.25 mM protamine sulfate. In certain embodiments of the present invention, two or more displacing buffers consisting of different displacer concentrations are used and the first displacing buffer contains lower displacer concentration than the second or subsequent displacing buffer. In certain embodiments of the present invention, mixtures of two or more displacers are used. In certain embodiments the displacers can be at the same or different concentrations. In certain embodiments of the present invention, different displacers are used in each of the multi-step displacing buffer for separation.

In certain embodiments of the present invention, the displacement operation is run in one-step displacement chromatography mode. In certain embodiments of the present invention, the displacement operation is run in two-step displacement chromatography mode. In certain embodiments of the present invention, the displacement operation is run in multiple-step displacement chromatography mode. In certain embodiments of the present invention, the displacement operation is run in linear gradient displacement chromatography mode.

In certain embodiments, displacement chromatography is used as the sole method of purification of the protein of interest. In certain embodiments, displacement chromatography is used in combination with other purification strategies, such as, but not limited to, the alternative techniques described herein, to reduce process-related impurities and/or other product-related substances.

In certain embodiments, fractions are collected during the displacement step and are combined (pooled) after appropriate analysis to provide a protein preparation that contains a desired level of the protein of interest and which can include one or more process-related impurities and/or other product-related substances. In certain embodiments, one or more process monitoring tools can be used in connection with the techniques described herein to facilitate the identification of an effective product pooling strategy. In certain embodiments, such monitoring can include on-line or in-line process monitoring. For example, but not by way of limitation, spectroscopy methods such as UV, NIR, FTIR, Fluorescence, and Raman may be used to monitor levels of product-related species, e.g., acidic species and lysine variants, in an on-line, at line or in-line mode. In certain embodiments, specific signals arising from the chemical modification of the proteins such as glycation, MGO modification, deamidation, glycosylation may be specifically measurable by spectroscopic methods through such in-line, on-line or at-line methods, enabling real time or near-real time control of product quality of the resulting product.

In certain embodiments, purification and/or pooling allows for the reduction of process-related impurities and/or other product-related substances. In certain embodiments, the purification and/or pooling techniques described herein allow for reduction of process-related impurities and the selective inclusion of particular product-related substances. For example, but not by way of limitation, the purification and/or pooling techniques allow for modulation of the concentration of product-related substances in the purified sample, e.g., increasing or decreasing the amount of acidic and/or basic species. In certain embodiments, the concentration of particular acidic and/or basic species, e.g., Lys0, Lys 1, and/or Lys2, are modulated (increased or decreased) in the purified sample. In certain embodiments, such techniques can be used to ensure product uniformity over the course of multiple production runs.

In certain embodiments of the present invention, the chromatography separation produces samples containing reduced level of acidic species as compared to the starting load material. In certain embodiments of the present invention, the chromatography separation produces samples containing reduced level of protein aggregates as compared to the starting load material. In certain embodiments of the present invention, the chromatography separation produces samples containing reduced level of protein fragments as compared to the starting load material. In certain embodiments of the present invention, the chromatography separation produces samples containing reduced level of host cell proteins as compared to the starting load material. In certain embodiments of the present invention, the chromatography separation produces samples containing different levels of basic variants from the starting load material. In certain embodiments of the present invention, the chromatography separation produces samples containing reduced levels of acidic variants, aggregates, fragments and HCPs from the starting load material.

In certain embodiments of the present invention, the protein of interest is an anti-TNFα antibody, such as Adalimumab.

3. BRIEF DESCRIPTIONS OF THE DRAWINGS

4. DETAILED DESCRIPTION OF THE INVENTION

Figure 1A:
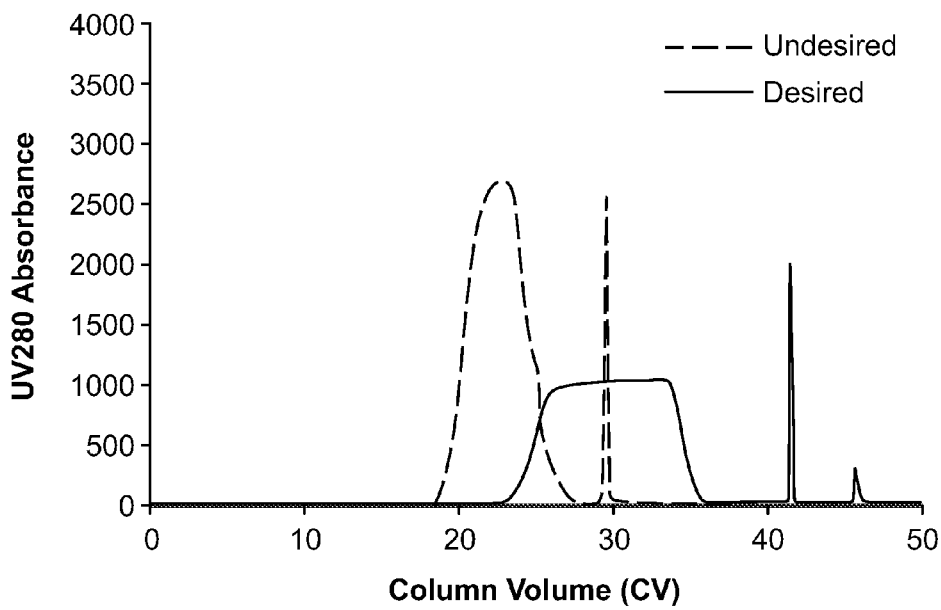
FIG. 1A depicts comparison of a desired and an undesired displacement chromatogram for Adalimumab on Poros XS resin using Expell SP1™.

An objective of the present invention is to provide a method for isolating and purifying proteins from various process-related impurities and product-related substances including, but not limited to, undesired charge variants, size variants (aggregates and fragments) and HCPs at preparative scale using ion exchange displacement chromatography. A further objective of the present invention is to improve the applicability the displacement chromatography technology to large-scale protein purification by reducing required buffer volume for a given separation thereby improving the process efficiency. Another objective of the present invention is to demonstrate the use of mixed mode resin for displacement separation of proteins from various impurities.

In certain embodiments, the present invention is directed to methods and compositions for the purification of proteins, for example, but not limited to, antibodies (e.g., Adalimumab), from process-related impurities and product-related substances. In certain embodiments, the invention is directed to processes where a process stream, e.g., a partially purified antibody composition derived from cell culture harvest solution, is applied to a preparative scale ion exchange adsorbent, e.g., a cation exchange adsorbant ("CEX"), an anion exchange ("AEX") adsorbent, or multimodal ("MM") adsorbent under appropriate conditions. For example, but not by way of limitation, such conditions can include where the pH of the loading and equilibration/wash buffer is below the pI of the target protein to permit the target protein and impurities to bind to the adsorbent, e.g., a CEX adsorbent or a multimodal adsorbent. In certain embodiments, such conditions can also include where a displacing buffer is employed at a pH that is also below the pI of the target protein. In certain embodiments, such conditions can also include where the length of the column employed for the displacement separation is within the practical range of column bed height for large scale processing (i.e. 23 about 30 cm). In certain embodiments, such conditions can also include where the flow residence time employed for the displacement separation is less than about 25 minutes. In certain embodiments, such conditions can also include where a displacer concentration of an appropriately selected displacer is employed to induce the enrichment and separation of the target protein and impurities. In certain embodiments, such conditions can include collecting the displaced sample eluate after at least 10% of the total loaded protein mass has been displaced off the column. In certain embodiments, such conditions can also include the use of a multi-step displacer concentration during displacement in order to render manufacturability by reducing the required buffer volume and process time to a more practical range while achieving desired impurity clearance. In certain embodiments, such conditions can also include the use of a linear gradient displacer concentration to achieve the desired impurities clearance.

For clarity and not by way of limitation, this detailed description is divided into the following sub-portions:
4.1. Definitions;
4.2. Antibody Generation;
4.3. Antibody Production;
4.4. Antibody Purification;
4.5. Methods of Assaying Sample Purity;
4.6. Further Modifications; and
4.7. Pharmaceutical Compositions

4.1. Definitions

In order that the present invention may be more readily understood, certain terms are first defined.

The term "product", as used herein refers to a protein of interest, which may be present in the context of a sample comprising one or more process-related impurities and/or product-related substances. In certain embodiments, the product, i.e., the protein of interest, is an antibody or antigen binding fragment thereof.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody", as used herein, also includes alternative antibody and antibody-like structures, such as, but not limited to, dual variable domain antibodies (DVD-Ig).

The term "antigen-binding portion" of an antibody (or "antibody portion") includes fragments of an antibody that retain the ability to specifically bind to an antigen (e.g., hIL-12, hTNFα, or hIL-18). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody may be part of a larger immunoadhesion molecule, formed by covalent or noncovalent association of the antibody with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The terms "Kabat numbering" "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242, the entire teachings of which are incorporated herein by reference). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities. Moreover, an isolated antibody may be substantially free of other cellular material and/or chemicals.

The term "Koff", as used herein, is intended to refer to the off rate constant for dissociation of an antibody from the antibody/antigen complex.

The term "Kd", as used herein, is intended to refer to the dissociation constant of a particular antibody-antigen interaction.

The phrase "nucleic acid molecule" includes DNA molecules and RNA molecules. A nucleic acid molecule may be single-stranded or double-stranded, but in one aspect is double-stranded DNA.

The phrase "isolated nucleic acid molecule," as used herein in reference to nucleic acids encoding antibodies or antibody portions (e.g., VH, VL, CDR3). The phrase "isolated nucleic acid molecule" is also intended to include sequences encoding bivalent, bispecific antibodies, such as diabodies in which VH and VL regions contain no other sequences other than the sequences of the diabody.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "host cell proteins" (HCPs), as used herein, is intended to refer to non-target protein-related, proteinaceous impurities derived from host cells.

The term "modifying", as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The term "preparative scale", as used herein, refers to a scale of purification operation that can be readily scaled-up and implemented at large scale manufacturing while still providing desired separation. For instance, one skilled in the field may develop a process using, e.g., a 0.5 cm (i.d.)×20 cm (L) column in the lab, and transfer it to large scale production using, e.g., a 30 cm (i.d.)×20 cm (L) column packed with the same resin and operated with the same set of buffers, same linear flow rates (or residence times) and buffer volumes. In preparative scale separation, column bed height is typically ≤about 30 cm and column pressure drop ≤about 5 bar.

The phrase "displacer molecule", as used herein, refers to a molecule employed to displace from the chromatographic support components of the mixture to be separated. Selection of a particular displacer molecule will therefore be dependent on the chromatographic support employed as well as the protein system. Regardless of which chromatographic support is employed, displacer molecules will generally be selected such that they have a high affinity for the support. However, in certain embodiments, a displacer molecule may be selected that has a reduced affinity for the support, so long as it retains the ability to induce a displacement train that includes the protein of interest. In certain non-limiting embodiments, the displacer molecule will be employed in the context of protein separations in ion exchange chromatography and can be selected from, but are not limited to, the group consisting of: polyelectrolytes; polysaccharides; low-molecular-mass dendrimers; amino acids; peptide; antibiotics; and aminoglycosidepolyamines. In certain embodiments the displacer is selected from, but are not limited to, the group consisting of: Expell SP1™ (for CEX and for mixed mode); Expell Q3 (for anion-exchange chromatography (AEX) and for mixed mode); Propel Q2 (for AEX and for mixed mode); and protamine sulfate (for CEX and for mixed mode). Exemplary displacer molecules are described in U.S. Pat. No. 7,632,409, WO 99/47574, WO 03074148, WO2007/055896, WO 2007/064809; and U.S. Pat. No. 6,881,540.

The term "aggregates" used herein means agglomeration or oligomerization of two or more individual molecules, including but not limiting to, protein dimers, trimers, tetramers, oligomers and other high molecular weight species. Protein aggregates can be soluble or insoluble.

The term "fragments" used herein refers to any truncated protein species from the target molecule due to dissociation of peptide chain, enzymatic and/or chemical modifications. For instance, antibody fragments include, but not limited to, Fab, F(ab')$_2$, Fv, scFv, Fd, dAb, or other compositions that contain a portion of the antibody molecule.

The term "charge variants", as used herein, refers to the full complement of product variants including, but not limited to acidic species, and basic species (e.g., Lys variants). In certain embodiments, such variants can include product aggregates and/or product fragments, to the extent that such aggregation and/or fragmentation results in a product charge variation.

As used herein, the term "lysine variant heterogeneity" refers to a characteristic of a population of proteins wherein the population consists of proteins of substantially identical amino acid sequence, but where the population exhibits variation in the presence or absence of C-terminal lysine residues.

In certain embodiments, the protein is an antibody, and the distribution of lysine variant heterogeneity comprises a distribution of the lysine variants Lys 0, Lys 1 and Lys 2, wherein the Lys 0 lysine variant comprises an antibody with heavy chains that do not comprise a C-terminal lysine, wherein the Lys 1 lysine variant comprises an antibody with one heavy chain that comprises a C-terminal lysine, and wherein the Lys 2 lysine variant comprises an antibody wherein both heavy chains comprise a C-terminal lysine.

In certain embodiments, C-terminal lysine variants are associated with charge heterogeneities present in protein preparations, for example, monoclonal antibody (mAb) preparations, produced through a cell culture process. These heterogeneities can be detected by various methods, such as, for example, WCX-10 HPLC (a weak cation exchange chromatography), or IEF (isoelectric focusing).

In certain embodiments, the heterogeneity arises from subspecies of protein differing by the presence or absence of C-terminal lysines. For example, the population of proteins may comprise more than one subspecies of lysine variant. In one non-limiting example, the lysine variants may comprise at least two of Lys 0, Lys 1 and Lys 2 lysine variants which can be detected by weak cation exchange chromatography of the expression product of a host cell expressing Adalimumab.

In certain embodiments, the heterogeneity arises from the size of subpopulations having different C-terminal lysine profiles. For example, the population of proteins may comprise more than one subspecies of C-terminal lysine variant, and each of the variants may be present in different amounts. In one non-limiting example, the C-terminal lysine variants may be at least two of the Lys 0, Lys 1 and Lys 2 lysine variants detected by weak cation exchange chromatography of the expression product of a host cell expressing Adalimumab. In certain embodiments, Lys 0, Lys 1 or Lys 2 subspecies are present in different amounts.

In certain embodiments, the heterogeneity arises from both a difference in the amount of lysine variants in the population of proteins and the type of lysine variants present in the population of proteins.

As used herein, the terms "acidic species", "acidic region" and "acidic species heterogeneity" refer to a characteristic of a population of proteins wherein the population includes a distribution of product-related substances identifiable by the presence of charge heterogeneities. For example, in monoclonal antibody (mAb) preparations, such acidic species heterogeneities can be detected by various methods, such as, for example, WCX-10 HPLC (a weak cation exchange chromatography), or IEF (isoelectric focusing). In certain embodiments, the acidic species identified using such techniques comprise a mixture of product-related impurities containing antibody product fragments (e.g., Fc and Fab fragments), aggregates, and/or post-translation modifications of the antibody product, such as, deamidated and/or glycoslyated antibodies.

In certain embodiments, the acidic species heterogeneity comprises a difference in the type of acidic species present in the population of proteins. For example, the population of proteins may comprise more than one acidic species variant.

In certain embodiments, the heterogeneity of the distribution of acidic species comprises a difference in the amount of acidic species in the population of proteins. For example, the population of proteins may comprise more than one acidic species variant, and each of the variants may be present in different amounts.

4.2. Antibody Generation

The term "antibody" as used in this section refers to an intact antibody or an antigen binding fragment thereof.

The antibodies of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

One animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody can be a human, a chimeric, or a humanized antibody. Humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

Human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen).

Moreover, alternative transchromosomic animal systems expressing human immunoglobulin genes are available in the art and can be used to raise antibodies of the disclosure. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise the antibodies of this disclosure.

In one embodiment, the antibodies of this disclosure are recombinant human antibodies, which can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The antibodies or antigen-binding portions thereof, of this disclosure can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173:1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

4.3. Antibody Production

To express an antibody of the invention, DNAs encoding partial or full-length light and heavy chains are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into an expression vector by standard methods (e.g., ligation of complementary restriction sites on the antibody gene fragment and vector, or blunt end ligation if no restriction sites are present). Prior to insertion of the antibody or antibody-related light or heavy chain sequences, the expression vector may already carry antibody constant region sequences. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, a recombinant expression vector of the invention can carry one or more regulatory sequence that controls the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the antibody chain genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant antibodies of the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody may be cultured in a variety of media. Commercially available media such as Ham's F10™ (Sigma), Minimal Essential Medium™ ((MEM), (Sigma), RPMI-1640 (Sigma), and Dulbecco's Modified Eagle's Medium™ ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact antibodies, such as Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody of this invention. Recombinant DNA technology may also be used to remove some or the entire DNA encoding either or both of the light and heavy chains that is not necessary for binding to the antigen to which the putative antibody of interest binds. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the one to which the putative antibody of interest binds, depending on the specificity of the antibody of the invention, by crosslinking an antibody of the invention to a second antibody by standard chemical crosslinking methods.

In a suitable system for recombinant expression of an antibody of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

When using recombinant techniques, the antibody can be produced intracellularly, in the periplasmic space, or directly secreted into the medium. In one aspect, if the antibody is produced intracellularly, as a first step, the particulate debris, either host cells or lysed cells (e.g., resulting from homogenization), can be removed, e.g., by centrifugation or ultrafiltration. Where the antibody is secreted into the medium, supernatants from such expression systems can be first concentrated using a commercially available protein concentration filter, e.g., an Amicon™ or Millipore Pellicon™ ultrafiltration unit.

Prior to the process of the invention, procedures for purification of antibodies from cell debris initially depend on the site of expression of the antibody. Some antibodies can be secreted directly from the cell into the surrounding growth media; others are made intracellularly. For the latter antibodies, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

4.4. Antibody Purification 4.4.1 Antibody Purification Generally

In certain embodiments, the invention provides methods and compositions for producing a purified or partially purified (e.g., process-related impurity-reduced and/or product-related substance-reduced) protein preparation from a mixture comprising a protein of interest, e.g., an antibody, and at least one process-related impurity or product-related substance. In certain embodiments, the compositions of the present invention include, but are not limited to, process-related impurity-reduced and/or product-related substance-reduced compositions comprising a protein of interest. Such process-related impurity-reduced and/or product-related substance-reduced compositions address the need for improved product characteristics, including, but not limited to, product stability, product safety and product efficacy.

In certain embodiments, the purification process of the invention begins at the separation step when the antibody has been produced using production methods described above and/or by alternative production methods conventional in the art. Once a clarified solution or mixture comprising the protein of interest, e.g., an antibody, has been obtained, separation of the protein of interest from process-related impurities, such as the other proteins produced by the cell, as well as any product-related substances such as charge variants and/or size variants (aggregates and fragments), can be performed. In certain non-limiting embodiments, such separation is performed using Protein A affinity chromatography followed by a displacement chromatographic step. In certain embodiments, a combination of one or more different purification techniques, including ion exchange separation step(s) and/or hydrophobic interaction separation step(s) can also be employed. Such additional purification steps separate mixtures of proteins on the basis of their charge, degree of hydrophobicity, and/or size. In one aspect of the invention, such additional separation steps are performed using chromatography, including hydrophobic, anionic or cationic, or mixed mode interaction. Several different chromatography resins are available for each of these techniques, allowing accurate tailoring of the purification scheme to the particular protein involved. The essence of each of the separation methods is that proteins can either traverse at different rates down a column, achieving a physical separation that increases as they pass further down the column, or to adhere selectively to the separation medium, being then differentially eluted by different solvents, or by the presence of a displacer (in the context of displacement chromatography). In some cases, the antibody is separated from impurities when the impurities specifically adhere to the column and the antibody does not, i.e., the antibody is present in the flow-through, while in other cases the antibody will adhere to the column, while the impurities flow-through.

4.4.2 Primary Recovery

In certain embodiments, the initial steps of the purification methods of the present invention involve the clarification and primary recovery of antibody from a sample matrix. In certain embodiments, the primary recovery will include one or more centrifugation steps to separate the antibody product from the cells and cell debris. Centrifugation of the sample can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification, or in-line filtered through one or more depth filters for further clarification of the sample.

In certain embodiments, the primary recovery will include the use of one or more depth filtration steps to clarify the sample matrix and thereby aid in purifying the antibodies of interest in the present invention. In other embodiments, the primary recovery will include the use of one or more depth filtration steps post centrifugation to further clarify the sample matrix. Non-limiting examples of depth filters that can be used in the context of the instant invention include the Millistak+ X0HC, F0HC, D0HC, A1HC, B1HC depth filters (EMD Millipore), Cuno™ model 30/60ZA, 60/90 ZA, VR05, VR07, delipid depth filters (3M Corp.). A 0.2 µm filter such as Sartorius's 0.45/0.2 µm Sartopore™ bi-layer or Millipore's Express SHR or SHC filter cartridges typically follows the depth filters.

In certain embodiments, the primary recovery process can also be a point at which to reduce or inactivate viruses that can be present in the sample matrix. For example, any one or more of a variety of methods of viral reduction/inactivation can be used during the primary recovery phase of purification including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972. In certain embodiments of the present invention, the sample matrix is exposed to detergent viral inactivation during the primary recovery phase. In other embodiments, the sample matrix may be exposed to low pH inactivation during the primary recovery phase.

In those embodiments where viral reduction/inactivation is employed, the sample mixture can be adjusted, as needed, for further purification steps. For example, following low pH viral inactivation, the pH of the sample mixture is typically adjusted to a more neutral pH, e.g., from about 4.5 to about 8.5, prior to continuing the purification process. Additionally, the mixture may be diluted with water for injection (WFI) to obtain a desired conductivity.

4.4.3 Protein A Affinity Chromatography

In certain embodiments, particularly where the protein of interest is an antibody, the primary recovery sample is subjected to Protein A affinity chromatography to substantially purify the antibody of interest away from HCPs. There are a variety of commercial sources for Protein A resin. Suitable resins include, but not limited to, MabSelect SuRe™, MabSelect SuRe LX, MabSelect, MabSelect Xtra, rProtein A Sepharose from GE Healthcare, ProSep HC, ProSep Ultra, and ProSep Ultra Plus from EMD Millipore, MapCapture from Life Technologies.

In certain embodiments, the Protein A column can be equilibrated with a suitable buffer prior to sample loading. Following the loading of the column, the column can be washed one or multiple times using a suitable sets of buffers. The Protein A column can then be eluted using an appropriate elution buffer. The eluate can be monitored using techniques well known to those skilled in the art. The eluate fractions of interest can be collected and then prepared for further processing.

The Protein A eluate may subject to a viral inactivation step either by detergent or low pH, provided this step is not performed prior to the Protein A capture operation. A proper detergent concentration or pH and time can be selected to obtain desired viral inactivation results. After viral inactivation, the Protein A eluate is usually pH and/or conductivity adjusted for subsequent purification steps.

The Protein A eluate may be subjected to filtration through a depth filter to remove turbidity and/or various impurities from the antibody of interest prior to additional chromatographic polishing steps. Examples of depth filters include, but not limited to, Millistak+X0HC, F0HC, D0HC, A1HC, and B1HC Pod filters (EMD Millipore), or Zeta Plus 30ZA/60ZA, 60ZA/90ZA, delipid, VR07, and VR05 filters (3M). The Protein A eluate pool may need to be conditioned to proper pH and conductivity to obtain desired impurity removal and product recovery from the depth filtration step.

4.4.4 Displacement Chromatography

In certain embodiments of the present invention, a sample, e.g., a primary recovery sample, a Protein A eluate sample, or a sample having undergone one or more of the purification strategies outlined herein, is subjected to displacement chromatography. In certain embodiments the displacer molecule is selected to have a higher affinity for the stationary phase (i.e., the chromatographic support) than the components present in the material to be separated. In certain embodiments, the displacer induces the components of the mixture to develop into consecutive zones of concentrated and purified species in the order of decreasing binding affinity ahead of the displacer front (a "displacement train"). In certain embodiments, the displacement process allows for higher column loading levels (as compared to conventional high-resolution chromatographic separations such as bind and linear gradient elution mode) without compromising the purity and recovery of the component of interest. In certain embodiments, washing of the displacement train from the column using the displacer solution allows for the component of interest to be isolated by collecting (and pooling if necessary) the proper fraction(s) of the displaced eluate. Along with acidic species, other product-related substances, such as basic species, product aggregates, and/or product fragments, and process-related impurities, such as HCPs, can be selectively collected or reduced.

In certain embodiments, the displacer will be employed in the context of an ion exchange or mixed mode chromatographic separation. A detailed description of ion exchange chromatography and a listing of exemplary chromatographic supports which can be employed in the context of displacement chromatography are presented in Section 4.4.5, below. A detailed description of mixed mode chromatography and a listing of exemplary chromatographic supports which can be employed in the context of displacement chromatography are presented in Section 4.4.6, below. In certain non-limiting embodiments, a cation exchange, an anion exchange, or a mixed mode displacement chromatography step is employed to effectively reduce product-related substances (e.g., acidic species and/or basic species such as Lys variants) from, e.g., a monoclonal antibody feed stream. In certain of such embodiments, conventional (or relatively weak) binding conditions can be employed and cationic molecules having high affinity for a CEX, AEX, or multimodal ligand (such as Expell SP1™ and protamine sulfate) can be employed to induce the formation of a product-related substances displacement train. In certain of such embodiments, the acidic population is enriched in the front followed by the main isoform, and, thereafter, the basic population. Thus, in certain embodiments, exclusion of those earlier fractions from the remainder eluate results in an AR-reduced product. Alternatively, exclusion of the fractions following the main isoform results in a Lys variant-reduced product. In certain embodiments, the fragments and aggregates are reduced in an AR-reduced product. In certain embodiments, the HCPs are reduced in an AR-reduced product.

In certain embodiments, the displacer concentration will be selected from the range of about 0.1 mM to about 10 mM, or about 0.25 mM to about 10 mM. In certain embodiments, the displacer concentration will be selected from a range of about 0.1 mM to about 5 mM, or about 0.25 mM to about 3 mM. In certain embodiments, the displacer concentration will be selected from a range of about 0.1 mM to about 5 mM, or about 0.25 mM to about 2 mM. In certain embodiments, the displacer concentration will be selected from a range of about 0.1 mM to about 2 mM, or about 0.25 mM to about 1 mM. In certain embodiments, the displacer concentration will be selected from a concentration of about 0.1 mM to about 1 mM, or about 0.25 mM to about 0.5 mM. In certain embodiments the displacer is Expell SP1™ and the displacer concentration will be selected from the range of about 0.1 mM to about 10 mM, or about 0.25 mM to about 10 mM. In certain embodiments, the displacer is protamine sulfate and the displacer concentration will be selected from the range of about 0.1 mM to about 5 mM, or about 0.25 mM to about 5 mM.

In certain embodiments, a displacing buffer was used in one-step displacement process. In certain embodiments, the total volume of the one-step displacing buffer is in the range of about 20 CVs to about 50 CVs, or about 25 CVs to about 40 CVs, or about 30 CVs.

Although displacement chromatography conventionally employs a displacer at a fixed concentration to achieve component separation, an improved method using multiple displacing buffers is disclosed herein. In certain embodiments, a two-step displacement method is employed where a first displacer concentration is employed for a certain initial number of column volumes (CVs) and a second, higher, displacer concentration is employed for a subsequent number of CVs. The total volume of the displacing buffers needed to complete the displacement process is significantly (e.g. 25-45%) less than that needed when using one displacing buffer in the one-step displacement process in order to achieve comparable separation performances. In certain embodiments the first displacer concentration is about 0.25 mM, about 0.35 mM, or about 0.5 mM. In certain embodiments, the second displacer concentration is about 0.5 mM, about 1 mM, about 2 mM, about 3 mM, about 4 mM, or about 5 mM.

In certain embodiments, a two-step displacement method is employed where the first displacer concentration is employed for up to about 10 CVs. In certain embodiments, the first displacer concentration is employed for up to about 25 CVs. In certain embodiments, the second displacer concentration is employed for up to about 10 CVs. In certain embodiments, the second displacer concentration is employed for up to about 25 CVs. In certain embodiments, the total required displacing buffer volume is about 13 CVs for a two-step displacement process. In certain embodiments, the total required displacer buffer volume is about 15 CVs for a two-step displacement process. In certain embodiments, the total required displacer buffer volume is about 33 CVs for a two-step displacement process. Once skilled in the art further reduction in required buffer volumes for each displacement step is expected. In certain embodiments, multiple steps of increasing displacer concentration are employed. As outlined in the Examples section, below, incorporation of additional displacement concentration steps into the purification strategy can allow for unexpectedly efficient charge variant, product aggregate, product fragment, and/or HCP clearance.

In certain embodiments, a linear gradient displacement method is employed where an initial, low, displacer concentration is followed by the addition of displacer at increasing concentrations in accordance with a linear gradient. For example, but not by way of limitation, the displacer concentration can range from about 0 mM to about 1 mM over the course of about 40 CVs. Again, as outlined in the Examples section, below, incorporation of a linear displacer concentration gradient into the purification strategy can allow for unexpectedly efficient charge variant, product aggregate, product fragment, and/or HCP clearance.

In certain embodiments, a displacement buffer consisting of two or more displacers is used. In certain embodiments, different displacers are used in the multi-step displacement process.

In certain embodiments of the present invention, the pH of the displacing wash buffer is below the pI of the protein of interest. In certain embodiments, the pH of the displacing wash buffer is in the range of about 5.0 to about 9.0, about 6.0 to about 8.0, about 7.0 to about 7.7, or about 7.5 to about 7.7. In certain embodiments of the present invention, the conductivity of the wash buffer is between about 1 to about 86 mS/cm, about 2 to about 20 mS/cm, about 2 to about 7 mS/cm, or about 5 to about 6.6 mS/cm. In certain embodiments of the present invention, the column bed height is between about 10 cm to about 30 cm, about 15 cm to about 25 cm, about 20 cm to about 30 cm, or about 25 cm. In certain embodiments of the present invention, the flow residence time is between about 2 minutes to about 25 minutes, about 5 minutes to about 20 minutes, about 10 minutes to about 20 minutes, or about 15 minutes to about 20 minutes.

In certain embodiments, the displacer buffer pH and displacer concentration can affect the displacement profile and, as a result, impact clearance of process-related impurities and/or product-related substances, such as charge variants, in unexpected ways. Thus, effective operating regimes with regard to the reduction of process-related impurities and/or product-related substances depend on the specific protein-resin-displacer system. For example, but not by way of limitation, when a feed stream containing Adalimumab is separated using displacement chromatography, significant AR reduction ($\Delta$AR %) can be achieved using a displacing buffer with pH in the range of 6-8 with displacer concentration as low as 0.25-0.5 mM. In fact, as described in Section 5.2 below, the extent of Adalimumab AR reduction increases significantly as pH varies from 6.5 to 7.5, for example, over a 6% decrease in AR level can be achieved at pH 7.5 with a product yield~75%. In certain embodiments, as outlined in the Examples presented below, the total AR level (%) in Adalimumab product pool can be reduced by over 10% with an acceptable processing yield ($\geq$75%) from a CEX displacement chromatography process, or 4-7% from a mixed mode displacement chromatography process. Similarly, for mAb X, FIG. 32 indicates that ΔAR % surprisingly increases from 3.3 to 6.5% as pH varies from 7 to 7.7 in a mixed mode displacement chromatography process.

In certain embodiments, conditions selected for reducing AR are also capable of reducing process-related impurities and/or other product-related substances. For example, but not by way of limitation, conditions selected for AR reduction are also capable of reducing process-related impurities, such as HCPs. In additional, non-limiting examples, conditions selected for AR reduction are also capable of reducing product-related impurities, such as aggregates and/or fragments.

In certain embodiments, displacement chromatography can be used as the sole method of purification of the protein of interest. In certain embodiments, displacement chromatography can be used in combination with other purification strategies, such as, but not limited to, the alternative techniques described herein, to reduce process-related impurities and/or other product-related substances.

In certain embodiments, fractions are collected during the displacement step and are combined (pooled) after appropriate analysis to provide a protein preparation, which is also referred to herein as a purified or partially-purified sample, that contains a desired level of the protein of interest and which can include one or more process-related impurities and/or other product-related substances. In certain embodiments, one or more process monitoring tools can be used in connection with the techniques described herein to facilitate the identification of an effective product pooling strategy. In certain embodiments, such monitoring can include on-line or in-line process monitoring. For example, but not by way of limitation, spectroscopy methods such as UV, NIR, FTIR, Fluorescence, and Raman may be used to monitor levels of product-related species, e.g., acidic species and lysine variants, in an on-line, at line or in-line mode. These methods allow for the production of data that can then be used to control the level of product-related species in the pooled material collected. In certain embodiments, specific signals arising from the chemical modification of the proteins such as glycation, MGO modification, deamidation, glycosylation may be specifically measurable by spectroscopic methods through such in-line, on-line or at-line methods, enabling real time or near-real time control of product quality of the resulting product.

In certain embodiments, the purification and/or pooling techniques described herein allow for the reduction of process-related impurities and/or other product-related substances. In certain embodiments, the purification and/or pooling techniques described herein allow for reduction of process-related impurities and the selective inclusion of particular product-related substances. For example, but not by way of limitation, the purification and/or pooling techniques described herein allow for modulation of the concentration of product-related substances in the purified sample, e.g., increasing or decreasing the amount of AR and/or basic species. In certain embodiments, the concentration of particular AR and/or basic species, e.g., Lys0, Lys1, and/or Lys2, are modulated (increased or decreased) in the purified sample. In certain embodiments, such techniques can be used to ensure product uniformity over the course of multiple production runs.

4.4.5 Ion Exchange Chromatography

In certain embodiments, the instant invention provides methods for producing process-related impurity and/or product-related substance-reduced protein preparation from a mixture comprising a protein of interest (i.e., a product) and at least one process-related impurity and/or product-related substance by subjecting the mixture to at least one ion exchange separation step. In certain embodiments, the ion exchange step will occur after the above-described Protein A affinity and/or displacement chromatography steps, such that an eluate comprising the protein of interest is obtained. Ion exchange separation includes any method by which two substances are separated based on the difference in their respective ionic charges, and can employ either cationic exchange material or anionic exchange material.

The use of a cationic exchange material versus an anionic exchange material can be based on the local charges of the protein at a given solution condition. Therefore, it is within the scope of this invention to employ an anionic exchange step prior to or subsequent to the use of a displacement chromatography step, or a cationic exchange step prior to or subsequent to the use of a displacement chromatography step.

In performing the separation, the initial protein mixture can be contacted with the ion exchange material by using any of a variety of techniques, e.g., using a batch purification technique or a chromatographic technique.

For example, in the context of batch purification, ion exchange material is prepared in, or equilibrated to, the desired starting buffer. Upon preparation, or equilibration, a slurry of the ion exchange material is obtained. The protein of interest, e.g., an antibody, solution is contacted with the slurry to adsorb the protein of interest to be separated to the ion exchange material. The solution comprising the process-related impurities and product-related substances that do not bind to the ion exchange material is separated from the slurry, e.g., by allowing the slurry to settle and removing the supernatant. The slurry can be subjected to one or more wash steps. If desired, the slurry can be contacted with a solution of higher conductivity to desorb process-related impurities and product-related substances that have bound to the ion exchange material. In order to elute bound polypeptides, the salt concentration of the buffer can be increased.

In the context of chromatographic separation, a chromatographic apparatus, commonly cylindrical in shape, is employed to contain the chromatographic support material (e.g., ion exchange material) prepared in an appropriate buffer solution. The chromatographic apparatus, if cylindrical, can have a diameter of about 5 mm to about 50 mm, and a height of 5 cm to 1 m, and in certain embodiments, particularly for large scale processing, a height of ≤30 cm is employed. Once the chromatographic material is added to the chromatographic apparatus, a sample containing the protein of interest, e.g., an antibody, is contacted to the chromatographic material to adsorb the protein of interest to be separated to the chromatographic material. The solution comprising the process-related impurities and product-related substances that do not bind to the chromatographic material is separated from the material by washing the materials and collecting fractions from the bottom of the column. The chromatographic material can be subjected to one or more wash steps. If desired, the chromatographic material can be contacted with a solution of higher conductivity to desorb process-related impurities and product-related substances that have bound to the chromatographic material. In order to elute bound polypeptides, the salt concentration of the buffer can be increased.

Ion exchange chromatography separates molecules based on differences between the local charges of the proteins of interest and the local charges of the chromatographic material. A packed ion-exchange chromatography column or an ion-exchange membrane device can be operated either in bind-elute mode or flow-through mode. In the bind-elute mode, the column or the membrane device is first conditioned with a buffer with low ionic strength and proper pH under which the protein carries sufficient local opposite charge to the local charge of the material immobilized on the resin based matrix. During the feed load, the protein of interest will be adsorbed to the resin due to electrostatic attraction. After washing the column or the membrane device with the equilibration buffer or another buffer with different pH and/or conductivity, the product recovery is achieved by increasing the ionic strength (i.e., conductivity) of the elution buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). In the flow-through mode, the column or the membrane device is operated at selected pH and conductivity such that the protein of interest does not bind to the resin or the membrane while the process-related impurities and/or product-related substances will be retained to the column or the membrane. The column is then regenerated before next use.

Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substitutents include carboxymethyl (CM), sulfoethyl (SE), sulfopropyl (SP), phosphate (P) and sulfonate (S). Cellulose ion exchange resins such as DE23™, DE32™, DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow, and Capto™ S are all available from GE Healthcare. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa., or Nuvia S and UNOSphere™ S from BioRad, Hercules, Calif., Eshmuno® S from EMD Millipore, Billerica, Calif.

This ion exchange step facilitates the purification of the antibody of interest by reducing impurities such as HCPs, DNA and aggregates. In certain aspects, the ion exchange column is an anion exchange column. For example, but not by way of limitation, a suitable resin for such an anion exchange column is Capto™ Q, Nuvia™ Q, Q Sepharose Fast Flow, and Poros HQ 50. These resins are available from commercial sources such as GE Healthcare, BioRad, or Life Technologies. This anion exchange chromatography process can be carried out at or around room temperature.

4.4.6 Mixed Mode Chromatography

Mixed mode chromatography, also referred to herein as "multimodal chromatography", is a chromatographic strategy that utilizes a support comprising a ligand that is capable of providing at least two different, in certain embodiments co-operative, sites that interact with the substance to be bound. In certain embodiments, one of these sites gives an attractive type of charge-charge interaction between the ligand and the substance of interest and the other site provides for electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole etc. Mixed mode chromatographic supports include, but are not limited to, Nuvia C Prime, Toyo Pearl MX Trp 650M, and Eshmuno® HCX.

In certain embodiments, the mixed mode chromatography resin is comprised of ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support is prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers can be produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

4.4.7 Hydrophobic Interaction Chromatography

The present invention also features methods for producing a process-related impurity and/or product-related substance-reduced protein preparation from a mixture comprising a protein of interest, e.g., an antibody, and at least one process-related impurity and/or product-related substance further comprising a hydrophobic interaction chromatography (HIC) step in addition to the displacement chromatography step.

In performing the separation, the sample mixture is contacted with the HIC material, e.g., using a batch purification technique or using a column or membrane chromatography. Prior to HIC purification it may be desirable to adjust the concentration of the kosmotropic salt to achieve desired protein binding to the resin or the membrane.

Whereas ion exchange chromatography relies on the local charge of the protein of interest for selective separation, hydrophobic interaction chromatography employs the hydrophobic properties of the proteins to achieve selective separation. Hydrophobic groups on the protein interact with hydrophobic groups of the resin or the membrane. The more hydrophobic a protein is the stronger it will interact with the column or the membrane. Thus the HIC step removes process-related impurities (e.g., HCPs) as well as product-related substances (e.g., aggregates and fragments).

Like ion exchange chromatography, a HIC column or membrane device can also be operated in product a bind-elute mode, a flow-through, or a hybrid mode wherein the product exhibits reversible binding to the chromatographic material. The bind-elute mode of operation has been explained above. For flow-through, the protein sample typically contains a relatively low level of salt than that used in the bind-elute mode. During this loading process, process-related impurities and product-related substances will bind to the resin while product flows through the column. After loading, the column is regenerated with water and cleaned with caustic solution to remove the bound impurities before next use. When used in connection with a hybrid mode, the product can be immobilized on the chromatographic support in the presence of a loading buffer, but can be removed by successive washes of buffer identical to or substantially similar to the loading buffer. During this process, process-related impurities and product-relates substances will either bind to the chromatographic material or flow through with a profile distinct from the protein of interest.

As hydrophobic interactions are strongest at high ionic strength, this form of separation is conveniently performed following salt elution step, such as those that are typically used in connection with ion exchange chromatography. Alternatively, salts can be added into a low salt level feed stream before this step. Adsorption of the antibody to a HIC column is favored by high salt concentrations, but the actual concentrations can vary over a wide range depending on the nature of the protein of interest, salt type and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{2+}$; $Ca^{2+}$; $Mg^{2+}$; $Li^+$; $Cs^+$; $Na^+$; $K^+$; $Rb^+$; $NH_4^+$, while anions may be ranked in terms of increasing chaotropic effect as $PO_4^{3-}$; $SO_4^{2-}$; $CH_3CO_3^-$; $Cl^-$; $Br^-$; $NO_3^-$; $ClO_4^-$; $I^-$; $SCN^-$.

In general, $Na^+$, $K^+$ or $NH_4^+$ sulfates effectively promote ligand-protein interaction in HIC. Salts may be formulated that influence the strength of the interaction as given by the following relationship: $(NH_4)_2SO_4 > Na_2SO_4 > NaCl > NH_4Cl > NaBr > NaSCN$. In general, salt concentrations of between about 0.75 M and about 2 M ammonium sulfate or between about 1 and 4 M NaCl are useful.

HIC media normally comprise a base matrix (e.g., cross-linked agarose or synthetic copolymer material) to which hydrophobic ligands (e.g., alkyl or aryl groups) are coupled. A suitable HIC media comprises an agarose resin or a membrane functionalized with phenyl groups (e.g., a Phenyl Sepharose™ from GE Healthcare or a Phenyl Membrane from Sartorius). Many HIC resins are available commercially. Examples include, but are not limited to, Capto Phenyl, Phenyl Sepharose™ 6 Fast Flow with low or high substitution, Phenyl Sepharose™ High Performance, Octyl Sepharose™ High Performance (GE Healthcare); Fractogel™ EMD Propyl or Fractogel™ EMD Phenyl (E. Merck, Germany); Macro-Prep™ Mehyl or Macro-Prep™ t-Butyl columns (Bio-Rad, California); WP HI-Propyl (C3)™ (J. T. Baker, New Jersey); and Toyopearl™ ether, phenyl or butyl (TosoHaas, PA).

4.4.8 Viral Filtration

Viral filtration is a dedicated viral reduction step in the entire purification process. This step is usually performed post chromatographic polishing steps. Viral reduction can be achieved via the use of suitable filters including, but not limited to, Planova 20N™, 50 N or BioEx from Asahi Kasei Pharma, Viresolve™ filters from EMD Millipore, ViroSart CPV from Sartorius, or Ultipor DV20 or DV50™ filter from Pall Corporation. It will be apparent to one of ordinary skill in the art to select a suitable filter to obtain desired filtration performance.

4.4.9 Ultrafiltration/Diafiltration

Certain embodiments of the present invention employ ultrafiltration and diafiltration steps to further concentrate and formulate the protein of interest, e.g., an antibody product. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). One filtration process is Tangential Flow Filtration as described in the Millipore catalogue entitled "Pharmaceutical Process Filtration Catalogue" pp. 177-202 (Bedford, Mass., 1995/96). In contrast, diafiltration is a method of using membrane filters to remove and exchange salts, sugars, and non-aqueous solvents, to separate free from bound species, to remove low molecular-weight species, and/or to cause the rapid change of ionic and/or pH environments. Examples of membrane cassettes suitable for the present invention include, but not limited to, Pellicon 2 or Pellicon 3 cassetts with 10 kD, 30 kD or 50 kD membranes from EMD Millipore, Kvick 10 kD, 30 kD or 50 kD membrane cassettes from GE Healthcare, and Centramate or Centrasette 10 kD, 30 kD or 50 kD cassettes from Pall Corporation.

4.5. Methods of Assaying Sample Purity 4.5.1 Assaying Host Cell Protein

The present invention also provides methods for determining the residual levels of host cell protein (HCP) concentration in the isolated/purified antibody composition. As described above, HCPs are desirably excluded from the final target substance product. Exemplary HCPs include proteins originating from the source of the antibody production. Failure to identify and sufficiently remove HCPs from the target antibody may lead to reduced efficacy and/or adverse subject reactions.

As used herein, the term "HCP ELISA" refers to an ELISA where the second antibody used in the assay is specific to the HCPs produced from cells, e.g., CHO cells, used to generate the antibody of interest. The second antibody may be produced according to conventional methods known to those of skill in the art. For example, the second antibody may be produced using HCPs obtained by sham production and purification runs, i.e., the same cell line used to produce the antibody of interest is used, but the cell line is not transfected with antibody DNA. In an exemplary embodiment, the second antibody is produced using HCPs similar to those expressed in the cell expression system of choice, i.e., the cell expression system used to produce the target antibody.

Generally, HCP ELISA comprises sandwiching a liquid sample comprising HCPs between two layers of antibodies, i.e., a first antibody and a second antibody. The sample is incubated during which time the HCPs in the sample are captured by the first antibody, for example, but not limited to goat anti-CHO, affinity purified (*Cygnus*). A labeled second antibody, or blend of antibodies, specific to the HCPs produced from the cells used to generate the antibody, e.g., anti-CHO HCP Biotinylated, is added, and binds to the HCPs within the sample. In certain embodiments the first and second antibodies are polyclonal antibodies. In certain aspects the first and second antibodies are blends of polyclonal antibodies raised against HCPs. The amount of HCP contained in the sample is determined using the appropriate test based on the label of the second antibody.

HCP ELISA may be used for determining the level of HCPs in an antibody composition, such as an eluate, displacement samples or flow-through fractions obtained using the process described above. The present invention also provides a composition comprising an antibody, wherein the composition has less than 100 ng/mgHCPs as determined by an HCP Enzyme Linked Immunosorbent Assay ("ELISA").

4.5.2 Assaying Charge and Size Variants

In certain embodiments, the levels of product-related substances, such as acidic species and other charge variants, in the chromatographic samples produced using the techniques described herein are analyzed. In certain embodiments a CEX-HPLC method is employed. For example, but not by way of limitation, a 4 mm×250 mm analytical Dionex ProPac WCX-10 column (Dionex, CA) can be used along with a Shimazhu HPLC system. In certain embodiments, the mobile phases employed in such an assay will include a 10 mM Sodium Phosphate dibasic pH 7.5 buffer (Mobile phase A) and a 10 mM Sodium Phosphate dibasic, 500 mM Sodium Chloride pH 5.5 buffer (Mobile phase B). In certain embodiments, the mobile phases can include a 20 mM MES, pH 6.5 buffer (Mobile phase A) and a 20 mM MES, 500 mM NaCl, pH 6.5 buffer (Mobile phase B). In certain embodiments, the mobile phases can include a 20 mM MES, pH 6.2 buffer (Mobile phase A) and a 20 mM MES, 250 mM NaCl, pH 6.2 buffer (Mobile phase B). In certain embodiments, a binary gradient, for example, but not by way of limitation, a 6% B: 0 min; 6-16% B: 0-20 min; 16-100% B: 20-22 min; 100% B: 22-26 min; 100-6% B: 26-28 min; 6% B: 28-35 min gradient can be used with detection at 280 nm. In certain, non-limiting embodiments, a binary gradient comprising 10% B: 0 min; 10-28% B: 1-46 min; 28-100% B: 46-47 min; 100% B: 47-52 min; 100-10% B: 52-53 min; 10% B: 53-58 min, will be used with detection at 280 nm. In certain embodiments, a binary gradient such as a 1% B: 0-1 min; 1-25% B: 1-46 min; 25-100% B: 46-47 min; 100% B: 47-52 min; 100-1% B: 52-53 min; 1% B: 53-60 min gradient can be used with detection at 280 nm. Quantitation can be based on the relative area percentage of detected peaks. In certain embodiments, the peaks that elute at residence time less than ~7 min will represent the acidic peaks or AR region. In certain embodiments, all peaks eluting prior to the Main Isoform peak can be summed as the acidic region, and all peaks eluting after the Main peak can be summed as the basic region. In certain embodiments, all peaks eluting prior to the Main Isoform peak (but after, e.g., a 2 min retention time) were summed as the acidic region, and all peaks eluting after the Main peak were summed as the basic region.

In certain embodiments, the levels of aggregates, monomer, and fragments in the chromatographic samples produced using the techniques described herein are analyzed. In certain embodiments, the aggregates, monomer, and fragments are measured using a size exclusion chromatography (SEC) method for each molecule. For example, but not by way of limitation, a TSK-gel G3000SW×L, 5 µm, 125 Å, 7.8×300 mm column (Tosoh Bioscience) can be used in connection with certain embodiments, while a TSK-gel Super SW3000, 4 µm, 250 Å, 4.6×300 mm column (Tosoh Bioscience) can be used in alternative embodiments. In certain embodiments, the aforementioned columns are used along with an Agilent or a Shimazhu HPLC system. In certain embodiments, sample injections are made under isocratic elution conditions using a mobile phase consisting of, for example, 100 mM sodium sulfate and 100 mM sodium phosphate at pH 6.8, and detected with UV absorbance at 214 nm. In certain embodiments, the mobile phase will consist of 1×PBS at pH 7.4, and elution profile detected with UV absorbance at 280 nm. In certain embodiments, quantification is based on the relative area of detected peaks.

4.6. Further Modifications

The purified proteins, e.g., antibodies, of the present invention can be modified. In some embodiments, the antibodies are chemically modified to provide a desired effect. For example, but not by way of limitation, pegylation of antibodies or antibody fragments of the invention may be carried out by any of the pegylation reactions known in the art, as described, e.g., in the following references: Focus on Growth Factors 3:4-10 (1992); EP 0 154 316; and EP 0 401 384, each of which is incorporated by reference herein in its entirety. In one aspect, the pegylation is carried out via an acylation reaction or an alkylation reaction with a reactive polyethylene glycol molecule (or an analogous reactive water-soluble polymer). A suitable water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under suitable conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

An antibody of the invention can be derivatized or linked to another functional molecule (e.g., another peptide or protein or a small molecule). For example, an antibody of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody with another molecule (such as a streptavidin core region or a polyhistidine tag) or can modulate the potency and/or efficacy of the targeted therapy (e.g. an antibody drug conjugate).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

4.7. Pharmaceutical Compositions

The proteins of interest, e.g., antibodies and antibody-binding portions thereof, of the invention can be incorporated into pharmaceutical compositions suitable for administration to a subject. In certain embodiments, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is desirable to include isotonic agents, e.g., sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody.

The antibodies and antibody-binding portions thereof, of the invention can be incorporated into a pharmaceutical composition suitable for parenteral administration. The antibody or antibody-portions can be prepared as an injectable solution containing, e.g., 0.1-250 mg/mL antibody. The injectable solution can be composed of either a liquid or lyophilized dosage form in a flint or amber vial, ampule or pre-filled syringe. The buffer can be L-histidine approximately 1-50 mM, (optimally 5-10 mM), at pH 5.0 to 7.0 (optimally pH 6.0). Other suitable buffers include but are not limited to sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 24%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

In one aspect, the pharmaceutical composition includes the antibody at a dosage of about 0.01 mg/kg-10 mg/kg. In another aspect, the dosages of the antibody include approximately 1 mg/kg administered every other week, or approximately 0.3 mg/kg administered weekly. A skilled practitioner can ascertain the proper dosage and regime for administering to a subject.

The compositions of this invention may be in a variety of forms. These include, e.g., liquid, semi-solid and solid dosage forms, such as liquid solutions (e.g., injectable and infusible solutions), dispersions or suspensions, tablets, pills, powders, liposomes and suppositories. The form depends on, e.g., the intended mode of administration and therapeutic application. Typical compositions are in the form of injectable or infusible solutions, such as compositions similar to those used for passive immunization of humans with other antibodies. One mode of administration is parenteral (e.g., intravenous, subcutaneous, intraperitoneal, intramuscular). In one aspect, the antibody is administered by intravenous infusion or injection. In another aspect, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the methods of preparation are vacuum drying and spray-drying that yields a powder of the active ingredient plus any additional desired ingredient from a previously sterile-filtered solution thereof. The proper fluidity of a solution can be maintained, e.g., by the use of a coating such as lecithin, by the maintenance of the required particle size in the case of dispersion and by the use of surfactants. Prolonged absorption of injectable compositions can be brought about by including in the composition an agent that delays absorption, e.g., monostearate salts and gelatin.

The antibodies and antibody-binding portions thereof, of the present invention can be administered by a variety of methods known in the art, one route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978, the entire teaching of which is incorporated herein by reference.

In certain aspects, an antibody or antibody-binding portion thereof, of the invention may be orally administered, e.g., with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain aspects, an antibody or antibody-binding portion thereof, of the invention is co-formulated with and/or co-administered with one or more additional therapeutic agents that are useful for treating disorders. Such combination therapies may advantageously utilize lower dosages of the administered therapeutic agents, thus avoiding possible toxicities or complications associated with the various monotherapies. It will be appreciated by the skilled practitioner that when the antibodies of the invention are used as part of a combination therapy, a lower dosage of antibody may be desirable than when the antibody alone is administered to a subject (e.g., a synergistic therapeutic effect may be achieved through the use of combination therapy which, in turn, permits use of a lower dose of the antibody to achieve the desired therapeutic effect).

It should be understood that the antibodies of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition, e.g., an agent which affects the viscosity of the composition.

5. EXAMPLES

Three antibodies were used in connection with the studies outlined below (Sections 5.1-5.8). Adalimumab antibody was generated from cell culture processed using chemical defined medium (CDM) and purified by a 4.4 cm (id.)×~20 cm (L) MabSelect SuRe Protein A column. mAb X bulk drug substance was obtained from a three-step large scale purification process. mAb Y antibody was generated from a large scale manufacturing process and purified by a Mab-Select SuRe Protein A column. Adalimumab Protein A eluate was in a buffer of ~20 mM acetic acid at pH~4.2. The mAb X was in a buffer containing ~15 mM histidine, pH~6. The mAb Y was in a buffer containing ~10 mM sodium formate, pH~4.2. Each mAb feed was conditioned to the targeted pH, conductivity and concentration prior to the displacement chromatography experiment.

The cationic displacers, Expell SP1™ and protamine sulfate (from salmon sperm), were purchased from SACHEM Chemical Company and Sigma Aldrich, respectively.

Poros XS CEX resin (Life Technologies) was packed in a 0.66 cm×~25 cm column. The column was equilibrated with a 140 mM Tris/Acetate buffer or a 30 mM MES, 10 mM NaCl buffer at the targeted pH and conductivity (Table 1). After equilibration, the column was loaded with each pre-conditioned feed at a resin loading level of ~40 g/L followed by a 2 CV of equilibration buffer wash. The displacing buffer, which consists of defined concentration of Expell SP1™ or protamine sulfate in the equilibration buffer, was flowed through the column to initiate the displacement process. In standard one-step displacement wash process, this step was continued for at least 30 CV at a flow rate corresponding to 15 to 22 min residence time (RT) before column regeneration and cleaning with a caustic solution consisting of 0.5 N NaOH and 0.5 M KCl. Alternatively, the displacement wash step comprised two displacement buffers each flowing for defined volumes, or a linear gradient flow from low to high concentration displacer buffer. Sample fractions were collected at every 0.5 or 1 CV for protein concentration and quality analysis. The specific processing conditions are detailed in Tables 1 and 2.

Capto MMC resin (GE Healthcare) was packed in a 0.66 cm×~30 cm column. The column was equilibrated with a 140 mM Tris/Acetate buffer at the targeted pH and conductivity (Table 3). After equilibration, the column was loaded with each pre-conditioned feed at a resin loading level about 34 to 40 g/L followed by a 2 CV equilibration buffer wash. The displacing buffer, which consists of defined concentration of protamine sulfate in the equilibration buffer, was flowed through the column to initiate the displacement process. This step was continued for 30 CV at a flow rate corresponding to ~22 min RT before column regeneration and cleaning. Sample fractions were collected at every 0.5 or 1 CV for protein concentration and quality analysis. The specific processing conditions are detailed in Table 3.

The levels of acidic species and other charge variants in the Adalimumab, mAb X and mAb Y samples were quantified using the respective qualified CEX-HPLC method. For Adalimumab, a 4 mm×250 mm analytical Dionex ProPac WCX-10 column (Dionex, CA) was used along with a Shimazhu HPLC system. The mobile phases were 10 mM Sodium Phosphate dibasic pH 7.5 buffer (Mobile phase A) and 10 mM Sodium Phosphate dibasic, 500 mM Sodium Chloride pH 5.5 buffer (Mobile phase B). A binary gradient (6% B: 0 min; 6-16% B: 0-20 min; 16-100% B: 20-22 min; 100% B: 22-26 min; 100-6% B: 26-28 min; 6% B: 28-35 min) was used with detection at 280 nm. Quantitation was based on the relative area percentage of detected peaks. The peaks that elute at residence time less than ~7 min were together represented as the acidic peaks or AR region.

For mAb X, a 4 mm×250 mm analytical Dionex ProPac WCX-10 column (Dionex, CA) was used along with a Shimazhu HPLC system. The mobile phases were 20 mM MES, pH 6.5 buffer (Mobile phase A) and 20 mM MES, 500 mM NaCl, pH 6.5 buffer (Mobile phase B). A binary gradient (10% B: 0 min; 10-28% B: 1-46 min; 28-100% B: 46-47 min; 100% B: 47-52 min; 100-10% B: 52-53 min; 10% B: 53-58 min) was used with detection at 280 nm. Quantitation was based on the relative area percentage of detected peaks. All peaks eluting prior to the Main Isoform peak were summed as the acidic region, and all peaks eluting after the Main peak were summed as the basic region.

For mAb Y, a 4 mm×250 mm Dionex ProPac analytical WCX-10 column (Dionex, CA) was used on a Shimazhu HPLC system. The mobile phases were 20 mM MES, pH 6.2 (Mobile phase A) and 20 mM MES, 250 mM NaCl, pH 6.2 (Mobile phase B). A binary gradient (1% B: 0-1 min; 1-25% B: 1-46 min; 25-100% B: 46-47 min; 100% B: 47-52 min; 100-1% B: 52-53 min; 1% B: 53-60 min) was used with detection at 280 nm. Column temperature was set at 35° C. Quantitation was based on the relative area percentage of detected peaks. All peaks eluting prior to the Main Isoform peak (but after 2 min retention time) were summed as the acidic region, and all peaks eluting after the Main peak were summed as the basic region.

The levels of aggregates, monomer and fragments in eluate samples were measured using a SEC method for each molecule. For Adalimumab and mAb Y, a TSK-gel G3000SWxL, 5 µm, 125 Å, 7.8×300 mm column (Tosoh Bioscience) was used while a TSK-gel Super SW3000, 4 µm, 250 Å, 4.6×300 mm column (Tosoh Bioscience) was used for mAb X along with an Agilent or a Shimazhu HPLC system. For Adalimumab and mAb X, injections were made under isocratic elution conditions using a mobile phase consisting of 100 mM sodium sulfate and 100 mM sodium phosphate at pH 6.8, and detected with UV absorbance at 214 nm. For mAb Y, the mobile phase consists of 1×PBS at pH 7.4, and elution profile detected with UV absorbance at 280 nm. Quantification is based on the relative area of detected peaks.

An HCP ELISA assay was used to determine the HCP levels in various samples and feeds for all three mAbs.

TABLE 1

Processing conditions for Poros XS one-step displacement chromatography

| Molecule | Displacer | Displacer Conc. (mM) | Equilibration/Wash/Displacing buffer Buffer System | pH | Conductivity (mS/cm) | Loading Conditions | Regeneration |
|---|---|---|---|---|---|---|---|
| Adalimumab | Expell SP1 | 0.5-3 | Tris/Acetate | 6.7-7.8 | 5.4-6.6 | pH ~7.5, ~6 mS/cm | 2M NaCl |
| | | 2-5 | MES/NaCl | 6.1 | 2.1 | pH 6.1, ~2 mS/cm | 0.2M acetic acid & 1M KCl |
| | Protamine Sulfate | 0.25-2 | Tris/Acetate | 6.5-7.5 | 5.6-6.6 | pH 7.5, 5.4-6.3 mS/cm | 2M NaCl, 6M Guanidine HCl |
| mAb X | Expell SP1 | 0.5-2 | Tris/Acetate | 6 | 6.2-6.5 | pH 6, ~6 mS/cm | 2M NaCl |
| | Protamine Sulfate | 0.25-0.5 | Tris/Acetate | 6 | 6.0-6.5 | pH 6, 5.6-6.5 mS/cm | 2M NaCl, 6M Guanidine HCl |
| mAb Y | Expell SP1 | 0.5-1 | Tris/Acetate | 5 | ~6 | pH 5, 6.2 mS/cm | 2M NaCl |

TABLE 2

Processing conditions for Poros XS two-step or linear gradient displacement chromatography

| Molecule | Displacer | Displacement Method | Displacer Concentration (mM) | Buffer System | pH | Conductivity (mS/cm) | Loading Conditions | Regeneration |
|---|---|---|---|---|---|---|---|---|
| Adalimumab | Expell SP1 | Two-step | (1): 0.5 mM, 25 CV; (2): 2 mM, 20 CV | Tris/Acetate | 7 | ~6 | pH 7.5, 6.1 mS/cm | 2M NaCl |
| | Protamine Sulfate | Two-step | (1): 0.25 mM, 10 CV; (2): 2 mM, 10 CV | Tris/Acetate | 7.5 | 5.5 | pH 7.5, 6.1 mS/cm | 2M NaCl, 6M Guanidine HCl |
| | Expell SP1 | Linear Gradient | 0-1 mM over 40 CV | Tris/Acetate | 7 | ~6 | pH 7.5, 6.0 mS/cm | 2M NaCl |
| | Protamine Sulfate | Linear Gradient | 0-1 mM over 40 CV | Tris/Acetate | 7.5 | ~6 | pH 7.5, 5.9 mS/cm | 2M NaCl, 6M Guanidine HCl |
| mAb X | Expell SP1 | Two-step | (1): 0.5 mM, 22 CV; (2): 2 mM, 12 CV | Tris/Acetate | 6 | 6.1 | pH 6, 6.3 mS/cm | 2M NaCl |
| | Protamine Sulfate | Two-step | (1): 0.35 mM, 10 CV; (2): 0.5 mM, 10 CV | Tris/Acetate | 6 | ~6 | pH 6, 6.3 mS/cm | 2M NaCl |

TABLE 3

Processing conditions for Capto MMC one-step displacement chromatography

| Molecule | Displacer | Displacer Concentration (mM) | Equilibration/Wash/Displacing buffer Buffer System | pH | Conductivity (mS/cm) | Loading Conditions | Regeneration | CIP |
|---|---|---|---|---|---|---|---|---|
| Adalimumab | Protamine Sulfate | 0.25-0.5 | Tris/Acetate | 7-7.5 | ~6 | pH 7.5, 5.3-6.1 mS/cm | 2M NaCl, 6M Guanidine HCl | 0.5N NaOH + 0.5M KCl |
| mAb X | Protamine Sulfate | 0.25-0.5 | Tris/Acetate | 7-7.7 | ~6 | pH 7.7, 5.9-6.5 mS/cm | 2M NaCl, 6M Guanidine HCl | |
| mAb Y | Protamine Sulfate | 0.25-0.5 | Tris/Acetate | 5-5.5 | ~6.5 | pH 5.5, 5.2-5.6 mS/cm | 2M NaCl, 6M Guanidine HCl | |

5.1. Displacement Chromatography Performances of Expell SP1™ for Adalimumab on Poros Xs Resin Expell SP1™ is a low molecular weight quaternary ammonium salt that exhibited pronounced displacement effect for Adalimumab on Poros XS resin under selected sets of operating conditions. The feed material used for this set of experiments contained about 20-25% total AR, of which 2-5% was AR1 and 18-20% AR2. The results for this system are shown in the following sections.

A representative, desired displacement chromatographic profile is shown in FIG. 1a (solid line). In this experiment, the column was equilibrated with a pH 7 Tris/acetate buffer (6.4 mS/cm), loaded with a pre-adjusted protein A eluate feed (pH 7.5, 6.3 mS/cm, ~3.4 g/L) to ~40 g/L resin loading level, followed by EQ buffer wash and then displacement process using 1 mM Expell SP1™ in the pH 7 EQ buffer. The extended, square shape UV280 "elution" profile indicated establishing a proper displacement train and thus a degree of separation of the feed components can be realized.

Figure 2:
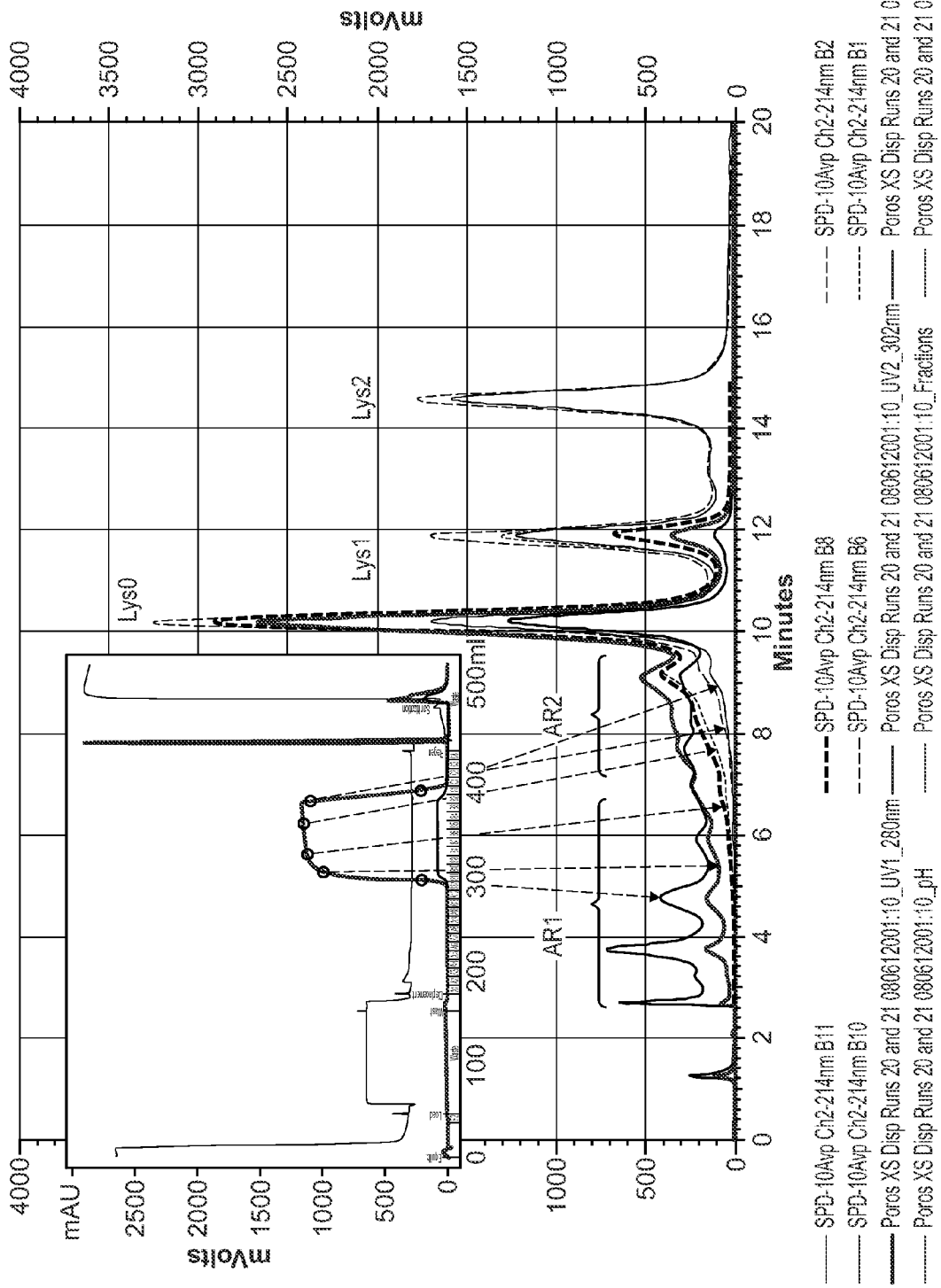
FIG. 2 depicts CEX-HPLC chromatograms of Expell SP1™-displaced Adalimumab sample fractions.

FIG. 2 illustrates the CEX-HPLC chromatograms for several samples taken along this well-established displacement UV trace. Clearly, the variant species were rearranged during the displacement process according to their respective binding affinity to the resin: AR1 was enriched in the foremost of the displacement train followed by AR2, Lys0, Lys 1 and Lys2 in order.

Figure 3:
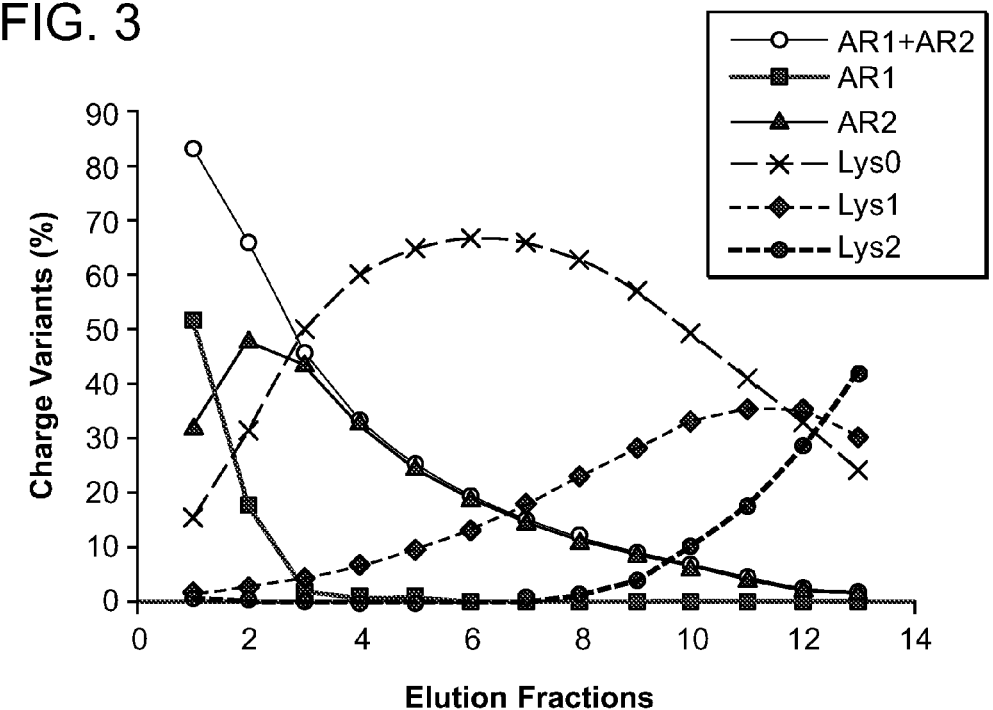
FIG. 3 depicts the separation of Adalimumab charge variants by Poros XS displacement chromatography using Expell SP1™.
Figure 4:
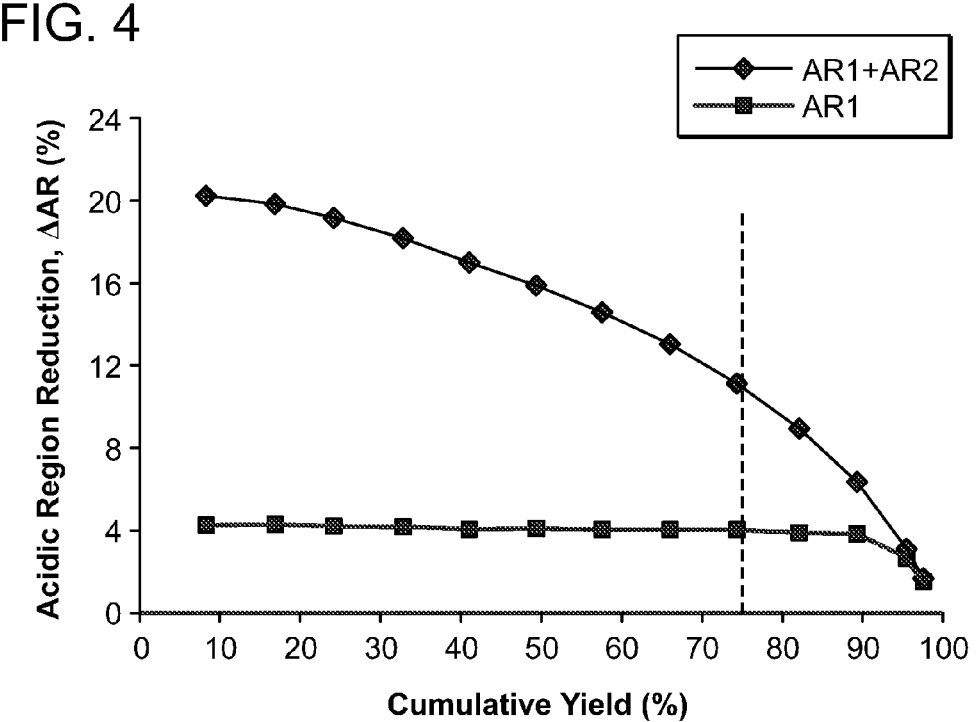
FIG. 4 depicts the reduction of acidic species level in Adalimumab by Poros XS displacement chromatography using Expell SP1™.

FIG. 3 shows the distribution of each variant species in all the collected sample fractions. The acidic species were enriched in the earlier fractions compared to the Lys variants. By excluding those earlier fractions the product pool AR level will be reduced relative to that in the feed. This is reflected in FIG. 4 which plots the reduction of total AR (i.e. AR1+AR2) and AR1 level versus cumulative product yield. At a yield of ~75%, the total AR % was reduced by 11.7% and AR1% by 4.2% under this set of condition.

Figure 1B:
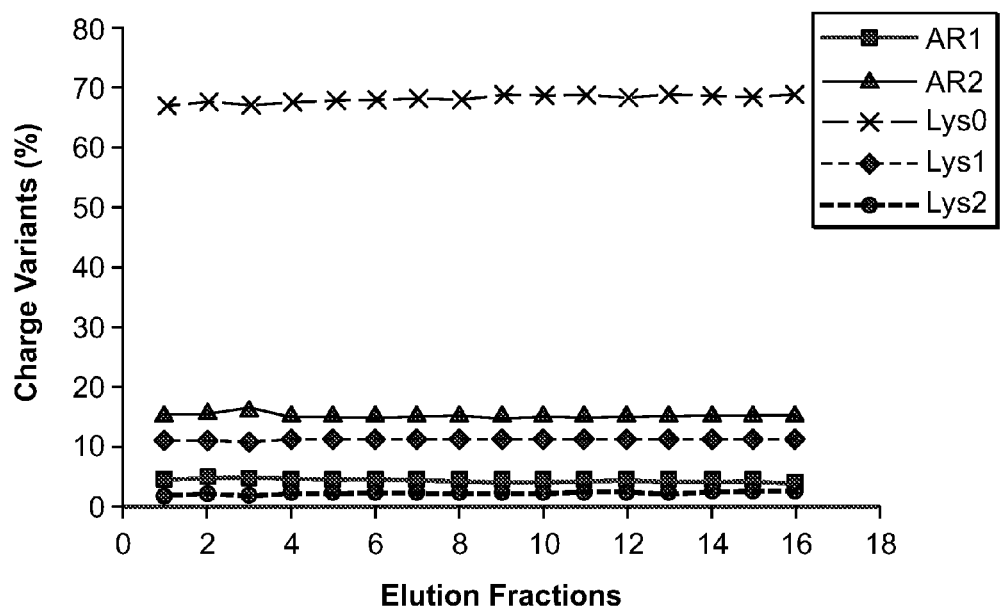
FIG. 1B depicts charge variants distribution in eluate fractions derived from the undesired displacement chromatography process for Adalimumab (Poros XS resin & Expell SP1™).

Varying the processing conditions such as the buffer pH and displacer concentration can modulate the shape of the displacement chromatogram and hence the separation performance. In an extreme case, the chromatogram more or less resembles the typical elution "peak" profile without incurring the separation of variant species (FIGS. 1a and 1b). Interestingly, this occurs at stronger binding conditions; for instance, the conditions corresponding to FIG. 1b is pH 6.1 and ~2 mS/cm for equilibration, loading, wash, and displacement. Without being bond by theory, the lack of variant separation under such conditions may be due to the diminishing difference in binding affinity of each species and thus the selectivity by the displacer.

Figure 5:
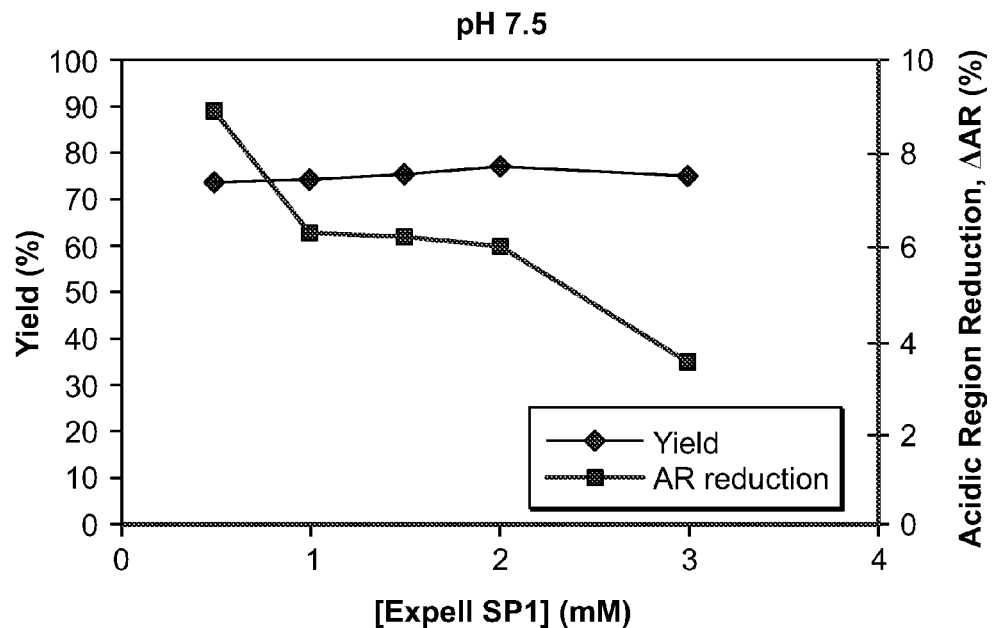
FIG. 5 depicts the effect of Expell SP1™ concentration on acidic species reduction in Adalimumab by Poros XS displacement chromatography.

The effect of Expell SP1™ concentration on Adalimumab AR reduction was measured in pH 7.5 Tris/Acetate buffer, as shown in FIG. 5. The same equilibration/wash and feed loading conditions were used for all the runs here. Increasing Expell SP1™ concentration from 0.5 to 3 mM decreased ΔAR % from 8.9% to 3.5% at similar product yield~75%. Controlling the Expell SP1™ concentration within 2 mM will consistently achieve ≥6% AR % reduction.

Figure 6:
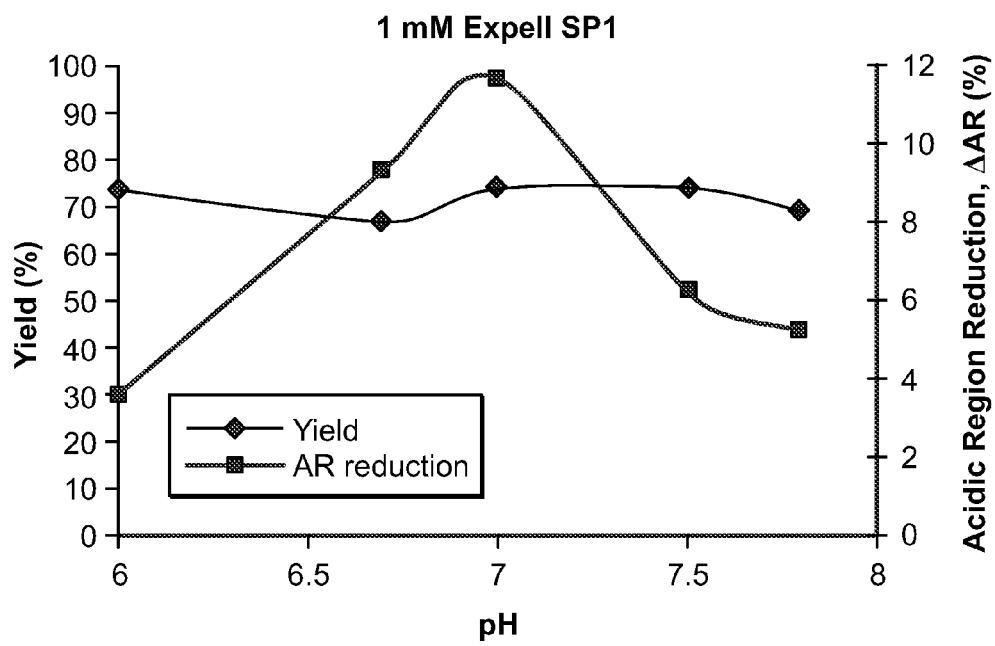
FIG. 6 depicts the effect of pH on acidic species reduction in Adalimumab by Poros XS displacement chromatography using Expell SP1™.

The effect of displacing buffer pH on AR reduction for Adalimumab was measured at 1 mM Expell SP1™ concentration in the Tris/Acetate buffer, as shown in FIG. 6. In this set of experiments, the column was conditioned with an EQ buffer at the respective displacing buffer pH, and then loaded with protein feed at pH 7.5 and ~6 mS/cm followed by a brief EQ buffer wash before starting the displacement step. The buffer pH significantly impacts AR clearance in pH range of 6-8. At similar yield (~75%), the maximal reduction in AR level (~12%) is seen at pH 7. Despite such pH-dependency, the majority of the conditions here (pH 6.5 to 7.8) gave at least 5% AR removal in final product pool.

In the aforementioned experiments, one displacing buffer was used to achieve the protein variant separation. It was observed that, relatively lower displacer concentration gives better separation but tends to elongate the process due to substantial increase in the required displacing buffer volume. For instance, when using 0.5 mM Expell SP1™ in a pH 7 displacing buffer (Table 1), the displacement phase requires 44 column volumes (CV) of this buffer for completion. To accelerate the operation without affecting the acidic species separation, a two-step displacement process was explored at this pH condition. In the example provided here, the displacement process was started with 0.5 mM Expell SP1™ at pH 7 and continued for 25 CV, followed by 20 CV of 2 mM Expell SP1™ solution at the same pH. Under such conditions, the protein displacement profile was completed in a total of 33 CV which is 25% less than that required for one-step displacement process, thus significantly shortening the process.

Figure 7:
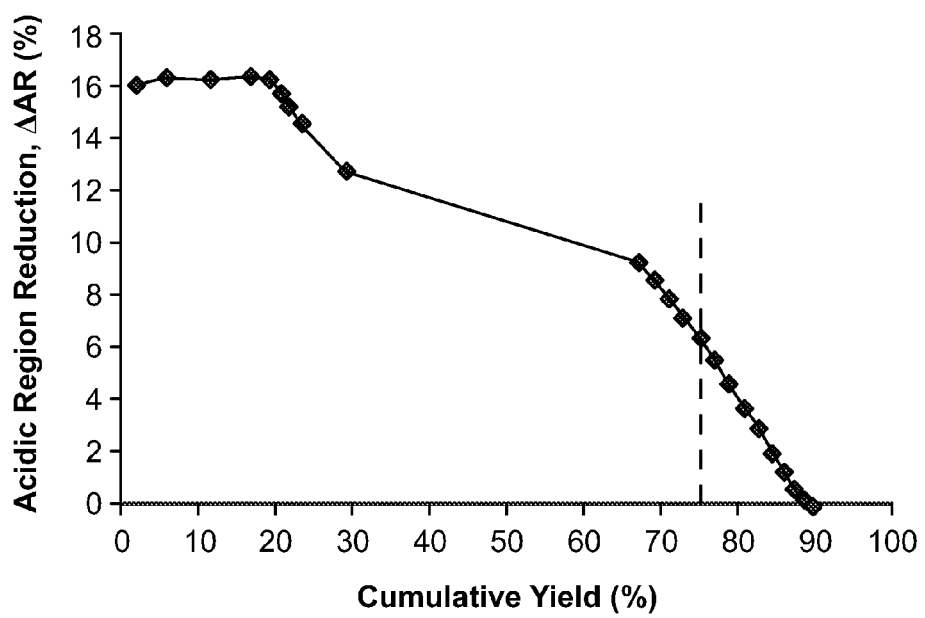
FIG. 7 depicts the reduction of acidic species level in Adalimumab by Poros XS two-step displacement chromatography using Expell SP1™.

FIG. 7 shows the reduction of AR % versus product yield for the aforementioned two-step displacement run. The net total AR level in product pool was reduced by 6.6% at ~75% yield. In contrast to the conventional use of a single displacing solution consisting of a single displacer at a defined concentration, herein the AR clearance was achieved by excluding the AR-enriched early fractions as induced by 0.5 mM Expell SP1™ displacement, while the higher Expell SP1™ concentration was used to accelerate the displacement of the remainder proteins off the solid phase. In light of this unexpected similar product quality and yield results, step-gradient displacement schemes are considered to be advantageous over conventional strategies.

Besides the two-step displacement scheme, a linear gradient displacement method was also tested for the Adalimumab charge variant separation. As detailed in Table 2, after the feed loading at pH 7.5 (~6 mS/cm), the column was briefly washed with the equilibration buffer (pH 7, ~6 mS/cm) and then started with a 40 CV linear gradient from the EQ buffer to a 1 mM Expell SP1™ displacing buffer (which was made from the EQ buffer). Under such condition, the displacement profile matured within this 40 CV gradient. The product eluate was pooled by excluding the first a few fractions. In this case, the net AR % decreased by 6.8% at a product recovery of 72%.

Figure 8:
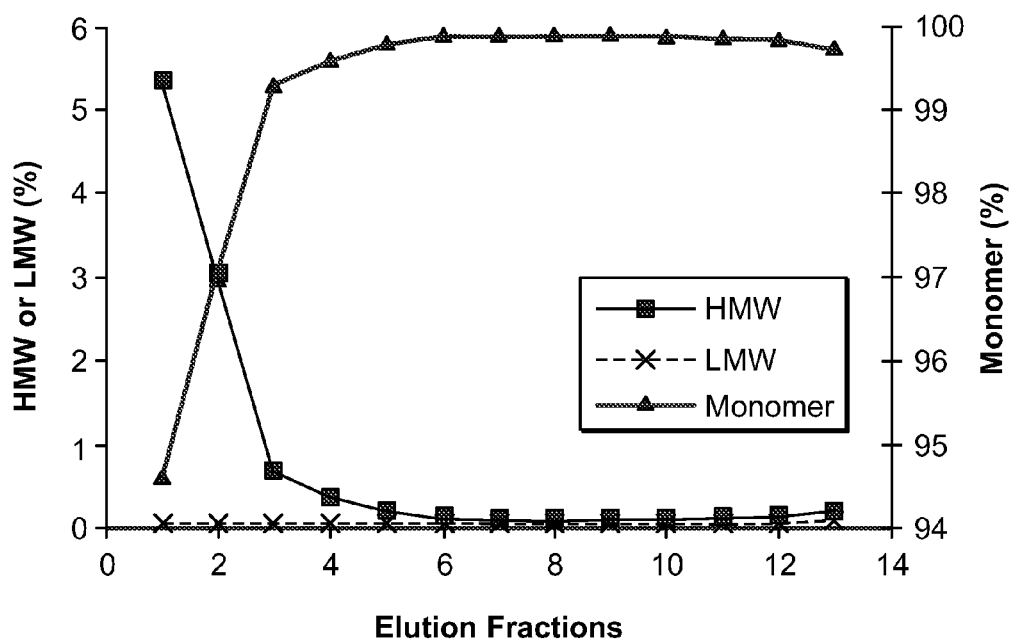
FIG. 8 depicts the separation of Adalimumab size variants by Poros XS displacement chromatography using Expell SP1™.

Apart from acidic species, other product- or process-related impurities can be effectively separated by Poros XS displacement chromatography using Expell SP1™ as the displacer. FIG. 8 shows the separation of aggregates, monomer and fragments in Adalimumab sample fractions obtained from a one-step displacement experiment using 1 mM Expell SP1™, pH 7 buffer. It should be noted that the last two fractions from this run were not collected, therefore the increased aggregate levels at the end of the displacement train was not fully exemplified here. Interestingly, the early fractions which contained elevated acidic species also showed enriched aggregates, indicating that this population of aggregates may consist of more acidic species, or the acidic species has higher propensity to form aggregates. As summarized in Table 4, the aggregate level in the product pool (at ~75% yield) was reduced from the feed level 1.16% to 0.11% and the fragment level down to 0.04% along with significant reduction in the AR concentration. In addition to the standard method, the linear gradient displacement run also showed aggregate reduction from the feed level of 0.9% to about 0.2% in final product.

Figure 9:
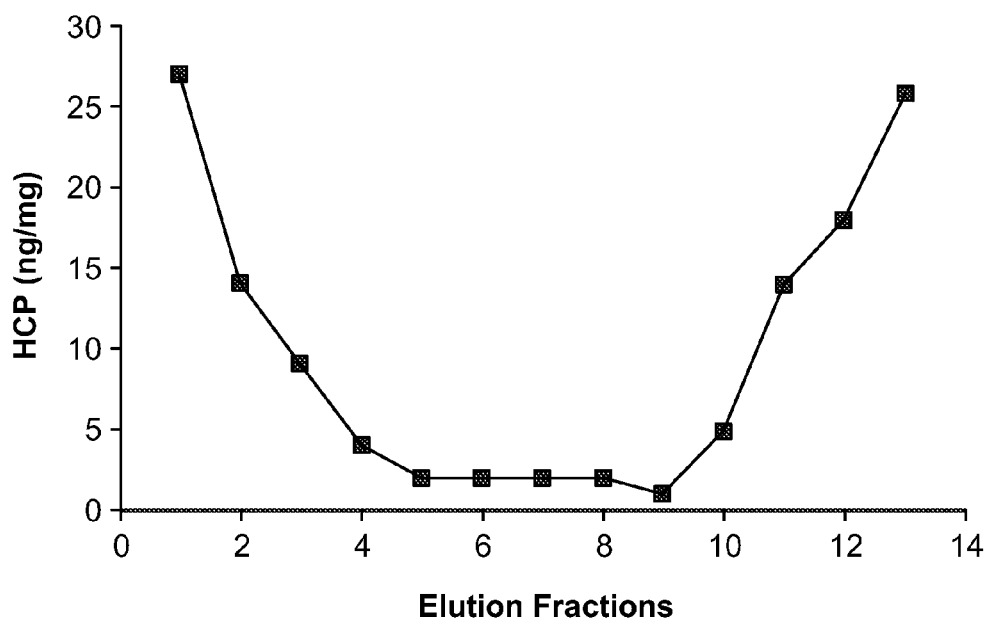
FIG. 9 depicts the separation of HCP in Adalimumab by Poros XS displacement chromatography using Expell SP1™.

FIG. 9 shows the distribution of HCP in the Adalimumab displacement train coming off the Poros XS column. Relatively higher level of HCP was observed at both ends of the train, due to their diverse charge characteristics and associated binding strength. The final product pool HCP level was reduced to 5 ng/mg from the starting feed, representing approximately 50-fold reduction.

TABLE 4

Step yield & product quality in Adalimumab before and after Poros XS displacement chromatography using Expell SP1 ™ (pH 7, 1 mM Expell SP1 ™)

| | Yield % | AR1 % | AR2 % | Lys Sum % | HMW % | Monomer % | LMW % | HCP (ng/mg) |
|---|---|---|---|---|---|---|---|---|
| Feed | — | 4.3 | 17.8 | 77.9 | 1.16 | 98.57 | 0.27 | 267 |
| Product pool | 74 | 0.1 | 10.3 | 89.6 | 0.11 | 99.85 | 0.04 | 5 |

5.2. Displacement Chromatography Performance of Protamine Sulfate for Adalimumab on Poros Xs Resin Protamine sulfate, a cationic peptide with molecule weight~5.1 kD, was also evaluated as a cation exchange displacer for Adalimumab on Poros XS resin under various operating conditions. The feed material used for this set of experiments contained about 17-24% total AR, of which 3-6% was AR1 and 14-19% AR2. The results for this system are illustrated in the following sections.

Figure 10:
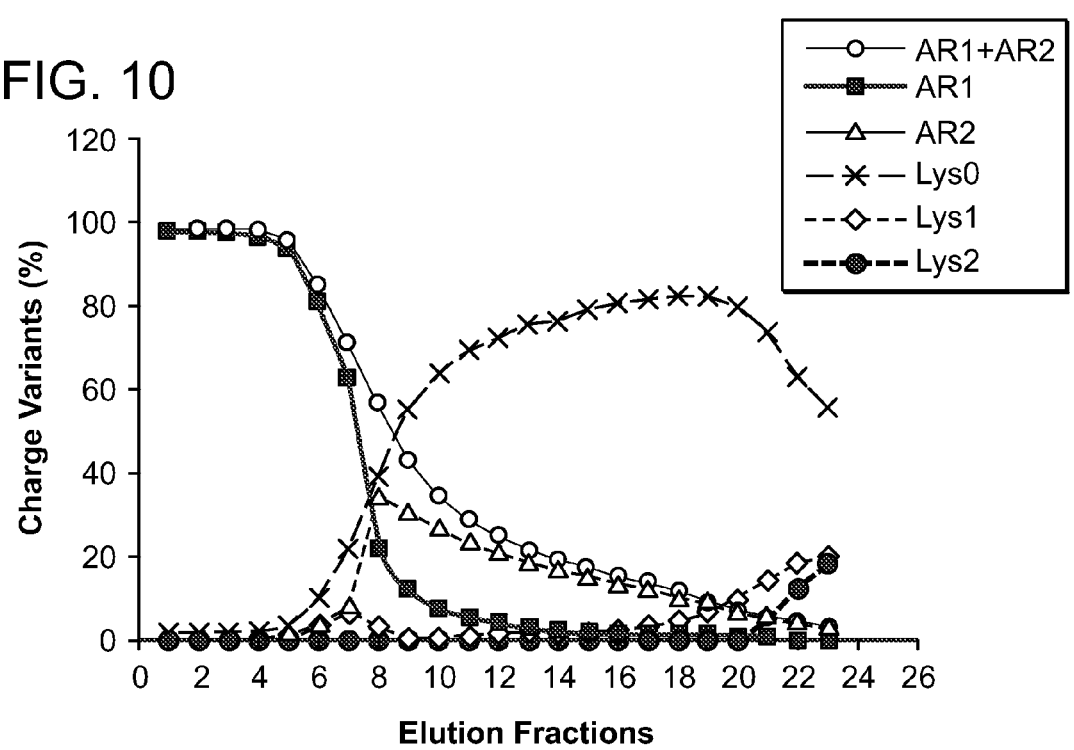
FIG. 10 depicts the separation of Adalimumab charge variants by Poros XS displacement chromatography using protamine sulfate.
Figure 11:
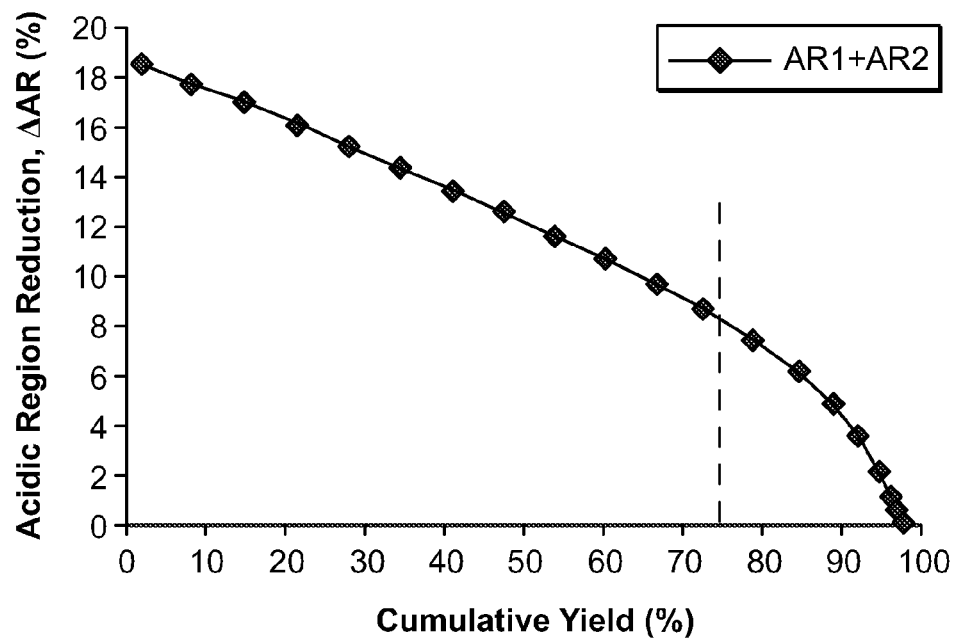
FIG. 11 depicts the reduction of acidic species in Adalimumab by Poros XS displacement chromatography using protamine sulfate.

FIG. 10 shows the distribution of charge variant species in sample fractions collected from a well established displacement process induced by protamine sulfate. In this experiment, the column was equilibrated with a pH 7.5 Tris/acetate buffer (5.6 mS/cm), loaded with a pre-adjusted protein A eluate feed (pH 7.5, 5.4 mS/cm, 5.2 g/L) to 39 g/L resin loading level, followed by a brief EQ buffer wash and then displacement process using 0.5 mM protamine sulfate dissolved in the pH 7.5 EQ buffer. Similar to the Expell SP1™ displacement profile (FIG. 3), the charge variants were enriched at different locations of the displacement train and were peaked in the order of AR1, AR2, Lys0, Lys1 and Lys2. The cumulative AR % reduction as a function of product yield is illustrated in FIG. 11. A 6-8% decrease in the total AR level can be obtained at a yield of 75-85% under this set of condition. The actual levels of AR1, AR2 and total Lys (i.e. Lys0+Lys 1+Lys2) for the feed and the final product pool are shown in Table 5.

Figure 12:
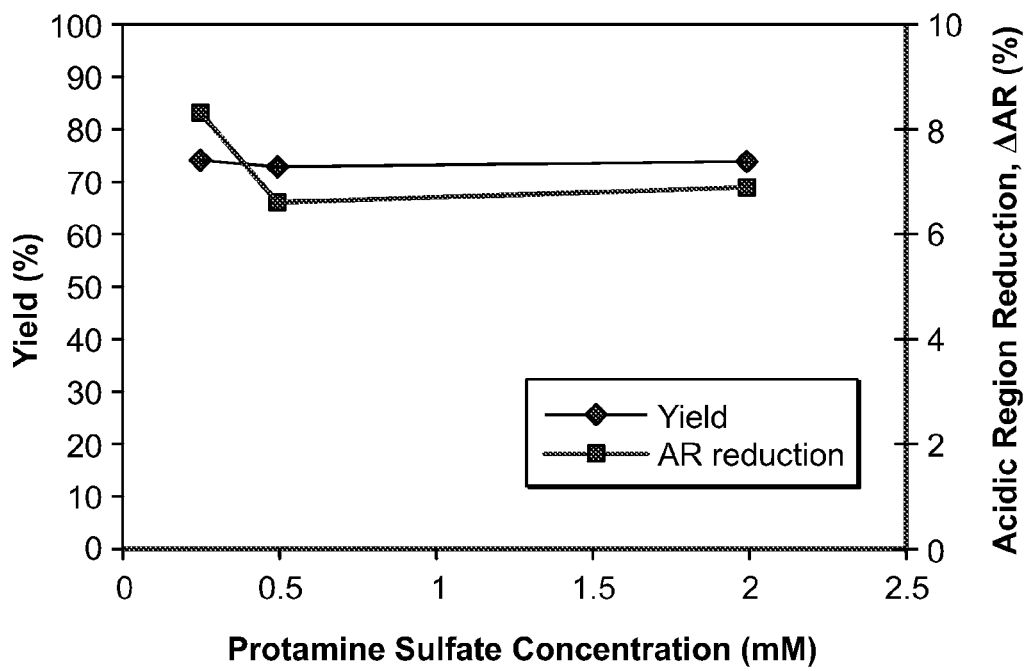
FIG. 12 depicts the effect of protamine sulfate concentration on acidic species reduction in Adalimumab by Poros XS displacement chromatography.

The effect of protamine sulfate concentration on Adalimumab AR reduction was measured in pH 7.5 Tris/Acetate buffer, as shown in FIG. 12. The same equilibration/wash and feed loading conditions as described above were used for all the runs here. At similar yield (~75%), the total AR % was reduced by approximately 7-8% when using 0.25 to 2 mM protamine sulfate. This broad concentration range reflects the robustness of charge variant separation by protamine sulfate displacement process.

Figure 13:
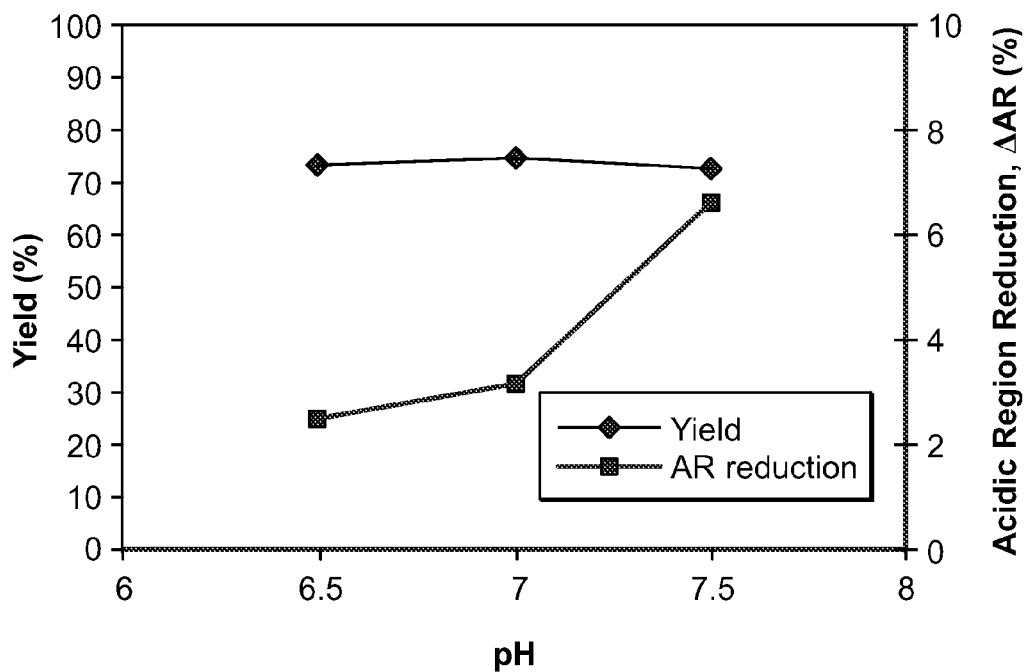
FIG. 13 depicts the effect of pH on acidic species reduction in Adalimumab by Poros XS displacement chromatography using protamine sulfate.

The effect of displacing buffer pH on AR clearance for Adalimumab was measured at 0.5 mM protamine sulfate concentration in Tris/Acetate buffer. In this set of experiments, the column was conditioned with an EQ buffer at the respective displacing buffer pH, loaded with protein feed at pH 7.5 and ~6 mS/cm followed by a brief EQ buffer wash before starting the displacement phase. As shown in FIG. 13, the extent of AR reduction increases significantly as pH varies from 6.5 to 7.5. Over 6% decrease in AR level can be achieved at pH 7.5 with a product yield~75%.

Figure 14:
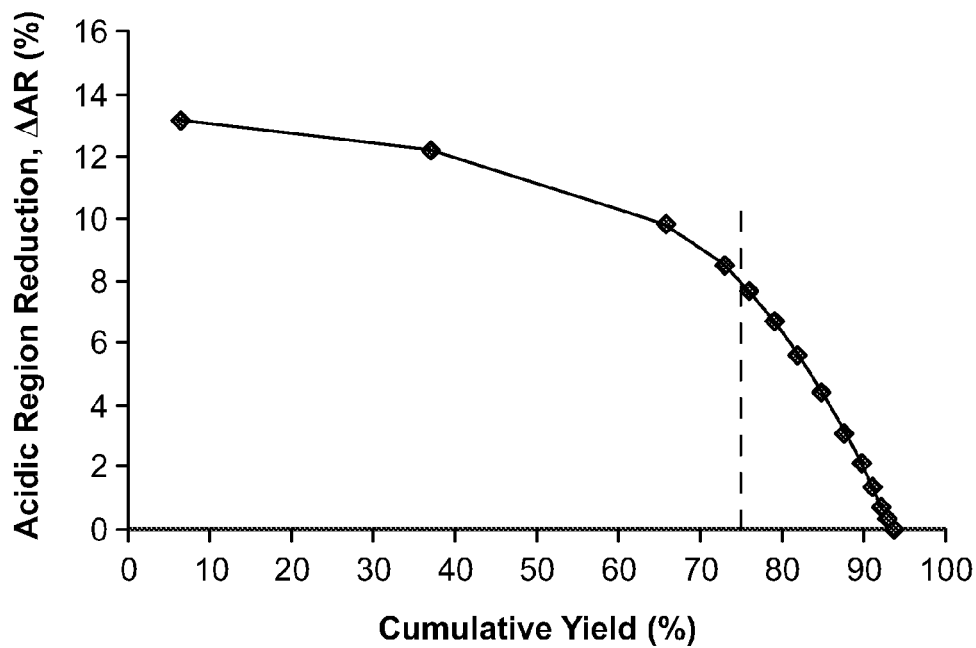
FIG. 14 depicts the reduction of acidic species in Adalimumab by Poros XS two-step displacement chromatography using protamine sulfate.

The two-step displacement scheme was also tested with protamine sulfate. In one experiment, the displacement process consists of 10 CV of 0.25 mM protamine and 10 CV of 2 mM protamine at pH 7.5 (Table 2). The protein displacement profile was completed in a total of 13 CV, which is about 11 CV or almost 2 fold shorter than that in the one-step displacement process with 0.25 mM protamine sulfate. The reduction of AR % versus product yield is shown in FIG. 14. The total AR level in product pool were reduced by ~8% at ~75% yield, which is comparable to that achieved by the one-step displacement process using 0.25 mM protamine sulfate.

Figure 15:
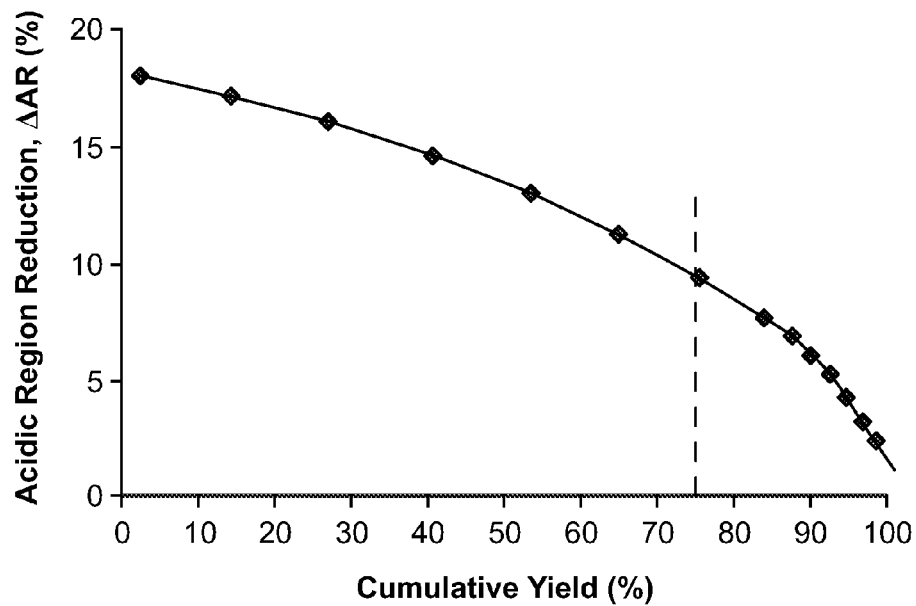
FIG. 15 depicts the reduction of acidic species in Adalimumab on Poros XS using protamine sulfate linear gradient displacement chromatography.

The linear gradient displacement scheme was also evaluated with protamine sulfate on Poros XS resin for Adalimumab charge variant separation. As summarized in Table 2, after the feed loading at pH 7.5 (5.9 mS/cm), the column was briefly washed with the equilibration buffer (pH 7.5, ~6 mS/cm) and then started with a 40 CV linear gradient from the EQ buffer to a 1 mM protamine sulfate displacing buffer (which was made from the EQ buffer). FIG. 15 shows the cumulative ΔAR % versus yield from this run. At a product yield of 75.6%, the total AR % was reduced from the feed level of 21.3% to 12.1%.

Figure 16:
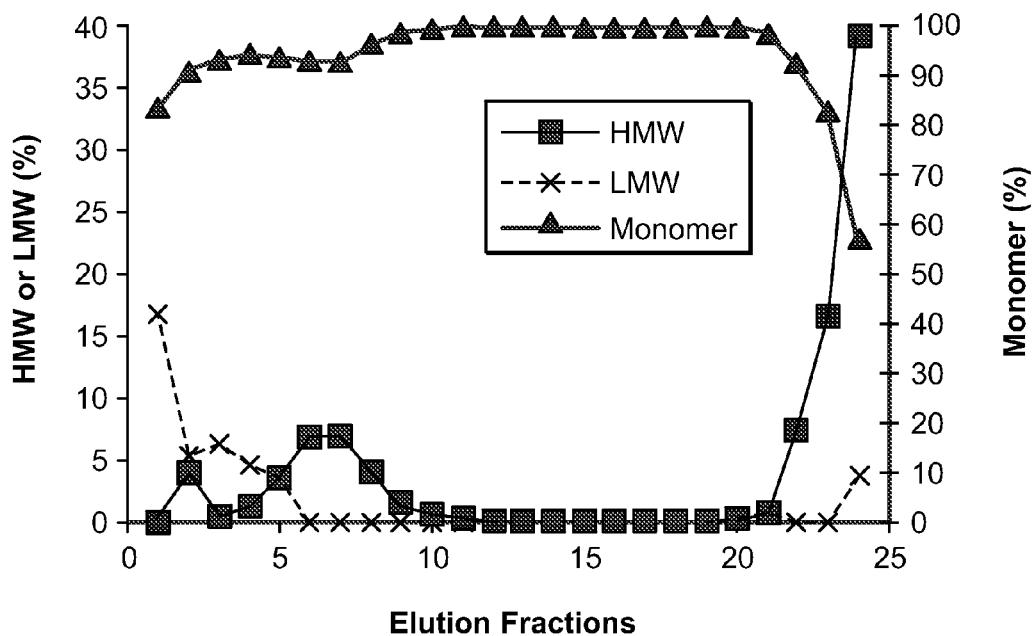
FIG. 16 depicts the separation of Adalimumab size variants by Poros XS displacement chromatography using protamine sulfate.

Protamine sulfate displacement chromatography also demonstrated significant clearance of aggregates, fragments and HCP. FIG. 16 exemplifies the size variant profiles of Adalimumab from the same experiment described above (i.e., 0.5 mM protamine sulfate, pH 7.5, one-step displacement run). As expected, the fragments were mostly enriched at the front while the aggregates primarily resided at the back of the train. Similar to that shown in FIG. 8, a subpopulation of the aggregates was also observed in the displacement front; in addition, a portion of fragments was noticed at the tail. Table 5 compares the levels of aggregates, fragments and HCP in final product pool (at ~75% yield) relative to the feed.

TABLE 5

Step yield & product quality in Adalimumab before and after Poros XS displacement chromatography using protamine sulfate

| | Yield % | AR1 % | AR2 % | Lys Sum % | HMW % | Monomer % | LMW % | HCP (ng/mg) |
|---|---|---|---|---|---|---|---|---|
| Feed | — | 4.1 | 16.9 | 79.0 | 0.8 | 98.0 | 1.2 | 153 |
| Product pool | 73 | 1.3 | 13.1 | 84.7 | 0.3 | 99.6 | 0.1 | 14 |

5.3. Displacement Chromatography Performance of Expell SP1™ for mAb X on Poros Xs Resin The displacement separation performance of Expell SP1™ was assessed for mAb X on the Poros XS resin. A purified mAb X drug substance was used in this study, which contained about 16-17% acidic species and 12-14% basic species.

Figure 17:
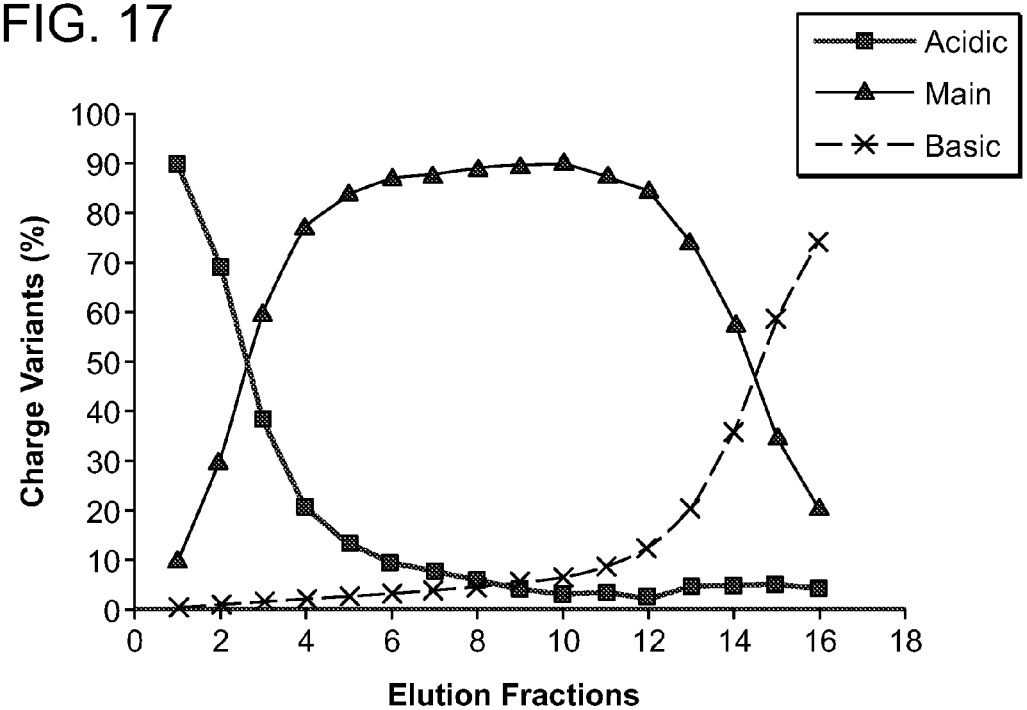
FIG. 17 depicts the separation of mAb X charge variants by Poros XS displacement chromatography using Expell SP1™.
Figure 18:
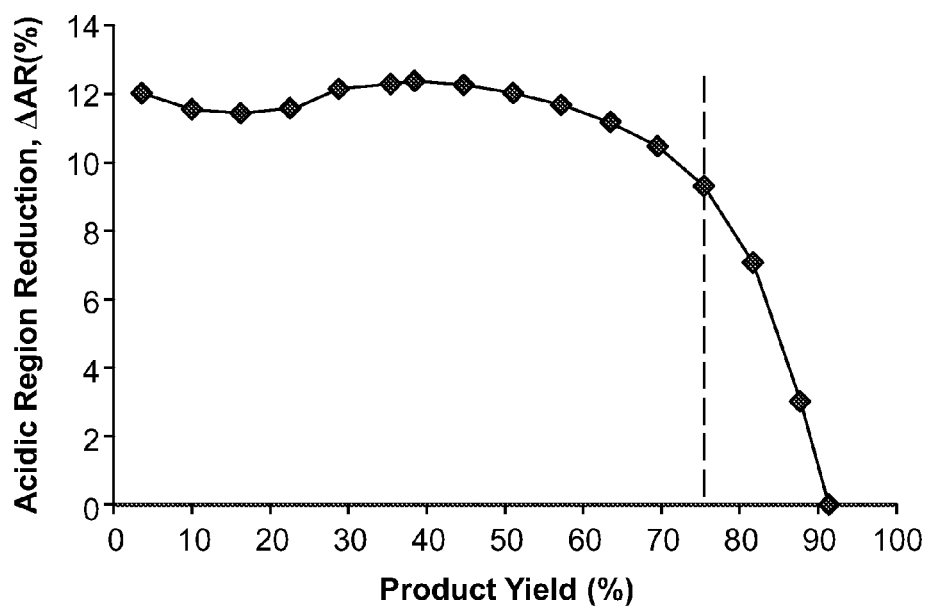
FIG. 18 depicts the reduction of acidic species in mAb X by Poros XS displacement chromatography using Expell SP1™.

A representative set of mAb X charge variant separation profiles are shown in FIGS. 17 and 18. In this experiment, the Poros XS column was loaded with 40 g/L of mAb X at pH 6, 6 mS/cm Tris/Acetate binding condition, and was displaced using 1 mM Expell SP1™ in a pH 6, ~6 mS/cm buffer. The specific conditions are detailed in Table 1. Pronounced enrichment and separation of acidic, main and basic species were achieved, with AR % reduced by 9.4% at 76% yield.

Figure 19:
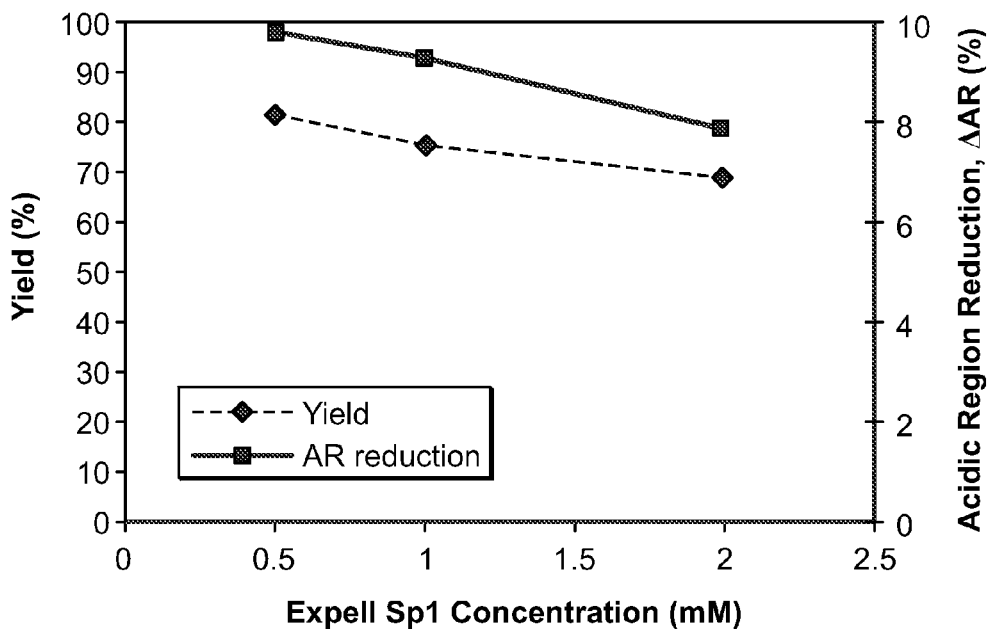
FIG. 19 depicts the effect of Expell SP1™ concentration on acidic species reduction in mAb X by Poros XS displacement chromatography.

The effect of Expell SP1™ concentration on AR reduction for mAb X was measured in the pH 6 Tris/Acetate buffer. As shown in FIG. 19, increasing the Expell SP1™ concentration from 0.5 to 2 mM decreased the ΔAR % for mAb X from 9.8% at 81% yield to 7.9% at 69% yield.

Figure 20:
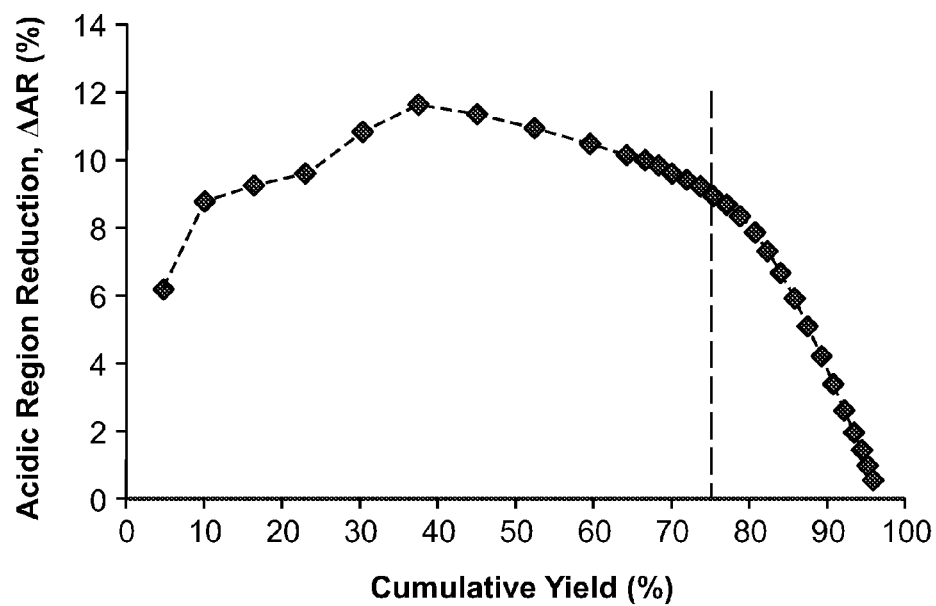
FIG. 20 depicts the reduction of acidic species in mAb X by Poros XS two-step displacement chromatography using Expell SP1™.

The two-step displacement scheme was evaluated for mAb X. As shown in Table 2, the displacement process comprised of 22 CV of 0.5 mM Expell SP1™ and 12 CV of 2 mM Expell SP1™ at pH 6. The protein displacement profile was completed within 30 CV of total displacing buffer volume, which was 30% less than that required for one-step displacement separation. The reduction of AR % versus product yield is shown in FIG. 20. The total AR % in product pool was reduced by ~9% at ~75% yield, again comparable to that obtained with one-step displacement process using 0.5 mM Expell SP1™ buffer.

5.4. Displacement Chromatography Performance of Protamine Sulfate for mAb X on Poros Xs Resin Protamine sulfate was also evaluated for separating acidic species for mAb X on Poros XS resin. The feed material for this set of experiments contained about 12-16% acidic and 12-13% basic species. The results for this system are shown in the following sections.

Figure 21:
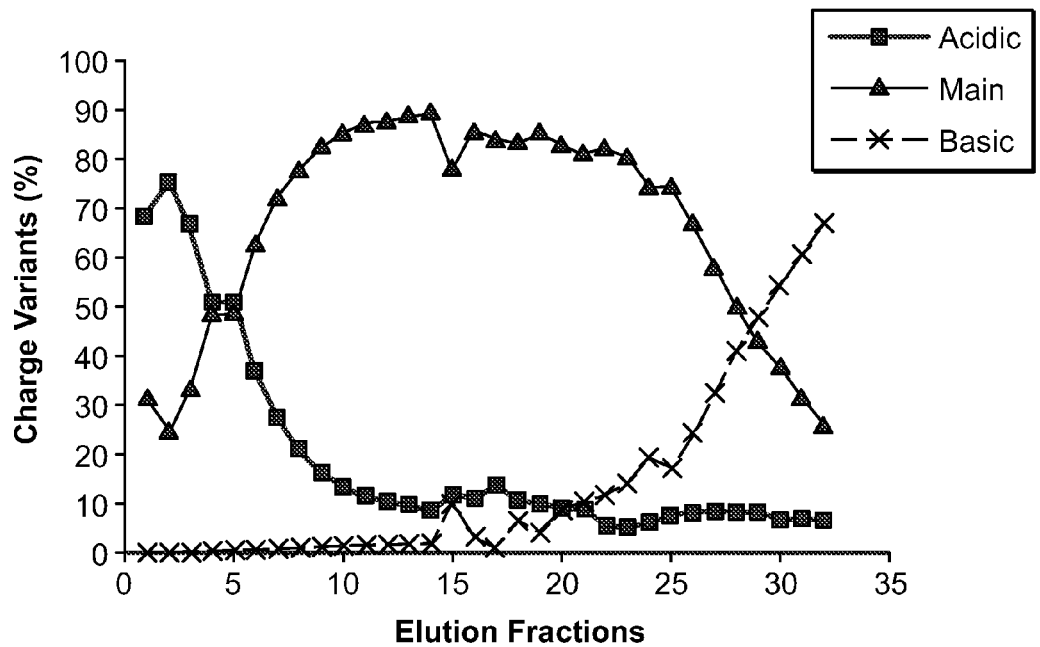
FIG. 21 depicts the separation of mAb X charge variants by Poros XS displacement chromatography using protamine sulfate.
Figure 22:
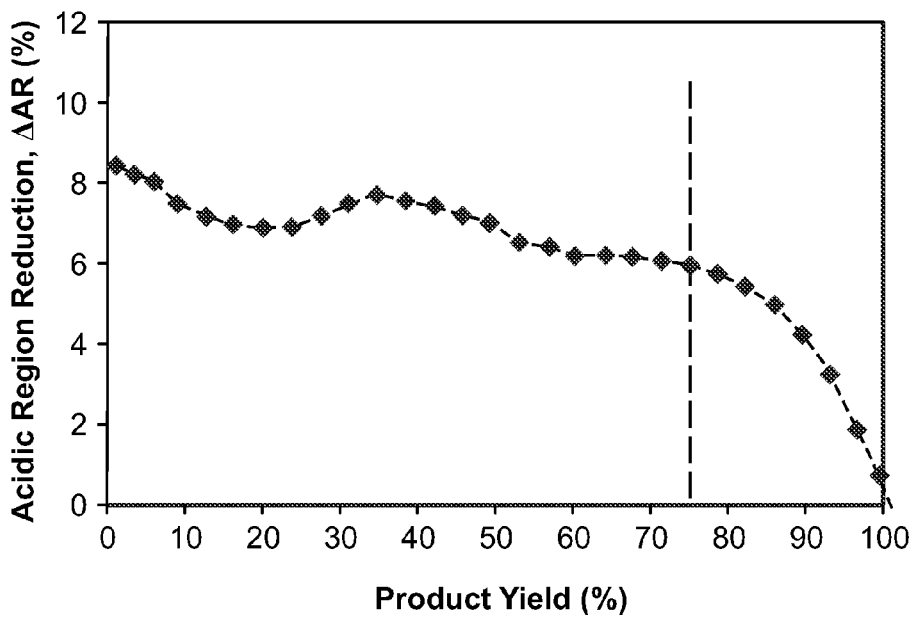
FIG. 22 depicts the reduction of acidic species in mAb X by Poros XS displacement chromatography using protamine sulfate.

A representative set of variant separation profiles are shown in FIGS. 21 and 22. In this experiment, the Poros XS column was loaded with ~36 g/L of mAb X at pH 6, 6.5 mS/cm binding condition, and was displaced using 0.25 mM protamine sulfate in a pH 6, 6.5 mS/cm Tris/Acetate buffer. The specific conditions are detailed in Table 1. Pronounced enrichment and separation of acidic, main and basic species were achieved, with AR level reduced by 6% at 75% yield.

Figure 23:
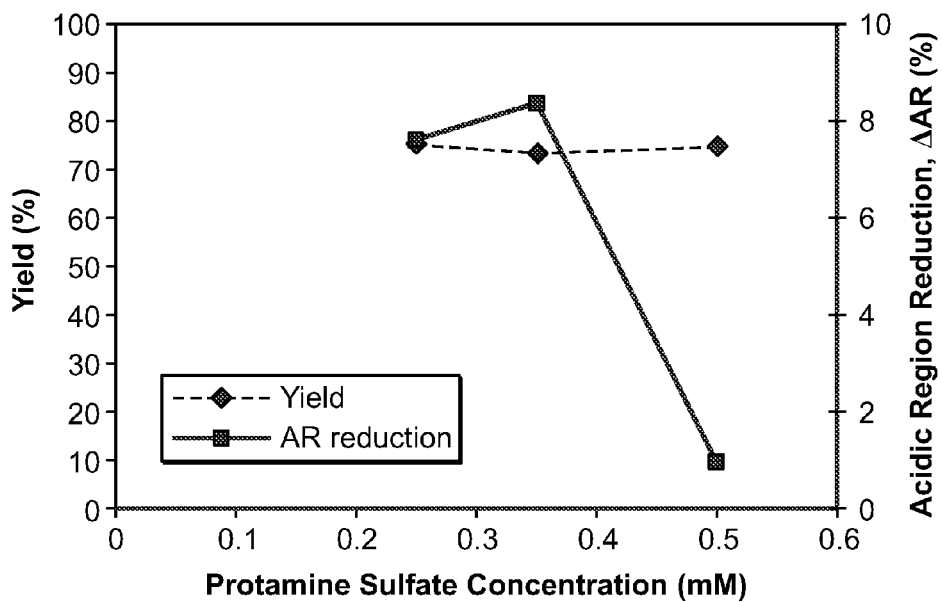
FIG. 23 depicts the effect of protamine sulfate concentration on acidic species reduction in mAb X by Poros XS displacement chromatography.

The effect of protamine sulfate concentration on mAb X AR reduction was measured in a pH 6 Tris/Acetate buffer, as shown in FIG. 23. In this case, the protamine sulfate concentration strongly affects the AR clearance in a relatively small protamine concentration range (i.e. from 0.35 to 0.5 mM). Nevertheless, over 8% of AR reduction can be achieved at pH 6 for mAb X at acceptable yield (≥70%).

Figure 24:
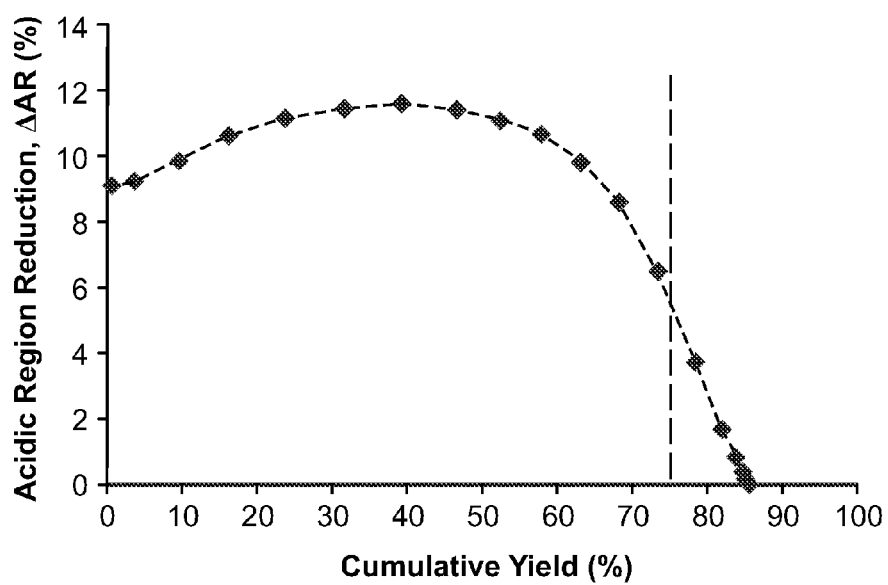
FIG. 24 depicts the reduction of acidic species in mAb X by Poros XS two-step displacement chromatography using protamine sulfate.

The two-step displacement scheme was evaluated for mAb X with protamine sulfate. In this experiment, the displacement process comprised of 10 CV of 0.35 mM Expell and 10 CV of 0.5 mM Expell at pH 6 (see Table 2). The protein displacement profile was completed in ~15 CV of total displacing buffer volume, representing ~26% reduction of buffer volume relative to the one-step displacement operation. The reduction of AR % versus product yield is shown in FIG. 24. The product pool AR level was reduced by ~6% at ~75% yield.

Figure 25:
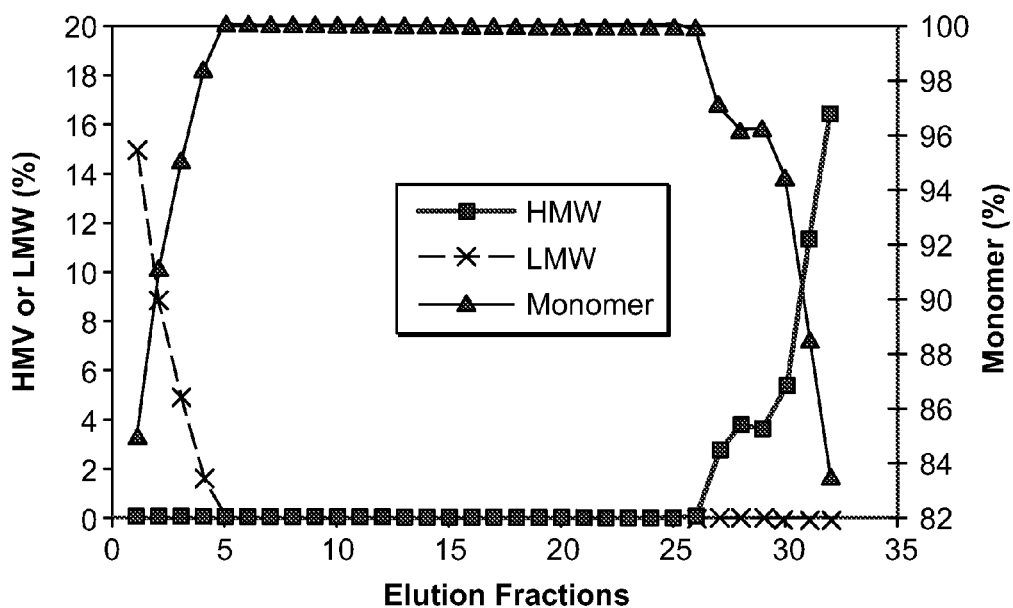
FIG. 25 depicts the separation of mAb X size variants by Poros XS displacement chromatography using protamine sulfate.

The mAb X BDS has about 0.74% of aggregates, which can be further reduced during the protamine sulfate displacement process. FIG. 25 shows the size variant profiles of mAb X as displaced by a 0.25 mM protamine sulfate, pH 6 buffer (i.e., the one-step displacement run shown in FIGS. 21 and 22). The aggregates were all enriched at the end of the displacement train, which differs from the observations with Adalimumab. Using the same product pooling strategy based on AR reduction, the monomer level was enhanced to 99.9% (Table 6).

TABLE 6

Step yield & product quality in mAb X before and after Poros XS displacement chromatography using protamine sulfate

| | Yield % | Acidic % | Main % | HMW % | Monomer % |
|---|---|---|---|---|---|
| Feed | — | 12.3 | 75.7 | 0.7 | 99.3 |
| Product pool | 79 | 4.7 | 80.8 | 0.1 | 99.9 |

5.5. Displacement Chromatography Performance of Expell SP1™ for mAb Y on Poros Xs Resin The displacement separation performance of Expell SP1™ was further assessed for mAb Y on Poros XS resin. The mAb Y has a pI of 7-7.5, much lower than Adalimumab and mAb X. An mAb Y protein A eluate was used in this study, which contained about 22% acidic species and 15% basic species.

Figure 26:
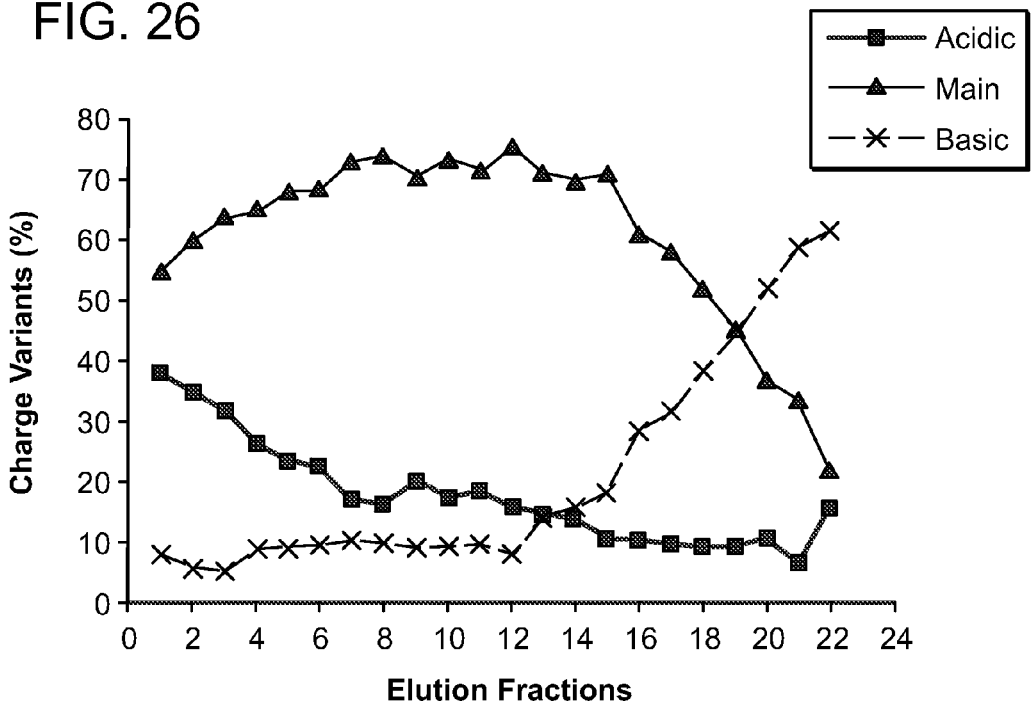
FIG. 26 depicts the separation of mAb Y charge variants by Poros XS displacement chromatography using Expell SP1™.
Figure 27:
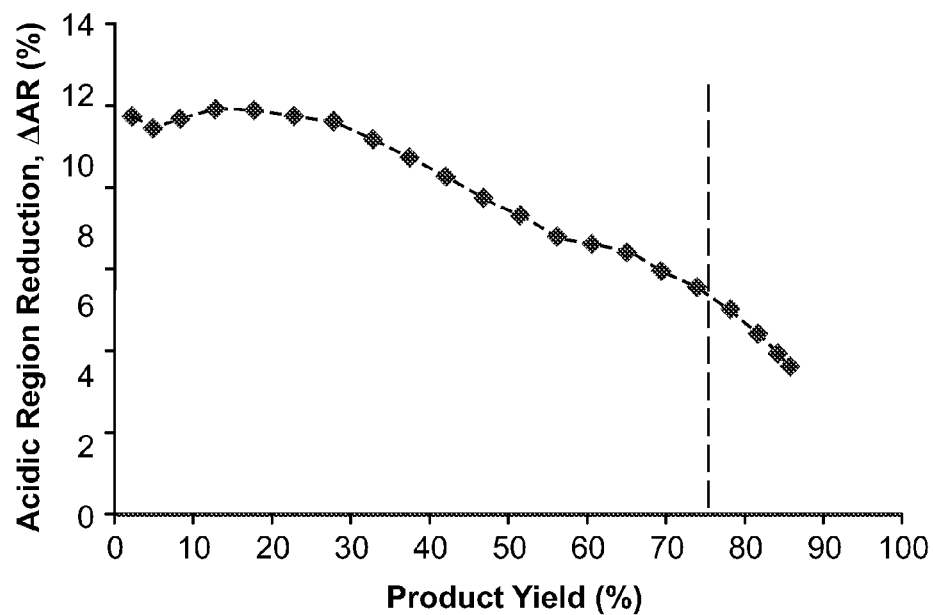
FIG. 27 depicts the reduction of acidic species in mAb Y by Poros XS displacement chromatography using Expell SP1™.

An appropriate set of displacement conditions for mAb Y is shown in Table 1. The equilibration, wash and displacement buffers are all at pH 5 with conductivity around 6 mS/cm. The 0.5 mM Expell SP1™ buffer generated the desired displacement profile. The sample fractions from this run were analyzed by cation exchange HPLC. FIGS. 26 and 27 indicate the distribution of charge variant species and the cumulative ΔAR % versus product yield, respectively. A 6.6% decrease in AR % was observed at 74% yield under such condition.

5.6. Displacement Chromatography Performance of Protamine Sulfate for Adalimumab on Capto MMC (Multimodal) Resin Capto MMC™ is a mixed mode resin based on weak cation-exchange and hydrophobic interaction mechanism. Its capability for acidic species and aggregates removal by displacement chromatography was assessed here. The Adalimumab feed material for this set of experiments contained about 20-21% total AR. The results for protamine sulfate system are shown in the following sections.

Figure 28:
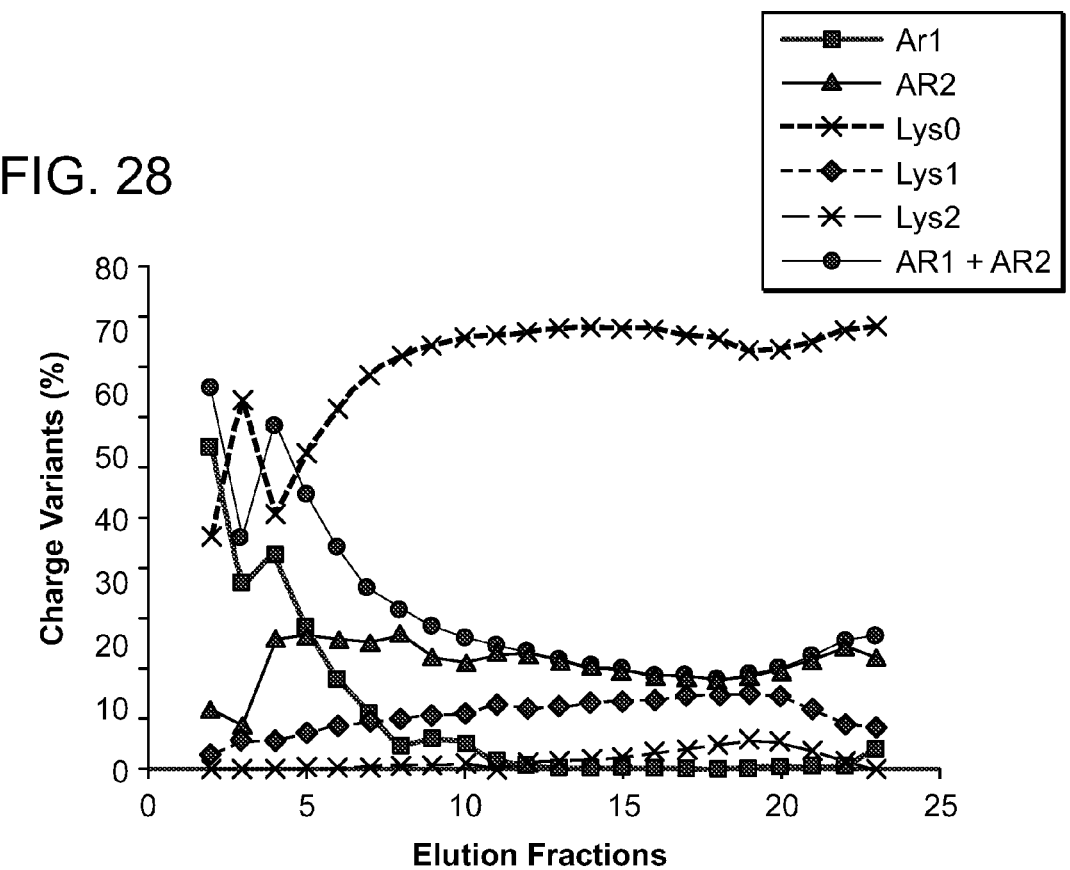
FIG. 28 depicts the separation of Adalimumab charge variants by Capto MMC displacement chromatography using protamine sulfate.
Figure 29:
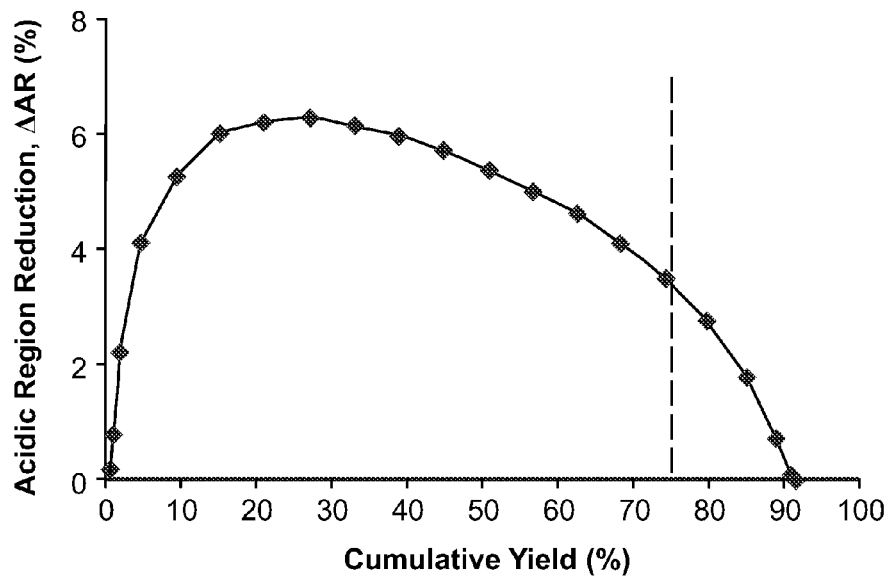
FIG. 29 depicts the reduction of acidic species in Adalimumab by Capto MMC displacement chromatography using protamine sulfate.

A representative set of variant separation profiles are shown in FIGS. 28 and 29. In this experiment, the Capto MMC column was equilibrated with a 140 mM Tris/acetate, pH 7 buffer (~5.7 mS/cm), loaded with ~34 g/L of Adalimumab at pH 7.5 and 5.3 mS/cm binding condition, briefly washed with EQ buffer and then displaced with 0.35 mM protamine sulfate in the pH 7 EQ buffer. A typical displacement chromatogram was generated under such experimental condition. As shown in FIG. 10, Capto MMC also showed enrichment of each variant in the train, yielding total AR reduction of ~4% at ~75% yield. The shape of the ΔAR % versus yield curve (FIG. 29) differs from that given by the Poros XS resin, possibly due to stronger binding of each protein species (related to secondary mode of interaction) by this mixed mode ligand.

The buffer pH and protamine sulfate concentrations were varied to assess the overall AR clearance by Capto MMC displacement chromatography. Table 7 summarized the results for three runs. Overall, 3-5% of AR reduction can be achieved for Adalimumab when using protamine sulfate as a displacer for Capto MMC resin.

TABLE 7

AR removal for Adalimumab by Capto MMC displacement chromatography using protamine sulfate

| Run No. | EQ/Displacing buffer pH | Load pH | Protamine Conc. (mM) | Yield (%) | ΔAR % |
|---|---|---|---|---|---|
| 1 | 7 | 7 | 0.5 | 75 | 3.1 |
| 2 | 7 | 7.5 | 0.35 | 75 | 4.0 |
| 3 | 7.25 | 7.5 | 0.25 | 78 | 5.2 |

The clearance of aggregates by Capto MMC displacement chromatography is illustrated in Table 8. The same operating conditions as described for obtaining the results in Table 7 were used here. The product pool monomer level was enhanced from 98.8% in the feed to 99.4% with aggregates reduced from 1.0% to 0.5%.

TABLE 8

Step yield & product quality in Adalimumab before and after Capto MMC displacement chromatography using protamine sulfate

| | Yield % | AR1 % | AR2 % | Lys Sum % | HMW % | Monomer % | LMW % |
|---|---|---|---|---|---|---|---|
| Feed | — | 4.4 | 16.5 | 79.1 | 1.0 | 98.8 | 0.2 |
| Product pool | 75 | 2.5 | 14.4 | 83.1 | 0.5 | 99.4 | 0.1 |

Figure 30:
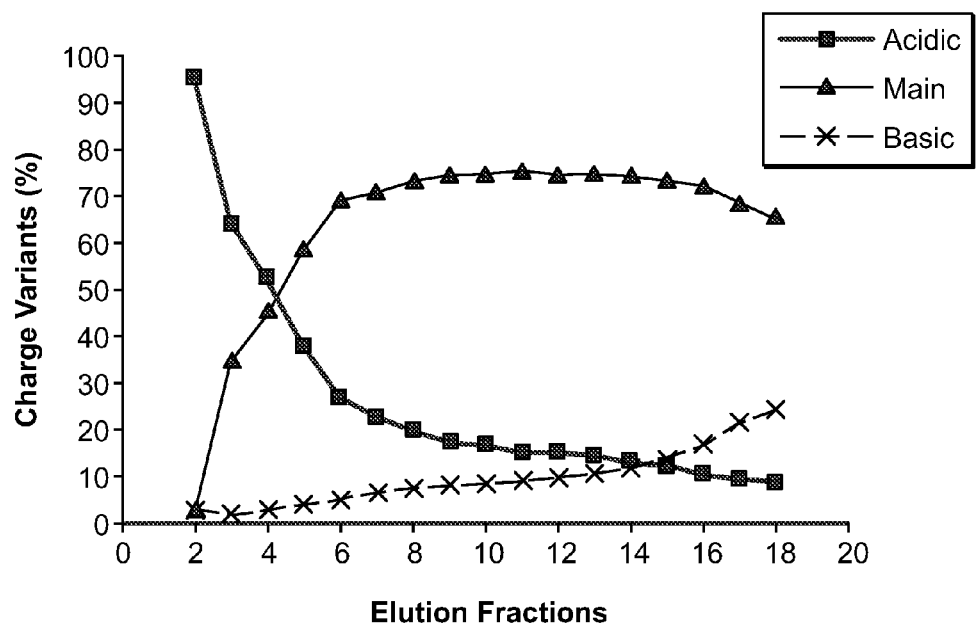
FIG. 30 depicts the separation of mAb X charge variants by Capto MMC displacement chromatography using protamine sulfate.
Figure 31:
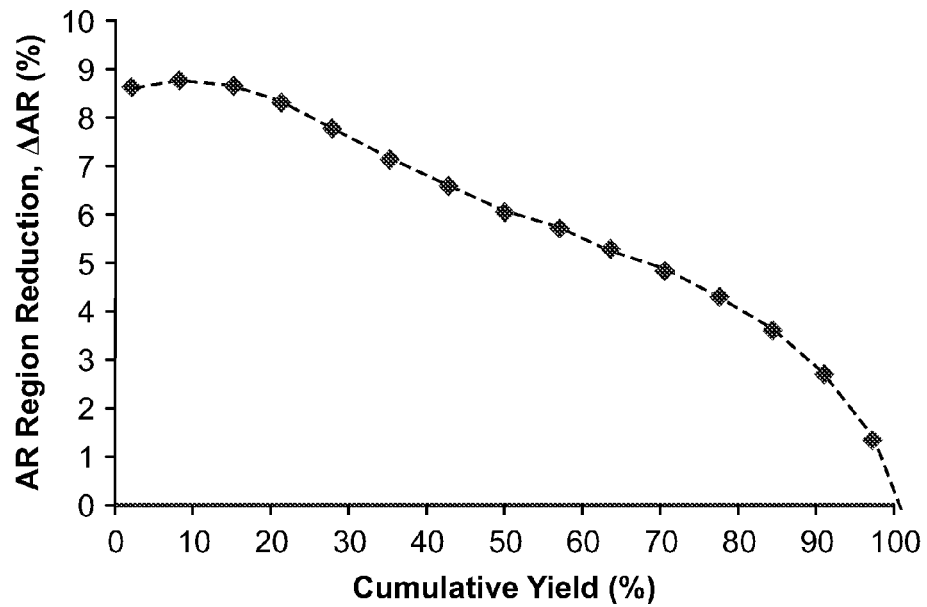
FIG. 31 depicts the reduction of acidic species in mAb X by Capto MMC displacement chromatography using protamine sulfate.

5.7. Displacement Chromatography Separation of Protamine Sulfate for mAb X on Capto MMC Resin Protamine sulfate was evaluated for removing mAb X acidic species on Capto MMC resin. The same feed material as shown in Section 5.4 was used for this set of experiments. As detailed in Table 3, the pH and protamine concentrations were varied in order to generate desired displacement profile. One representative set of working condition is to load Capto MMC column with 40 g/L of mAb X at pH 7.5 and ~6 mS/cm, and to use 0.25 mM protamine sulfate in the pH 7.5, ~6 mS/cm EQ buffer for displacement (Table 3). The separation of charge variants and AR reduction as a function of product recovery are shown in FIGS. 30 and 31, respectively. In this case, 3-5% of AR reduction was resulted at product yield of 70-90%.

The effect of protamine sulfate concentration on mAb X AR reduction by Capto MMC resin was measured in a pH 7, 6 mS/cm Tris/Acetate buffer, as shown in Table 9. Varying the protamine concentration from 0.25 mM to 0.5 mM had very little effect on ΔAR % and product yield, which is quite different from the observations with the Poros XS resin (FIG. 23). The mixed mode MMC resin gave over 3% AR clearance under such selected conditions.

TABLE 9

Reduction of AR level by Capto MMC displacement chromatography for mAb X at different protamine sulfate concentrations

| Expell concentration (mM) | Yield (%) | ΔAR (%) |
| --- | --- | --- |
| 0.25 | 75 | 3.4 |
| 0.5 | 77 | 3.3 |

Figure 32:
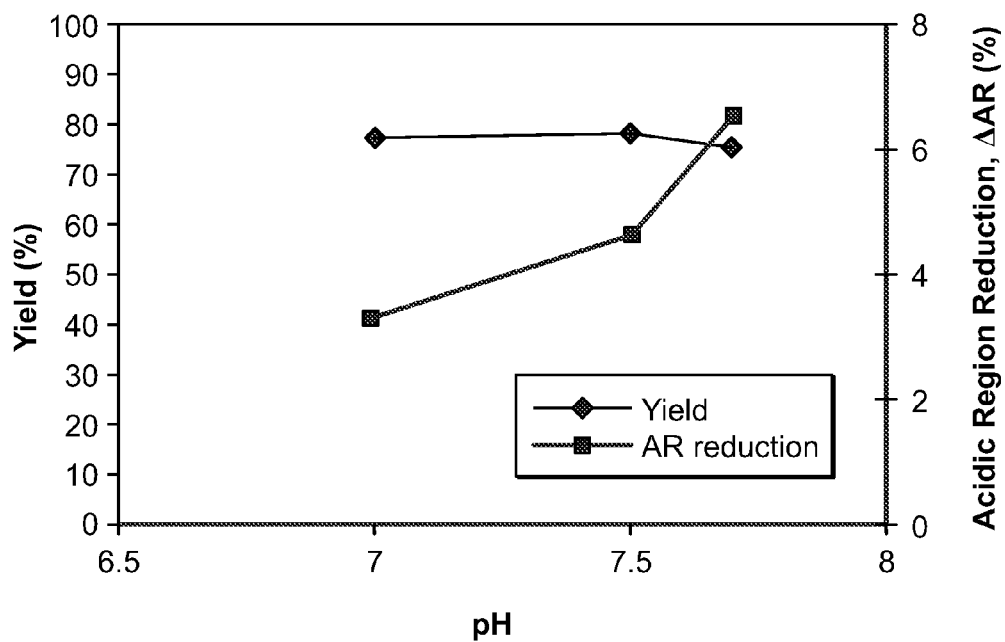
FIG. 32 depicts the effect of pH on acidic species reduction in mAb X by Capto MMC displacement chromatography.
Figure 33:
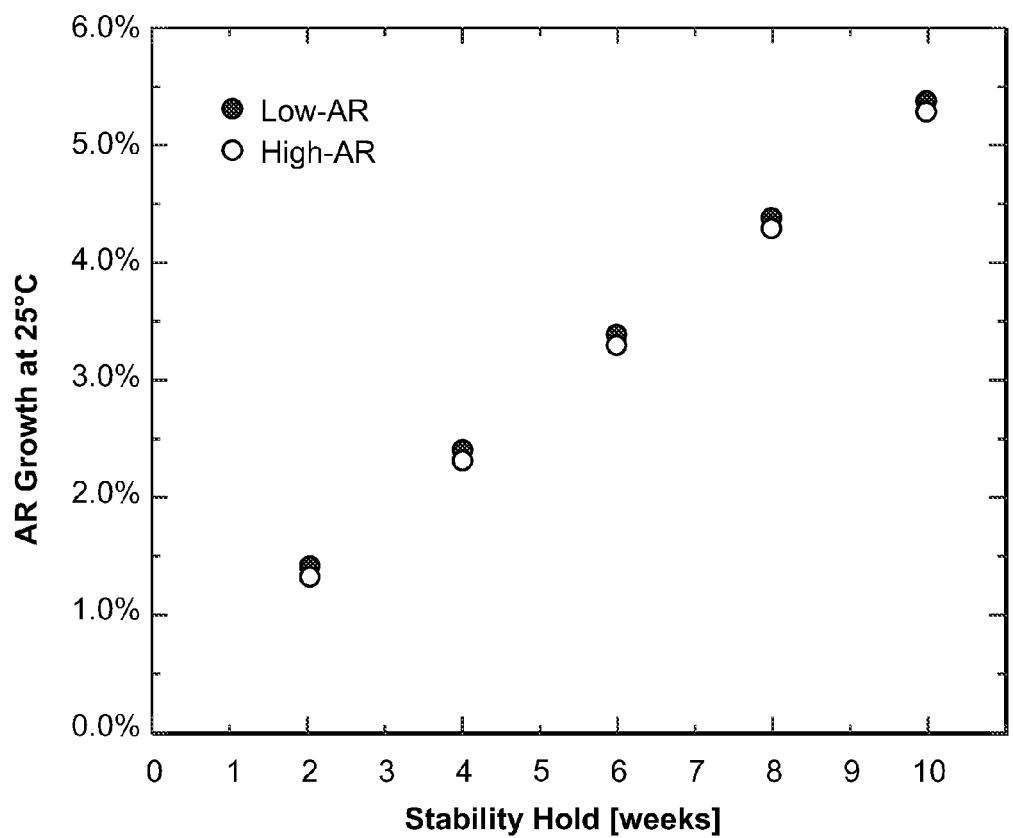
FIG. 33 depicts the AR Growth at 25° C. of low and high AR containing samples.

The effect of displacing buffer pH on AR clearance for mAb X was measured at 0.25 mM protamine sulfate concentration in Tris/Acetate buffer. In this set of experiments, the column was conditioned with an EQ buffer at the respective displacing buffer pH, loaded with protein feed at the same pH and ~6 mS/cm followed by a brief EQ buffer wash before starting the displacement phase. As shown in FIG. 32, ΔAR % increases from 3.3 to 6.5% as pH varies from 7 to 7.7.

The Capto MMC resin also removes aggregates during protamine sulfate displacement chromatography. Table 10 shows the level of charge and size variants of mAb X in product eluate when using 0.5 mM protamine sulfate, pH 7.5 (~6 mS/cm) displacing buffer for separation. The product pool monomer level was enhanced from 98.7% in the feed to 99.2% with aggregate and fragment levels reduced by 50% and 28%, respectively.

TABLE 10

Step yield & product quality for mAb X before and after Capto MMC displacement chromatography using protamine sulfate

| | Yield % | Acidic % | Main % | HMW % | Monomer % | LMW % |
| --- | --- | --- | --- | --- | --- | --- |
| Feed | — | 16.8 | 74.0 | 0.6 | 98.7 | 0.7 |
| Product pool | 77 | 12.4 | 71.8 | 0.3 | 99.2 | 0.5 |

5.8. Displacement Chromatography Separation of Protamine Sulfate for mAb Y on Capto MMC Resin Protamine sulfate was also evaluated for removing mAb Y acidic species on Capto MMC resin. The same feed material as shown in Section 5.5 was used for the experiments here. Two sets of conditions were evaluated here. In one experiment, the equilibration, wash and displacement buffers were adjusted to pH 5.5 and ~6.5 mS/cm, and the displacement buffer contained 0.25 mM protamine sulfate. In the other experiment, all those buffers were adjusted to pH 5, ~6.5 mS/cm and the protamine sulfate concentration was 0.5 mM. In both runs the feed was adjusted to pH 5.5, 5.2-5.5 mS/cm and loaded to the Capto MMC column at ~40 g/L loading level. As shown in Table 11, both sets of conditions resulted in AR % decrease by 5-7% in product pool. In addition, significant aggregates and fragments reduction was achieved with the same product pooling strategy.

TABLE 11

Step yield & product quality for mAb Y before and after Capto MMC displacement chromatography using protamine sulfate

| Conditions | Sample | Yield % | Acidic % | Main % | HMW % | Monomer % | LMW % |
| --- | --- | --- | --- | --- | --- | --- | --- |
| pH 5.5, 0.25 mM Protamine | Feed | — | 16.4 | 75.8 | 8.5 | 91.0 | 0.5 |
| | Product pool | 76 | 9.8 | 79.4 | 2.0 | 97.6 | 0.4 |
| pH 5, 0.5 mM Protamine | Feed | — | 20.9 | 72.8 | 6.3 | 93.2 | 0.5 |
| | Product pool | 75 | 15.9 | 81.1 | 1.6 | 98.2 | 0.2 |

Sections 5.1. to 5.8, above, demonstrate the use of cation exchange and mixed mode displacement chromatography for effectively reducing acidic species along with various other impurities from different mAb feed streams. Under appropriate (or relatively weak) binding conditions, cationic molecules with high affinity for a CEX or multimodal ligand (such as Expell SP1™ and protamine sulfate) can induce the formation of charge variant displacement train, wherein the acidic population is enriched in the front followed by the main isoform, and, thereafter, the basic population. Thus, in certain embodiments, exclusion of those earlier fractions from the remainder eluate results in an AR-reduced product. Alternatively, exclusion of the fractions following the main isoform results in a Lys variant- or basic species-reduced product.

Also demonstrated in the preceding experiments is the fact that the operating pH and displacer concentration can strongly affect the displacement profile and as a result the charge variant, product aggregate, product fragment, and HCP clearance profile. The selection of a particular operating regime with regard to charge variant reduction depends, in general, on the specific protein-resin-displacer system. For example, for Adalimumab, significant AR reduction can be achieved using a displacing buffer with pH in the range of 6-8 with displacer concentration as low as 0.25-0.5 mM. The total AR level (%) in Adalimumab product pool can be reduced by over 10% with an acceptable processing yield (≥75%) from a CEX displacement chromatography process, or 4-7% from a mixed mode displacement chromatography process. Along with acidic species, other product variants or process impurities such as basic species, aggregates, fragments and HCP can be selectively collected or reduced to meet the quality requirements. In addition to the surprisingly effective preparative scale standard one-step displacement operation, unconventional displacement separation schemes are shown above to have unexpected properties, including two-step displacement chromatography and linear gradient displacement chromatography, which can significantly reduce buffer volumes and shorten the processing time without compromising the charge variant, product aggregate, product fragment, and HCP clearance at a given yield target.

5.9 Utility of AR Reduction

The current invention provides a method for reducing acidic species for a given protein of interest. In this example adalimumab was prepared using a combination of AEX and CEX technologies to produce a Low-AR and High-AR sample with a final AR of 2.5% and 6.9%, respectively. Both samples were incubated in a controlled environment at 25° C. and 65% relative humidity for 10 weeks, and the AR measured every two weeks. FIG. 23 shows the growth of AR for each sample over the 10 week incubation. It is evident from FIG. 23 the growth rate of AR is linear and similar between both the Low-AR and High-AR samples. Based on these results the reduced AR material can be stored 3 fold longer before reaching the same AR level as the High-AR sample. This is a significant utility as this can be very beneficial in storage handling and use of the antibody or other proteins for therapeutic use.

6.0 Example AEX 1: Alternative Wash Modalities

In this example, adalimumab and Poros50HQ resin were selected. In each experiment, variations were made in the equilibration, loading, and washing pH values at a given acetate concentration (as specified). Table 12 and Table 13 show the effect of the pH variation in the step yield and AR reduction.

TABLE 12

Differences in pH in Equil/Wash/Load
Poros 50HQ - 15 mM Acetate/Tris - pH 8.7 - 200 g/L

| Equilibration pH | Load pH | Wash pH | Yield (100-100mAU) | ΔAR |
|---|---|---|---|---|
| 8.7 | 8.7 | 8.5 | 83% | 8.7% |
| 9 | 8.5 | 8.5 | 89% | 5.1% |
| 9 | 100 g/L at pH 9.0 100 g/L at pH 8.5 | 8.5 | 94% | 4.5% |

TABLE 13

Differences in pH in Load/Wash
Poros 50HQ - 18 mM Acetate/Tris pH 8.7

| Load pH | Wash pH | Load | Yield | ΔAR |
|---|---|---|---|---|
| 8.6 | 8.4 | 75 g/L | 88.8% | 4.1% |
| 8.6 | 8.5 | 125 g/L | 89.5% | 4.2% |
| 8.6 | 8.6 | 100 g/L | 75.5% | 5.3% |
| 8.7 | 8.4 | 100 g/L | 93.8% | 4.1% |
| 8.7 | 8.5 | 100 g/L | 81.7% | 3.5% |
| 8.7 | 8.5 | 75 g/L | 94.5% | 4.0% |
| 8.7 | 8.6 | 125 g/L | 81.1% | 5.4% |
| 8.7 | 8.6 | 75 g/L | 65.8% | 6.5% |
| 8.8 | 8.4 | 125 g/L | 93.5% | 3.8% |
| 8.8 | 8.5 | 100 g/L | 83.7% | 5.8% |
| 8.8 | 8.6 | 100 g/L | 78.4% | 6.4% |
| 8.8 | 8.6 | 75 g/L | 72.7% | 7.0% |

As discussed in the previous sections, the operational pH and its relation to the product pI is important in the reduction of AR species in AEX. Similarly, the operational pH relative to the pKa of the AEX adsorbent is also important as many mAbs have pI similar to the pKa of the AEX adsorbent. This effect is shown for mAb B with several different AEX adsorbents, with different pKa values, run at with an acetate/Tris buffer at pH 9.1.

As described in previous sections, the Acidic Region for Adalimumab is further grouped into two regions termed AR1 and AR2, based on a certain retention time of the peaks seen on the WCX-10 method. The characteristics of the variants in these two regions are expected to be different and hence the methods that reduce variants belonging to these groups can be specifically delineated.

Further, in addition to achieving a certain AR reduction, it may be desirable to achieve a certain absolute level of AR levels, in consideration of reducing or removing certain variants. The capability of the current invention in achieving a certain absolute level of AR, AR1 and AR2 is demonstrated in Table 14. The method of the current invention can effectively reduce AR2 levels, as an overall decrease in AR levels is achieved. The method can be used to achieve a target absolute level, as exemplified by the data presented in Table 14. Multiple species are present under the group of AR2 and that the current method of invention can be used to reduce such sub-species. The method of the current invention can effectively achieve AR reduction as well as achieve a target absolute level of acidic species as exemplified by the data presented in Table 14.

TABLE 14

AR1, AR2, and AR removal

| Resin | Buffer Condition | pH | Load | Yield | ΔAR1 | Final AR1 | ΔAR2 | Final AR2 | ΔAR |
|---|---|---|---|---|---|---|---|---|---|
| Poros 50PI | 5 mM Acetate/ Tris | 8.5 | 150 g/L | 90% | 0.7% | 1.5% | 1.7% | 9.4% | 2.4% |
| | | | 300 g/L | 94% | 0.3% | 1.9% | 0.6% | 10.5% | 0.9% |
| | | 8.7 | 150 g/L | 87% | 0.9% | 1.2% | 2.7% | 8.2% | 3.6% |
| | | | 300 g/L | 94% | 0.4% | 1.7% | 0.8% | 10.1% | 1.2% |
| | | 8.9 | 150 g/L | 83% | 1.1% | 1.4% | 2.8% | 8.4% | 3.9% |
| | | | 300 g/L | 92% | 0.7% | 1.8% | 0.7% | 10.5% | 1.5% |
| Poros 50HQ | 18 mM Acetate/ Tris | 8.5 | 250 g/L | 91% | 2.9% | 1.1% | 0.9% | 10.8% | 3.8% |
| | | | 350 g/L | 88% | 2.7% | 1.3% | −0.5% | 12.2% | 2.2% |
| | | 8.7 | 250 g/L | 88% | 3.1% | 0.9% | 2.9% | 9.0% | 6.0% |
| | | | 350 g/L | 84% | 2.8% | 1.2% | 0.3% | 11.6% | 3.1% |
| | | 8.9 | 250 g/L | 67% | 2.6% | 1.4% | 3.2% | 8.6% | 5.9% |
| | | | 350 g/L | 75% | 2.3% | 1.7% | 1.3% | 10.5% | 3.6% |

TABLE 14-continued

AR1, AR2, and AR removal

| Resin | Buffer Condition | pH | Load | Yield | ΔAR1 | Final AR1 | ΔAR2 | Final AR2 | ΔAR |
|---|---|---|---|---|---|---|---|---|---|
| CaptoDEAE | 10 mM Acetate/ Tris | 8.5 | 150 g/L | 98% | −0.1% | 2.1% | 0.8% | 10.0% | 0.7% |
| | | | 300 g/L | 97% | 0.0% | 2.0% | 0.1% | 10.8% | 0.1% |
| | | 8.7 | 150 g/L | 78% | 2.4% | 0.8% | 4.7% | 6.4% | 7.1% |
| | | | 300 g/L | 95% | 1.5% | 1.7% | 1.0% | 10.1% | 2.5% |
| | | 8.9 | 150 g/L | 29% | 2.1% | 0.8% | 8.0% | 3.0% | 10.2% |
| | | | 300 g/L | 82% | 1.7% | 1.2% | 3.3% | 7.7% | 5.0% |

Patents, patent applications, publications, product descriptions, GenBank Accession Numbers, and protocols that may be cited throughout this application, the disclosures of which are incorporated herein by reference in their entireties for all purposes. For example, but not by way of limitation, patent applications designated by the following U.S. Application Ser. Nos. are incorporated herein by reference in their entireties for all purposes: 13/830,583; 13/829,989; 13/830,976; 13/831,181; and 13/804,220.

What is claimed is:

1. A method for producing a low acidic species human anti-TNFα antibody composition comprising a human anti-TNFα antibody, or antigen-binding portion thereof, wherein the human anti-TNFα antibody, or antigen-binding portion thereof, comprises a light chain variable region (LCVR) having a CDR1 domain, a CDR2 domain, and a CDR3 domain of adalimumab; and a heavy chain variable region (HCVR) having a CDR1 domain, a CDR2 domain, and a CDR3 domain of adalimumab, the method comprising:
    (a) contacting a first composition comprising the human anti-TNFα antibody, or antigen-binding portion thereof, with a chromatography media, wherein the first composition comprises more than 10% total acidic species of the human anti-TNFα antibody, or antigen-binding portion thereof;
    wherein the acidic species of the human anti-TNFα antibody, or antigen-binding portion thereof, comprise species selected from the group consisting of charge variants, structure variants, fragmentation variants, and any combinations thereof,
    wherein the acidic species of the human anti-TNFα antibody, or antigen-binding portion thereof, do not include process-related impurities selected from the group consisting of host cell proteins, host cell DNA, and media components, and
    wherein the human anti-TNFα antibody, or antigen-binding portion thereof, binds to the chromatography media;
    (b) displacing the human anti-TNFα antibody, or antigen-binding portion thereof, bound to the chromatography media with a displacing buffer; and
    (c) collecting a second composition comprising the displaced human anti-TNFα antibody, or antigen-binding portion thereof, wherein the second composition comprises less than 10% total acidic species of human anti-TNFα antibody, or antigen-binding portion thereof,
    thereby producing a low acidic species human anti-TNFα antibody composition.

2. The method of claim 1, wherein the chromatography media is an ion exchange adsorbent material.

3. The method of claim 2, wherein the ion exchange adsorbent material is an anion exchange adsorbent material.

4. The method of claim 2, wherein the ion exchange adsorbent material is an cation exchange adsorbent material.

5. The method of claim 4, wherein the cation exchange (CEX) adsorbent material is selected from the group consisting of a CEX resin and a CEX membrane adsorber.

6. The method of claim 1, wherein the chromatography media is a multimodal adsorbent material comprising cation exchange and hydrophobic interaction functional groups.

7. The method of claim 1, wherein the pH of the displacing buffer is lower than the isoelectric point of the human anti-TNFα antibody, or antigen-binding portion thereof.

8. The method of claim 7, wherein the pH of the displacing buffer is about 6.0 to about 8.0.

9. The method of claim 1, wherein the displacing buffer carries positive charge.

10. The method of claim 1, wherein the conductivity of the displacing buffer is about 2 to about 20 mS/cm.

11. The method of claim 1, wherein the chromatography media is present in a column having a length of about 10 cm to about 30 cm and wherein flow residence time is about 5 min to about 25 min.

12. The method of claim 1, wherein displacing the human anti-TNFα antibody, or antigen-binding portion thereof, bound to the chromatography media comprises using a first displacing buffer followed by using a second displacing buffer.

13. The method of claim 1, wherein displacing is achieved using a multiple-step displacement, a two-step displacement, or a linear displacement.

14. The method of claim 1, wherein the displacing buffer comprises protamine sulfate.

15. The method of claim 14, wherein the displacing buffer comprises 0.1 to 5 mM protamine sulfate.

16. The method of claim 15, wherein the displacing buffer comprises 0.25 mM protamine sulfate.

17. The method of claim 1, wherein the displacing buffer comprises a quaternary ammonium salt.

18. The method of claim 17, wherein the displacing comprises 0.1 to 10 mM quaternary ammonium salt.

19. The method of claim 18, wherein the displacing buffer comprises 0.5 mM quaternary ammonium salt.

20. The method of claim 1, wherein one displacing buffer is used.

21. The method of claim 1, wherein the chromatography media is a mixed mode media.

22. The method of claim 1, wherein the second composition comprises less than 9% total acidic species of the human anti-TNFα antibody, or antigen-binding portion thereof.

23. The method of claim 1, wherein the second composition comprises less than 8% total acidic species of the human anti-TNFα antibody, or antigen-binding portion thereof.

24. The method of claim 1, wherein the second composition comprises less than 7% total acidic species of the human anti-TNFα antibody, or antigen-binding portion thereof.

25. The method of claim 1, wherein the second composition comprises less than 6% total acidic species of the human anti-TNFα antibody, or antigen-binding portion thereof.

26. The method of claim 1, wherein the second composition comprises less than 5% total acidic species of the human anti-TNFα antibody, or antigen-binding portion thereof.

27. The method of claim 1, wherein the second composition comprises less than 4.5% total acidic species of the human anti-TNFα antibody, or antigen-binding portion thereof.

28. The method of claim 1, wherein the second composition comprises less than 4% total acidic species of the human anti-TNFα antibody, or antigen-binding portion thereof.

29. The method of claim 1, wherein the second composition comprises less than 3% total acidic species of the human anti-TNFα antibody, or antigen-binding portion thereof.

30. The method of claim 1, wherein the second composition comprises less than 1.4% total acidic species of the human anti-TNFα antibody, or antigen-binding portion thereof.

31. The method of claim 1, wherein the human anti-TNFα antibody, or antigen-binding portion thereof, is adalimumab, or an antigen-binding portion thereof.

* * * * *